(12) United States Patent
Sahin

(10) Patent No.: US 9,936,916 B2
(45) Date of Patent: Apr. 10, 2018

(54) SYSTEMS, ENVIRONMENT AND METHODS FOR IDENTIFICATION AND ANALYSIS OF RECURRING TRANSITORY PHYSIOLOGICAL STATES AND EVENTS USING A PORTABLE DATA COLLECTION DEVICE

(71) Applicant: Nedim T. Sahin, Boston, MA (US)

(72) Inventor: Nedim T. Sahin, Boston, MA (US)

( * ) Notice: Subject to any disclaimer, the term of this patent is extended or adjusted under 35 U.S.C. 154(b) by 0 days.

(21) Appl. No.: 14/693,641

(22) Filed: Apr. 22, 2015

(65) Prior Publication Data
US 2015/0223731 A1      Aug. 13, 2015

Related U.S. Application Data

(63) Continuation-in-part of application No. 14/511,039, filed on Oct. 9, 2014.
(Continued)

(51) Int. Cl.
*A61B 5/00* (2006.01)
*A61B 5/16* (2006.01)
*A61B 5/11* (2006.01)

(52) U.S. Cl.
CPC ............ *A61B 5/486* (2013.01); *A61B 5/0022* (2013.01); *A61B 5/1112* (2013.01);
(Continued)

(58) Field of Classification Search
CPC ........ A61B 5/11; A61B 5/1101; A61B 5/6803
(Continued)

(56) References Cited

U.S. PATENT DOCUMENTS 5,706,416 A    1/1998  Mann et al.
6,724,298 B2   4/2004  Smith
(Continued)

OTHER PUBLICATIONS

Neuroscan "A Child's World Just Became Clearer," Autism Diagnosis: from months to minutes, http://neuroscanpro.com/ pp. 1-8.
(Continued)

*Primary Examiner* — John R Downey
(74) *Attorney, Agent, or Firm* — Gardella Grace P.A.

(57) ABSTRACT

In one aspect, the systems, environment, and methods described herein support anticipation and identification of adverse health events and/or atypical behavioral episodes such as Autistic behaviors, epileptic seizures, heart attack, stroke, and/or narcoleptic "sleep attacks" using a portable data collection device. In another aspect, the systems, environment, and methods described herein support measurement of motions and vibrations associated with recurring transitory physiological states and events using a portable data collection device. For example, motion and vibration measurements may be analyzed to identify pronounced head motion patterns indicative of specific heart defects, neurodegenerative conditions, inner ear or other balance problems, or types of cardiac disease. In another example, motion and vibration measurements may be analyzed to identify slow-wave changes indicative of temporary conditions such as intoxication, fatigue, distress, aggression, attention deficit, anger, and/or narcotic ingestion as well as temporary or periodic normal events, such as ovulation, pregnancy, and sexual arousal.

27 Claims, 28 Drawing Sheets

Related U.S. Application Data

(60) Provisional application No. 61/888,531, filed on Oct. 9, 2013, provisional application No. 61/943,727, filed on Feb. 24, 2014.

(52) U.S. Cl.
CPC .............. *A61B 5/1123* (2013.01); *A61B 5/16* (2013.01); *A61B 5/6803* (2013.01); *A61B 5/743* (2013.01); *A61B 5/7405* (2013.01); *A61B 5/7455* (2013.01); *A61B 2560/0242* (2013.01)

(58) Field of Classification Search
USPC ......................................... 600/300, 301, 595
See application file for complete search history.

(56) References Cited

U.S. PATENT DOCUMENTS

| | | | |
|---|---|---|---|
| 7,766,828 B2 | 8/2010 | Ishii et al. | |
| 8,140,143 B2 | 3/2012 | Picard et al. | |
| 8,184,983 B1* | 5/2012 | Ho | H04B 10/1143 345/156 |
| 8,188,880 B1 | 5/2012 | Chi et al. | |
| 8,203,502 B1 | 6/2012 | Chi et al. | |
| 8,306,610 B2 | 11/2012 | Mirow | |
| 8,311,605 B2 | 11/2012 | Wilder-Smith et al. | |
| 8,371,693 B2 | 2/2013 | Ebisawa | |
| 8,396,530 B1 | 3/2013 | Wilder-Smith et al. | |
| 8,441,356 B1 | 5/2013 | Tedesco et al. | |
| 8,494,507 B1 | 7/2013 | Tedesco et al. | |
| 8,630,633 B1 | 1/2014 | Tedesco et al. | |
| 8,641,646 B2 | 2/2014 | Colborn | |
| 8,655,441 B2 | 2/2014 | Fletcher et al. | |
| 8,669,864 B1 | 3/2014 | Tedesco et al. | |
| 8,690,325 B1 | 4/2014 | Straus et al. | |
| 8,708,702 B2 | 4/2014 | Paul | |
| 8,714,982 B2 | 5/2014 | Wimsatt | |
| 8,774,893 B2 | 7/2014 | Wilder-Smith et al. | |
| 8,777,630 B2 | 7/2014 | Duffy | |
| 8,795,173 B2 | 8/2014 | Poh et al. | |
| 8,810,388 B2 | 8/2014 | Jacobs et al. | |
| 8,854,282 B1 | 10/2014 | Wong | |
| 2002/0142271 A1 | 10/2002 | Curtin | |
| 2002/0183657 A1* | 12/2002 | Socci | A61B 5/1114 600/595 |
| 2003/0107707 A1* | 6/2003 | Fisher | A61B 3/113 351/159.74 |
| 2005/0107716 A1* | 5/2005 | Eaton | A61B 5/0073 600/544 |
| 2007/0117073 A1 | 5/2007 | Walker et al. | |
| 2008/0214903 A1 | 9/2008 | Orbach | |
| 2009/0312817 A1* | 12/2009 | Hogle | A61B 5/0492 607/54 |
| 2009/0319459 A1 | 12/2009 | Brezeal et al. | |
| 2010/0268056 A1* | 10/2010 | Picard | A61B 5/0531 600/388 |
| 2011/0053129 A1 | 3/2011 | Basson et al. | |
| 2011/0263946 A1* | 10/2011 | el Kaliouby | A61B 5/1128 600/300 |
| 2012/0313746 A1 | 12/2012 | Rahman et al. | |
| 2012/0314045 A1* | 12/2012 | Billard | A61B 3/113 348/78 |
| 2012/0322380 A1 | 12/2012 | Nannarone et al. | |
| 2013/0021374 A1 | 1/2013 | Miro et al. | |
| 2013/0046150 A1* | 2/2013 | Devanaboyina | G06F 19/345 600/301 |
| 2013/0106674 A1 | 5/2013 | Wheeler et al. | |
| 2013/0245376 A1 | 9/2013 | Oku | |
| 2013/0245396 A1* | 9/2013 | Berman | G06F 19/3481 600/301 |
| 2014/0016800 A1 | 1/2014 | Dong et al. | |
| 2014/0023999 A1* | 1/2014 | Greder | A61B 5/0482 434/236 |
| 2014/0243637 A1 | 8/2014 | Rahman et al. | |
| 2014/0368980 A1 | 12/2014 | Nanavati et al. | |
| 2015/0099946 A1 | 4/2015 | Sahin | |

OTHER PUBLICATIONS

Jonah Comstock, "MC10, biopharma company UCB team up on neurological diseases," Jul. 28, 2014, http://mobihealthnews.com/35192/mc10-biopharma-company-ucb-team-up-on-neurologica . . . , pp. 1-2.

Internetmedicine.com, "Exclusive: Researchers turn Google Glass into Health sensor," Sep. 6, 2014, http://internetmedicine.com/2014/09/06/exclusive-researchers-turn-google-glass-into-health . . . , pp. 1-9.

International Search Report issued for PCT/US2015/017306 dated May 28, 2015.

International Written Opinion issued for PCT/US2015/017306 dated May 28, 2015.

Javier Hernandez, et al.; "BioGlass: Physiological Parameter Estimation Using a Head-mounted Wearable Device"; BioGlass; retrieved from internet: http://bioglass.media.mit.edu/ on Jun. 10, 2015.

"Epson's Next-Generation Augmented Reality Smart Glasses Built to Revolutionize Gaming, Video Entertainment and More"; Epson, http://global.epson.com/newsroom/2014/news_20140107.html, Las Vegas, NV, United States, Jan. 7, 2014.

Michael Sung et al., "Wearable Feedback Systems for Rehabilitation," Journal of NeuroEngineering and Rehabilitation, Published Jun. 29, 2005, BioMed Central, Cambridge,MA, pp. 1-12.

Adolfo M. Bronstein, "Visual Vertigo Syndrome: Clinical and Posturography Findings,"Journal of Neurology, Neurosurgery, and Psychiatry, Accepted Jul. 11, 1995, Queen Square, London, pp. 472-476.

Abdelkrim Hadjidj et al., "Wireless Sensor Networks for Rehabilitation—Applications: Challenges and Opportunities," HAL, Jun. 14, 2012, pp. 1-16.

Tal Shany et al., "Sensors-Based Wearable Systems for Monitoring of Human Movement and Falls," IEEE Sensors Journal, vol. 12, Mar. 3, 2012, pp. 658-670.

Johannes Michalak, Ph.D. et al., "Embodiment of Sadness and Depression—Gait Patterns Associated with Dysporic Mood," American Psychosomatic Society, 2009, pp. 580-587.

Justin J. Kavanagh et al., "Accelerometry: A Technique for Quantifying Movement Patterns During Walking," ScienceDirect, Gait & Posture, 2007, pp. 1-15.

"LifeSafe Mobile Safety Solutions," http://www.livesafemobile.com/that-we-offer/hiqher-education/, Mar. 2015, pp. 1-3.

"Mobile Tracking," USF One Card and Campus Security Systems, http://www.usfca.edu/onecard/pathlight/, Mar. 2015, pp. 1-2.

International Search Report and Written Opinion dated Jul. 26, 2016 in PCT/US2016/028952.

International Preliminary Report on Patentability dated Nov. 2, 2017 in related International PCT Application No. PCT/US2016/028952, 10 pages.

Hall, John E., Functional Organization of the Human Body and Control of the "Internal Environment," Guyton and Hall of Medical Physiology, 13th edition, 6 pages.

Physical, Definition by Merriam-Webster, retrieved Sep. 5, 2017 <https://www.merriam-webster.com/dictionary/physical>, 7 pages.

Physiological, Definition by Merriam-Webster, retrieved Sep. 5, 2017 <https://www.merriam-webster.com/dictionary/physiological>, 4 pages.

Physiology, Definition by Merriam-Webster, retrieved Sep. 5, 2017 <https://www.merriam-webster.com/dictionary/physiology>, 5 pages.

Morvillo, Nancy et al., The MCAT Biology Book, retrieved from <http://ebookcentral.proquest.com> Copyright 2007.

Webster, John G., The Physiological Measurement Handbook, Series in Medical Physics and Biomedical Engineering, 8 pages.

\* cited by examiner

SYSTEMS, ENVIRONMENT AND METHODS FOR IDENTIFICATION AND ANALYSIS OF RECURRING TRANSITORY PHYSIOLOGICAL STATES AND EVENTS USING A PORTABLE DATA COLLECTION DEVICE

RELATED APPLICATIONS

The present application is related to and claims the priority of U.S. patent application Ser. No. 14/511,039 entitled "Systems, Environment and Methods for Evaluation and Management of Autism Spectrum Disorder using a Wearable Data Collection Device" and filed Oct. 9, 2014, which claims the priority of U.S. Provisional Application No. 61/888,531 entitled "A Method and Device to Provide Information Regarding Autism Spectrum Disorders" and filed Oct. 9, 2013, and U.S. Provisional Application No. 61/943,727 entitled "Method, System, and Wearable Data Collection Device for Evaluation and Management of Autism Spectrum Disorder" and filed Feb. 24, 2014, the contents of each of which are hereby incorporated by reference in their entireties.

BACKGROUND

Autism probably begins in utero, and can be diagnosed at 4-6 months. However, right now in America, Autism is most often diagnosed at 4-6 years. The median diagnosis age in children with only 7 of the 12 classic Autism Spectrum Disorder symptoms is over 8. In these missed years, the child falls much further behind his or her peers than necessary. This tragedy is widespread, given that 1 in 42 boys is estimated to have Autism (1 in 68 children overall) (based upon U.S. Centers for Disease Control and Prevention, surveillance year 2010). Additionally there are few methods of managing or treating Autism, and almost no disease-modifying medical treatments. Why do these diagnosis and treatment gaps exist?

There is no blood test for autism. Nor is there a genetic, neural or physiological test. Astonishingly, the only way parents can know if their child has autism is to secure an appointment with multiple doctors (pediatrician, speech pathologist, perhaps neurologist) who observe the child playing and interacting with others, especially with the caregiver. This is time-consuming, must be done during doctors' hours, is challenging and contains subjective components, varies by clinician, does not usually generate numerical data or closely quantified symptoms or behaviors; and demands resources, knowledge and access to the health system—all contributing to delayed diagnosis.

There are also social factors. A parent's suspicion that his/her child has autism generally takes time to grow, especially with the first child or in parents with little child experience (no frame of reference). Furthermore, the decision to seek help may be clouded by fear, doubt, denial, guilt, stigma, embarrassment, lack of knowledge, distrust of the medical system, and confusion. Once the decision is made, it can be a protracted, uphill battle to find the right care center and secure the screening appointment and a correct diagnosis. All these factors are amplified for at-risk families with low SES, low education level, language and cultural barriers, familial ASD; and in single-parent or dual job families. Time that passes before diagnosis reduces the child's social and emotional development, learning of language, and eventual level of function in society.

Even if the family surmounts various hurdles and comes in for an official diagnosis, hospital admission and the test environment can be daunting and unnatural, especially for those with language, cultural or SES barriers.

In this context, a shy child may seem autistic and an ASD child may completely shut down, especially since ASD children are particularly averse to changes in familiar settings and routines. Thus, the child may be diagnosed as further along the Autism spectrum than is the reality, and false diagnoses such as retardation may be attached. This has profound consequences in terms of what schooling options are available to the child, how the parents and community treats the child, and the relationship that gets set up between the parents and the healthcare system. Even in a friendly testing lab, clinicians cannot see the child play and interact exactly as he/she does in the familiar home environment, and can never see the child through the caregiver's eyes, nor see the world through the child's eyes. Importantly, there are no widely adopted systems for objectively quantifying behavioral markers or neural signals associated with ASD, especially at home.

Even when and if a diagnosis is achieved, there are few options available to the family (or to the school or health care giver) that quantify the degree of severity of the child's symptoms. Autism is a spectrum of course, and people with autism spectrum disorders have a range of characteristic symptoms and features, each to varying degrees of severity if at all. Measuring these and characterizing the overall disorder fingerprint for each person is an important advance for the initial characterization, as per above, but importantly this fingerprint is dynamic over time, especially in the context of attempted treatments and schooling options, so measuring the changing severity and nature of each feature is important. This is the tracking or progress-assessment framework. Additionally, perhaps one of the greatest unmet needs within ASD comes in terms of the treatment or training framework. That is to say, mechanisms for providing intervention of one kind or another that can have a disease-modifying or symptom-modifying impact. There are few options available to the families affected, and again, there are few options for rigorously quantifying the results.

SUMMARY

Various systems and methods described herein support anticipation and identification of adverse health events and/or atypical behavioral episodes such as Autistic behaviors, epileptic seizures, heart attack, stroke, and/or narcoleptic "sleep attacks" using a wearable data collection device. In another aspect, the systems, environment, and methods described herein support measurement of motions and vibrations associated with recurring transitory physiological states and events using a wearable data collection device.

In one aspect, the present disclosure relates to systems and methods developed to better track, quantify, and educate an individual with an unwellness condition or neurological development challenge. In some embodiments, certain systems and methods described herein monitor and analyze an individual's behaviors and/or physiology. The analysis, for example, may identify recurring transient physiological states or events. For example, motion and vibration measurements may be analyzed to identify pronounced head motion patterns indicative of specific heart defects, neurodegenerative conditions, inner ear or other balance problems, or types of cardiac disease. During the pulse cycle, for example, blockages of the atrium may cause a particular style of motion, while blockages of the ventricle may cause a different particular style of motion (e.g., back and forth vs. side-to-side, etc.). Vestibular inner ear issues, for example as a result of a percussive injury such as a blast injury disrupting inner ear physiology, can lead to poor balance and balance perception, resulting in measurable tilt and head motion. In another example, motion and vibration measurements may be analyzed to identify slow-wave changes indicative of temporary anomalous states such as intoxication, fatigue, and/or narcotic ingestion as well as temporary or periodic normal events, such as ovulation, pregnancy, and sexual arousal.

A slow-wave change can be measurable over a lengthier period of time such as a day, series of days, week(s), month(s), or even year. Mean activity, for example, may be affected by time of the day and/or time of the year. The motions, for example, may include small eye motions, heart rate, mean heart variability, respiration, etc. Any of these systemic motions may become disregulated and demonstrate anomalies. Certain systems and methods described herein, in some embodiments, provide assistance to the individual based upon analysis of data obtained through monitoring.

In one aspect, motion signatures may be derived from a baseline activity signature particular to an individual or group of individuals, such as a common gait, customary movements during driving, or customary movements while maintaining a relaxed standing position. In relation to a group of individuals, for example, the group may contemplate similar physiological disabilities, genetic backgrounds (e., family members), sex, age, race, size, sensory sensitivity profiles (e.g., auditory vs. visual vs. haptic, etc.), responsiveness to pharmaceuticals, behavioral therapies, and/or other interventions, and/or types of digestive problems.

In one aspect, the present disclosure relates to systems and methods for inexpensive, non-invasive measuring and monitoring of breathing, heart rate, and/or cardiovascular dynamics using a portable or wearable data collection device. Breathing, heart rate, and/or cardiovascular dynamics, in one aspect, may be derived through analysis of a variety of motion sensor data and/or small noise data. It is advantageous to be able to measure heart rate and cardiovascular dynamics as non-invasively as possible. For instance, the ability to avoid electrodes, especially electrodes that must be adhered or otherwise attached to the skin, is in most situations preferable, particularly for children who do not like extraneous sensory stimulus on their skin. It is also advantageous to be able to derive, from a non-invasive signal, additional cardiovascular dynamics beyond simply heart rate, such as dynamics that may indicate unwellness and which may usually require multi-lead ECG setups and complex analysis.

In some embodiments, a wearable data collection device including one or more motion sensors and/or electromagnetic sensors capable of discerning small motions of the body and/or one or more microphones capable of discerning small noises of the body is placed comfortably and removably on an individual without need for gels or adhesives. In a further example, the wearable data collection device may include one or more imaging sensors for capturing a time series of images or video imagery. The time progression of image data may be analyzed to identify small motions attributable to the wearer. The wearable data collection device may be a device specifically designed to measure and monitor cardiovascular dynamics of the body or a more general purpose personal wearable computing device capable of executing a software application for analyzing small motion data (e.g., motion sensor data, audio data, electromagnetic data, and/or small noise data) to obtain physiological characteristics such as cardiovascular dynamics data or a biometric signature pattern.

In some implementations, the system goes beyond the evaluation stage to track an individual's ongoing progress. The system, for example, could provide high-frequency (e.g., up to daily) assessments, each with perhaps hundreds or thousands or more data points or samples such as, in some examples, assessments of chronic anomalous physiological states and events (e.g., balance problems, Autistic behaviors, slow-wave changes indicative of unwellness conditions, and small head motion patterns indicative of unwellness conditions), assessments of chronic and normal physiological events (e.g., heart rate, breathing, etc.), and assessments of temporary anomalous events (e.g., heart attack, stroke, seizure, falls, etc.). Assessments can be incorporated into the individual's everyday home life to measure the individual's ongoing progress (e.g., symptom management, condition progress, etc.).

To enable such ongoing assessment as well as to support the training and education of an individual with a neurological development disorder or unwellness condition, in some implementations, applications for use with a portable computing device or wearable data collection device may be made available for download to or streaming on the wearable data collection device via a network-accessible content store such as iTunes® by Apple, Inc. of Cupertino, Calif. or Google Play™ store by Google Inc. of Menlo Park, Calif., or YouTube™ by Google Inc. or other content repositories, or other content collections. Content providers, in some examples, can include educators, clinicians, physicians, and/or parents supplied with development abilities to build new modules for execution on the wearable data collection device evaluation and progress tracking system. Content can range in nature from simple text, images, or video content or the like, to fully elaborated software applications ("apps") or app suites. Content can be stand-alone, can be playable on a wearable data-collection device based on its existing capabilities to play content (such as in-built ability to display text, images, videos, apps, etc., and to collect data), or can be played or deployed within a content-enabling framework or platform application that is designed to incorporate content from content providers. Content consumers, furthermore, can include individuals diagnosed with a particular unwellness condition or their families as well as clinicians, physicians, and/or educators who wish to incorporate system modules into their professional practices.

In some implementations, in addition to assessment, one or more modules of the system provide training mechanisms for supporting the individual's coping and development with an unwellness condition and its characteristics. In the aspect of a balance problem such as inner ear damage, a balance coaching training mechanism may be used to accurately compensate for the effects of the vestibular system damage through correction and feedback. In the aspect of ASD, training mechanisms may include, in some examples, training mechanisms to assist in recognition of emotional states of others, social eye contact, language learning, language use and motivation for instance in social contexts, identifying socially relevant events and acting on them appropriately, regulating vocalizations, regulating overt inappropriate behaviors and acting-out, regulating temper and mood, regulating stimming and similar behaviors, coping with sensory input and aversive sensory feelings such as overload, and among several other things, the learning of abstract categories.

DETAILED DESCRIPTION

Figure 1A:
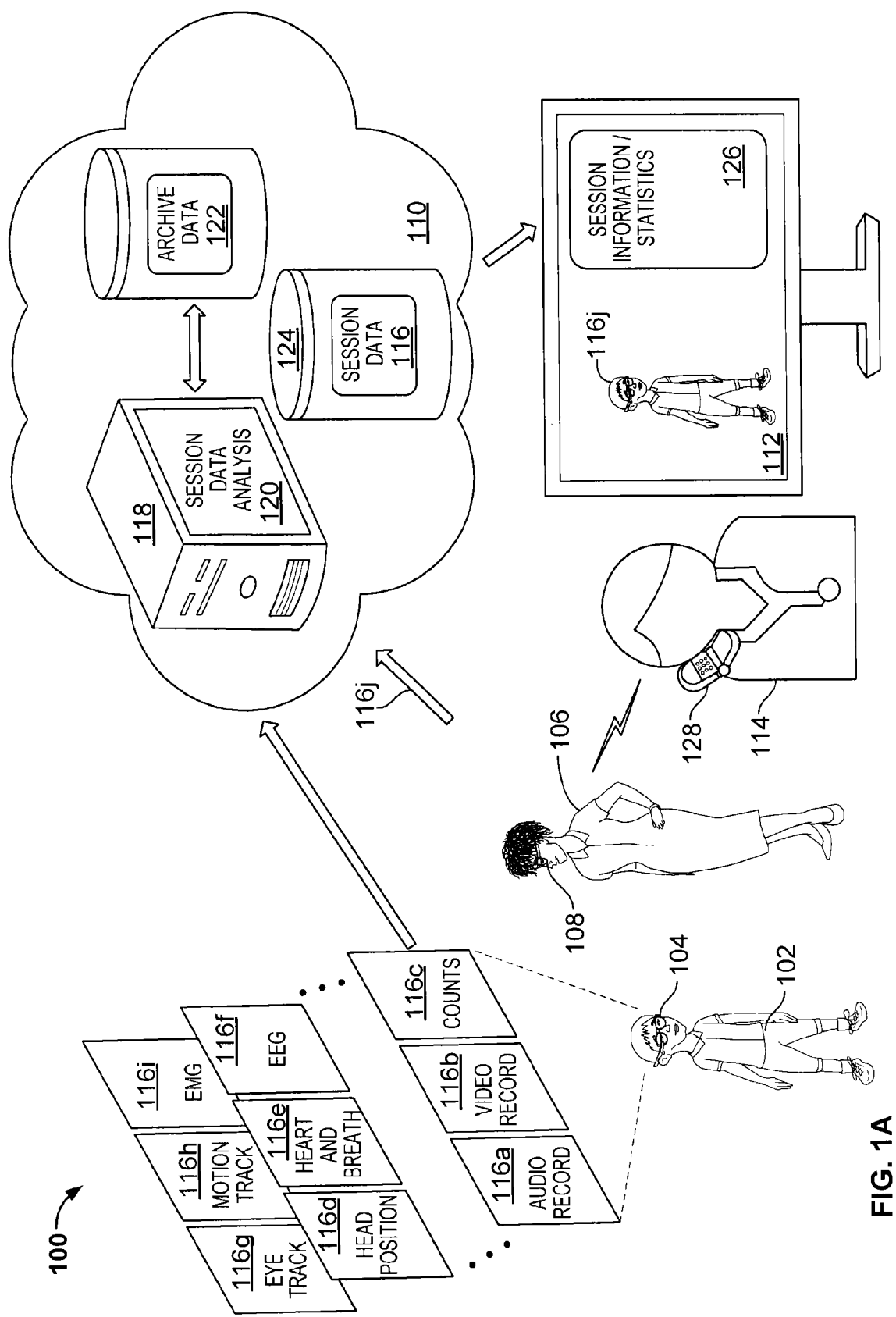
FIG. 1A is a block diagram of an example environment for evaluating an individual for Autism Spectrum Disorder using a wearable data collection device.

As illustrated in FIG. 1A, an environment 100 for evaluating an individual 102 for autism spectrum disorder includes a wearable data collection device 104 worn by the individual 102 and/or a wearable data collection device 108 worn by a caregiver 106, such that data 116 related to the interactions between the individual 102 and the caregiver 108 are recorded by at least one wearable data collection device 104, 108 and uploaded to a network 110 for analysis, archival, and/or real-time sharing with a remotely located evaluator 114. In this manner, evaluation activities, to be evaluated in real time or after the fact by the evaluator 114, may be conducted in the individual's accustomed surroundings without the stress and intimidation of the evaluator 114 being present. For example, evaluation activities may be conducted in a family's home environment at a time convenient for the family members.

Evaluation activities, in some implementations, include a set of play session phases incorporating, for example, various objects for encouraging interaction between the caregiver 106 and the individual 102. For example, the caregiver 106 may be supplied with an evaluation kit including one or both of the individual's data collection device 104, the caregiver data collection device 108, a set of interactive objects, and instructions on how to conduct the session. The set of interactive objects, in one example, may include items similar to those included within the Screening Tool for Autism in Toddlers (STAT™) test kit developed by the Vanderbilt University Center for Technology Transfer & Commercialization of Nashville, Tenn. The instructions, in one example, may be provided textually, either online or in a booklet supplied in the evaluation kit. In another example, the instructions are presented in video form, either online or in a video recording (e.g., DVD) included in the kit.

In some implementations, the instructions are supplied via the caregiver wearable data collection device 108. For example, the wearable data collection device 108 may include an optical head-mounted display (OHMD) such that the caregiver may review written and/or video instructions after donning the wearable data collection device 108. The caregiver may perform a play session or test session based on the instructions, or by mirroring or responding to step-by-step directions supplied by a remote evaluator 114, who can be a trained clinician or autism specialist, such that the remote evaluator 114 can walk the caregiver 106 through the process step by step, and the remote evaluator 114 can observe and evaluate the process and the behaviors of the individual 102 and other data in real time and directly through the eyes of the caregiver 106 (via a camera feed from the data collection device 104).

The wearable data collection device 104 or 108, in some implementations, is a head-mounted wearable computer. For example, the wearable data collection device 104 or 108 may be a standard or modified form of Google Glass™ by Google Inc. of Mountain View, Calif. In other examples, the wearable data collection device 104 or 108 is mounted in a hat, headband, tiara, or other accessory worn on the head. The caregiver 108 may use a different style of data collection device 108 than the individual 102. For example, a caregiver may use a glasses style wearable data collection device 108, while the subject uses a head-mounted visor style of data collection device 104.

In some implementations, the data collection device 104 for the individual 102 and/or the data collection device 108 for the caregiver 106 is be composed of multiple portions 105 of body-mountable elements configured to mount on different areas of the body. In general, the wearable data collection device 104 or 108 may be configured as a single, physically-contiguous device, or as a collection of two or more units that can be physically independent or semi-independent of each other but function as a whole as a wearable data collection device 104 or 108. For example, the data collection device 104 or 108 may have a first portion including an optical head-mounted display (OHMD) and which therefore is mounted on or about the head such as in a modified version of eyeglasses or on a visor, hat, headband, tiara or other accessory worn on the head. Further, the data collection device 104 or 108 may have a second portion separate from the first portion configured for mounting elsewhere on the head or elsewhere on the body. The second portion can contain, in some examples, sensors, power sources, computational components, data and power transmission apparatuses, and other components. For instance, in an illustrative example, the first portion of data collection device 104 or 108 may be used to display information to the user and/or perform various tasks of user interface, whereas the second portion of data collection device 104 or 108 may be configured to perform sensing operations that are best suited to specific parts of the body, and/or may be configured to perform computation and in so doing may consume power all of which may require a size and bulk that is better suited to be elsewhere on the body than a head-mounted device. Further to the example, the second portion of data collection device 104 or 108 may be configured to mount on the wrist or forearm of the wearer. In a particular configuration, the second portion may have a design similar to a watch band, where the second portion can be interchanged with that of a standard-sized wrist watch and thereby convert an off-the-shelf wrist watch into a part of a smart ecosystem and furthermore hide the presence of the second portion of the data collection device 104 or 108. Although described as having two portions, in other implementations, the wearable data collection device 104 or 108 may include three or more portions physically independent of each other with each portion capable of inter-communicating with at least one of the other portions. Many other configurations are also anticipated.

The wearable data collection device 104 for the subject may be customized for use by an individual, for instance by making it fit the head better of someone of the age and size of a given individual 102, or by modifying the dynamics of the display such that it is minimally distracting for the individual 102. Another possible customization of the wearable data collection device 104 includes regulating the amount of time that the wearable data collection device 104 can be used so as to cause minimal change to the individual 102, such as to the developing visual system of the individual 102. The wearable data collection device 104, in a further example, may be customized for the individual 102 to make the wearable data collection device 104 palatable or desirable to be worn by the individual 102 for instance by cosmetic or sensory modifications of the wearable data collection device 104.

The wearable data collection device 104 or 108, in some implementations, can be modified for the type of usage discussed herein, for instance by equipping it with an extended-life power source or by equipping it with an extended capacity for data acquisition such as video data acquisition with features such as extended memory storage or data streaming capabilities, or the like.

Rather than performing the described functionality entirely via a wearable data collection device 104 or 108, in some implementations, the data collection device 104 or 108 includes a bionic contact lens. For example, the OHMD may be replaced with a bionic contact lens capable of providing augmented reality functionality. In another example, an implantable device, such as a visual prosthesis (e.g., bionic eye) may provide augmented reality functionality.

The wearable data collection device 104 or 108 can be arranged on the body, near the body, or embedded within the body, in part or entirely. When one or more components of the wearable data collection device 104 or 108 is embedded within the body, the one or more components can be embedded beneath the skin; within the brain; in contact with input or output structures of the body such as peripheral nerves, cranial nerves, ganglia, or the spinal cord; within deep tissue such as muscles or organs; within body cavities; between organs; in the blood; in other fluid or circulatory systems; inside cells; between cells (such as in the interstitial space); or in any other manner arranged in a way that is embedded within the body, permanently or temporarily. When one or more components of the wearable data collection device 104 or 108 is embedded within the body, the one or more components may be inserted into the body surgically, by ingestion, by absorption, via a living vector, by injection, or other means. When one or more components of the wearable data collection device 104 or 108 is embedded within the body, the one or more components may include data collection sensors placed in direct contact with tissues or systems that generate discernible signals within the body, or stimulator units that can directly stimulate tissue or organs or systems that can be modulated by stimulation. Data collection sensors and stimulator units are described in greater detail in relation to FIG. 12.

The wearable data collection device 104 or 108 can be configured to collect a variety of data 116. For example, a microphone device built into the data collection device 104 or 108 may collect voice recording data 116a, while a video camera device built into the data collection device 104 or 108 may collect video recording data 116b. The voice recording data 116a and video recording data 116b, for example, may be streamed via the network 110 to an evaluator computing device (illustrated as a display 112) so that the evaluator 114 reviews interactions between the individual 102 and the caregiver 108 in real-time. For example, as illustrated on the display 112, the evaluator is reviewing video recording data 116j recorded by the caregiver wearable data collection device 108. Additionally, the evaluator may be listening to voice recording data 116a.

Furthermore, in some implementations, the wearable data collection device 104 is configured to collect a variety of data regarding the movements and behaviors of the individual 102 during the evaluation session. For example, the wearable data collection device 104 may include motion detecting devices, such as one or more gyroscopes, accelerometers, global positioning system, and/or magnetometers used to collect motion tracking data 116h regarding motions of the individual 102 and/or head position data 116d regarding motion particular to the individual's head. The motion tracking data 116h, for example, may track the individual's movements throughout the room during the evaluation session, while the head position data 116d may track head orientation. In another example, the motion tracking data 116*h* may collect data to identify repetitive motions, such as jerking, jumping, flinching, first clenching, hand flapping, or other repetitive self-stimulating ("stimming") behaviors.

In some implementations, the wearable data collection device 104 is configured to collect eye tracking data 116*g*. For example, the wearable data collection device 104 may include an eye tracking module configured to identify when the individual 102 is looking straight ahead (for example, through the glasses style wearable data collection device 104) and when the individual 102 is peering up, down, or off to one side. Techniques for identifying eye gaze direction, for example, are described in U.S. Patent Application No. 20130106674 entitled "Eye Gaze Detection to Determine Speed of Image Movement" and filed Nov. 2, 2011, the contents of which are hereby incorporated by reference in its entirety. In another example, the individual's data collection device 104 is configured to communicate with the caregiver data collection device 108, such that the wearable data collection devices 104, 108 can identify when the individual 102 and the caregiver 106 have convergent head orientation. In some examples, a straight line wireless signal, such as a Bluetooth signal, infrared signal, or RF signal, is passed between the individual's wearable data collection device 104 and the caregiver wearable data collection device 108, such that a wireless receiver acknowledges when the two wearable data collection devices 104, 108 are positioned in a substantially convergent trajectory.

The wearable data collection device 104, in some implementations, is configured to monitor physiological functions of the individual 102. In some examples, the wearable data collection device 104 may collect heart and/or breathing rate data 116*e* (or, optionally, electrocardiogram (EKG) data), electroencephalogram (EEG) data 116*f*, and/or Electromyography (EMG) data 116*i*). The wearable data collection device 104 may interface with one or more peripheral devices, in some embodiments, to collect the physiological data. For example, the wearable data collection device 104 may have a wired or wireless connection with a separate heart rate monitor, EEG unit, or EMG unit. In other embodiments, at least a portion of the physiological data is collected via built-in monitoring systems. Unique methods for non-invasive physiological monitoring are described in greater detail in relation to FIGS. 11A through 11C. Optional onboard and peripheral sensor devices for use in monitoring physiological data are described in relation to FIG. 12.

In some implementations, during an evaluation session, the individual's wearable data collection device 104 gathers counts data 116*c* related to patterns identified within other data 116. For example, the individual's data collection device 104 may count verbal (word and/or other vocalization) repetitions identified within the voice recording data 116*a* and movement repetitions identified in the head position data 116*d* and/or the motion tracking data 116*h*. The baseline analysis for identifying repetitions (e.g., time span between repeated activity, threshold number of repetitions, etc.), in some embodiments, may be tuned by educators and/or clinicians based upon baseline behavior analysis of "normal" individuals or typical behaviors indicative of individuals with a particular clinical diagnosis such as ASD. For example, verbal repetition counts 116*c* may be tuned to identify repetitive vocalizations separate from excited stuttering or other repetitive behaviors typical of children of an age or age range of the individual. In another example, movement repetition counts 116*c* may distinguish from dancing and playful repetitive behaviors of a young child. Autism assessment, progress monitoring, and coaching all are currently done with little or no support via structured, quantitative data which is one reason that rigorous counts 116*c* are so very important. Counts 116*c* can include other types of behavior such as rocking, self-hugging, self-injurious behaviors, eye movements and blink dynamics, unusually low-movement periods, unusually high-movement periods, irregular breathing and gasping, behavioral or physiological signs of seizures, irregular eating behaviors, and other repetitive or irregular behaviors.

In other implementations, rather than collecting the counts data 116*c*, a remote analysis and data management system 118 (e.g., networked server, cloud-based processing system, etc.) analyzes a portion of the session data 116 to identify at least a portion of the counts data 116*c* (e.g., verbal repetition counts and/or movement repetition counts). For example, a session data analysis engine 120 of the remote analysis and data management system 118 may analyze the voice recording data 116*a*, motion tracking data 116*h*, and/or head position data 116*d* to identify the verbal repetition counts and/or movement repetition counts.

In some implementations, the analysis is done at a later time. For example, the analysis and data management system 118 may archive the session data 116 in an archive data store 122 for later analysis. In other implementations, the session data and analysis engine 120 analyzes at least a portion of the session data 116 in real-time (e.g., through buffering the session data 116 in a buffer data store 124). For example, a real-time analysis of a portion of the session data 116 may be supplied to the evaluator 114 during the evaluation session. The real-time data analysis, for example, may be presented on the display 112 as session information and statistics information 126. In some examples, statistics information 126 includes presentation of raw data values, such as a graphical representation of heart rate or a graphical presentation of present EEG data. In other examples, statistics information 126 includes data analysis output, such as a color-coded presentation of relative excitability or stimulation of the subject (e.g., based upon analysis of a number of physiological factors) or graphic indications of identified behaviors (e.g., an icon displayed each time social eye contact is registered).

Session information and statistics information 126 can be used to perform behavioral decoding. Behavioral decoding is like language translation except that it decodes the behaviors of an individual 102 rather than verbal language utterances. For instance, a result of the session data analysis 120 might be that a pattern emerges whereby repetitive vocalizations of a particular type as well as repeated touching the cheek are correlated, in the individual 102, with ambient temperature readings below a certain temperature level, and the behaviors cease when the temperature rises. Once this pattern has been reliably measured by the system 100, upon future episodes of those behaviors, the system 100 could present to the caregiver 108 or evaluator 114 some information such as that the subject is likely too cold. The system 100 can also interface directly with control systems in the environment, for instance in this case the system 100 may turn up a thermostat to increase the ambient temperature. This example is illustrative of many possibilities for behavioral decoding. The system 100 increases in ability to do behavioral decoding the longer it interacts with the individual 102 to learn the behavioral language of the individual 102. Furthermore, the greater the total number of individuals interacting with the system 100, the greater the capacity of the system 100 to learn from normative data to identify stereotypical communication strategies of individuals within subgroups of various conditions, such as subgroups of the autism spectrum.

During an evaluation session, in an illustrative example, the caregiver 106 is tasked with performing interactive tasks with the individual 102. Video recording data 116*j* collected by the caregiver wearable data collection device 108 is supplied to a computing system of the evaluator 114 in real-time via the analysis and data management system 118 such that the evaluator 114 is able to see the individual 102 more or less "through the eyes of" the caregiver 108 during the evaluation session. The evaluator 114 may also receive voice recording data 116*a* from either the caregiver wearable data collection device 108 or the subject wearable data collection device 104.

Should the evaluator 114 wish to intercede during the evaluation session, in some implementations, the evaluator 114 can call the caregiver 106 using a telephone 128. For example, the caregiver 106 may have a cell phone or other personal phone for receiving telephone communications from the evaluator 114. In another example, the caregiver wearable computing device 108 may include a cellular communications system such that a telephone call placed by the evaluator 114 is connected to the caregiver wearable computing device 108. In this manner, for example, the caregiver 108 may receive communications from the evaluator 114 without disrupting the evaluation session.

In other implementations, a computer-aided (e.g., voice over IP, etc.) communication session is established between the evaluator 114 computing system and the caregiver wearable data collection device 108. For example, the analysis and data management system 118 may establish and coordinate a communication session between the evaluator system and the caregiver wearable data collection device 108 for the duration of the evaluation system. Example techniques for establishing communication between a wearable data collection device and a remote computing system are described in U.S. Patent Application No. 20140368980 entitled "Technical Support and Remote Functionality for a Wearable Computing System" and filed Feb. 7, 2012, the contents of which are hereby incorporated by reference in its entirety. Further, the analysis and data management system 118, in some embodiments, may collect and store voice recording data of commentary supplied by the evaluator 114.

In some examples, the evaluator 114 may communicate with the caregiver 106 to instruct the caregiver 106 to perform certain interactions with the individual 102 or to repeat certain interactions with the individual 102. Prior to or at the end of an evaluation session, furthermore, the evaluator 114 may discuss the evaluation with the caregiver 106. In this manner, the caregiver 106 may receive immediate feedback and support of the evaluator 114 from the comfort of her own home.

Figure 1B:
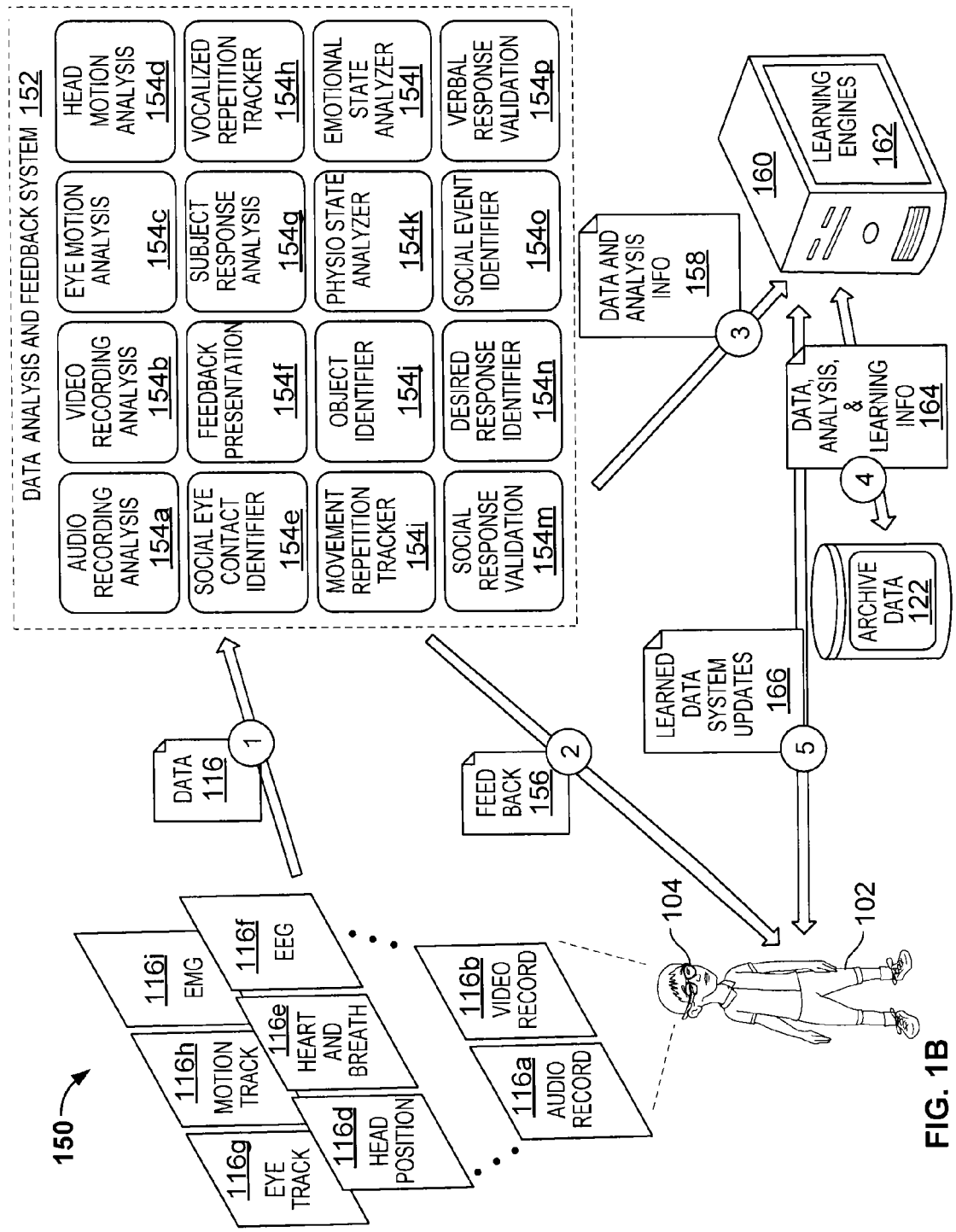
FIG. 1B is a block diagram of an example system for evaluation and training of an individual using a wearable data collection device.

FIG. 1B is a block diagram of an example system 150 for evaluation and training of the individual 102 using the wearable data collection device 104. Data 116 collected by the wearable data collection device 104 (and, optionally or alternatively, data collected by the caregiver data collection device 108 described in relation to FIG. 1A) is used by a number of algorithms 154 developed to analyze the data 116 and determine feedback 156 to provide to the individual 102 (e.g., via the wearable data collection device 104 or another computing device). Furthermore, additional algorithms 532, 534, 536, 538, 540, 542, and 544 described in relation to FIG. 5B and/or algorithms 910 and 912 described in relation to FIG. 9 may take advantage of components of the system 150 in execution. The algorithms 154 may further generate analysis information 158 to supply, along with at least a portion of the data 116, to learning engines 162. The analysis information 158 and data 116, along with learning information 164 generated by the learning engines 162, may be archived as archive data 122 for future use, such as for pooled statistical learning. The learning engines 162, furthermore, may provide learned data 166 and, potentially, other system updates for use by the wearable data collection device 104. The learned data 166, for example, may be used by one or more of the algorithms 154 residing upon the wearable data collection device 104. A portion or all of the data analysis and feedback system 152, for example, may execute upon the wearable data collection device 104. Conversely, in some implementations, a portion or all of the data analysis and feedback system 152 is external to the wearable data collection device 104. For example, certain algorithms 154 may reside upon a computing device in communication with the wearable data collection device 104, such as a smart phone, smart watch, tablet computer, or other personal computing device in the vicinity of the individual 102 (e.g., belonging to a caregiver, owned by the individual 102, etc.). Certain algorithms 154, in another example, may reside upon a computing system accessible to the wearable data collection device 104 via a network connection, such as a cloud-based processing system.

The algorithms 154 represent a sampling of potential algorithms available to the wearable data collection device 104 (and/or the caregiver wearable data collection device 108 as described in relation to FIG. 1A). The algorithms 154 include an audio recording analysis algorithm 154*a*, a video recording analysis algorithm 154*b*, an eye motion analysis algorithm 154*c*, a head motion analysis algorithm 154*d*, a social eye contact identifying algorithm 154*e*, a feedback presentation algorithm 154*f*, a subject response analysis algorithm 154*g*, a vocalized repetition tracking algorithm 154*h* (e.g., to generate a portion of the counts data 116*c* illustrated in FIG. 1A), a movement repetition tracking algorithm 154*i* (e.g., to generate a portion of the counts data 116*c* illustrated in FIG. 1A), an object identification algorithm 154*j*, a physiological state analysis algorithm 154*k*, an emotional state analysis algorithm 154*l*, a social response validation algorithm 154*m*, a desired response identification algorithm 154*n*, a social event identification algorithm 154*o*, and a verbal response validation engine 154*p*. Versions of one or more of the algorithms 154 may vary based upon whether they are executed upon the individual's wearable data collection device 104 or the caregiver wearable data collection device 108. For example, the social eye contact identification algorithm 154*e* may differ when interpreting video recording data 116*b* supplied from the viewpoint of the individual 102 as compared to video recording data 116*b* supplied from the viewpoint of the caregiver 106 (illustrated in FIG. 1A).

The algorithms 154 represent various algorithms used in performing various methods described herein. For example, method 600 regarding identifying objects labeled with standardized index elements (described in relation to FIG. 6A) and/or method 610 regarding extracting information from objects with standardized index elements (described in relation to FIG. 6B), may be performed by the object identification algorithm 154*j*. Step 662 of method 630 (described in relation to FIG. 6D) regarding validating the subject's response may be performed by the verbal response validation algorithm 154*p*. Step 664 of method 630 (described in relation to FIG. 6D) regarding providing feedback regarding the subject's response may be performed by the feedback presentation algorithm 154*f*. Step 704 of method 700 regarding detection of a socially relevant event, described in relation to FIG. 7A, may be performed by the social event identification algorithm 154*o*. Step 716 of method 700 regarding determination of a desired response to a socially relevant event may be performed by the desired response identification algorithm 154n. Step 718 of method 700 regarding comparison of the subject's actual response may be performed by the social response validation algorithm 154m. Step 740 of method 700 regarding reviewing physiological data, described in relation to FIG. 7B, may be performed by the physiological state analysis algorithm 154k. Step 802 of method 800 regarding identification of faces in video data, described in relation to FIG. 8, may be performed by the video recording analysis algorithm 154b. Step 810 of method 800 regarding identification of social eye contact may be performed by the social eye contact identification algorithm 154e. The social eye contact identification algorithm 154e, in turn, may utilize the eye motion analysis engine 154c and/or the head motion analysis engine 154d in identifying instances of social eye contact between the individual 102 and another individual. Step 816 of method 800 regarding ascertaining an individual's reaction to feedback may be performed by the subject response analysis algorithm 154g. Step 1006 of method 1000 regarding identifying an emotional state of an individual, described in relation to FIG. 10A, may be performed by the emotional state analysis algorithm 154l. Step 1010 of method 1000 regarding analyzing audio data for emotional cues may be performed by the audio recording analysis algorithm 154a.

Figure 3A:
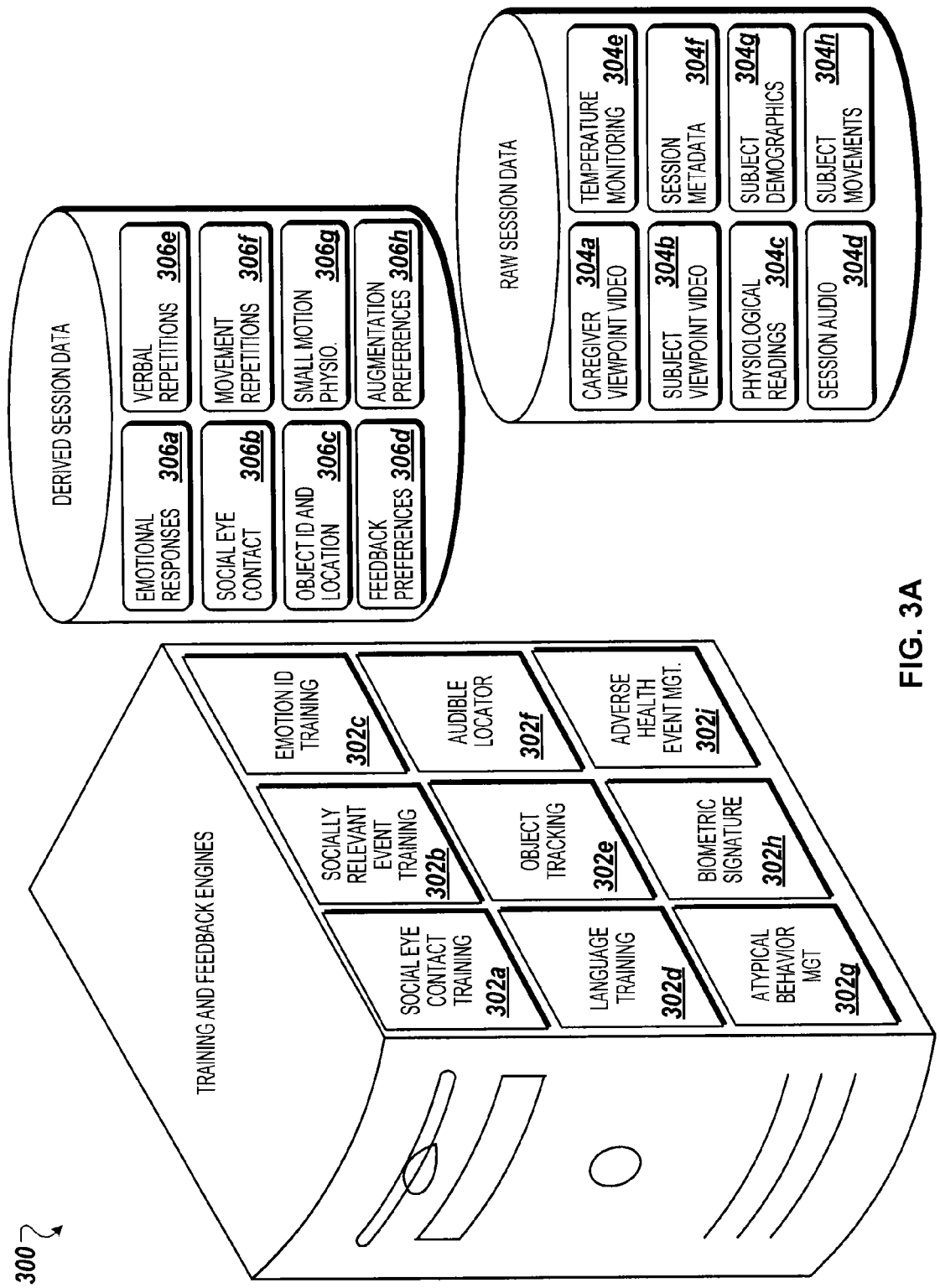
FIG. 3A is a block diagram of an example computing system for training and feedback software modules incorporating data derived by a wearable data collection device.

The algorithms 154, in some implementations, are utilized by various software modules 302 described in relation to FIG. 3A. For example, a social eye contact training module 302a may utilize the social eye contact identification algorithm 154e. A socially relevant event training module 302b, in another example, may utilize the social response validation algorithm 154m, the desired response identification algorithm 154n, and/or the social event identification algorithm 154o.

The algorithms 154, in some implementations generate analysis information 158 such as, for example, the derived session data 306 illustrated in FIG. 3A. The analysis information 158 may be provided in real time and/or in batch mode to a learning and statistical analysis system 160 including the learning engines 162. The learning engines 162, for example, may include the statistical analysis software modules 352 illustrated in FIG. 3B. A portion of the statistical analysis system 160 may execute upon the wearable data collection device 104. Conversely, in some implementations, a portion or all of the statistical analysis system 160 is external to the wearable data collection device 104. For example, certain learning engines 162 may reside upon a computing device in communication with the wearable data collection device 104, such as a smart phone, smart watch, tablet computer, or other personal computing device in the vicinity of the individual 102 (e.g., belonging to a caregiver, owned by the individual 102, etc.). The statistical analysis system 160, in another example, may reside upon a computing system accessible to the wearable data collection device 104 via a network connection, such as a cloud-based processing system.

Figure 3B:
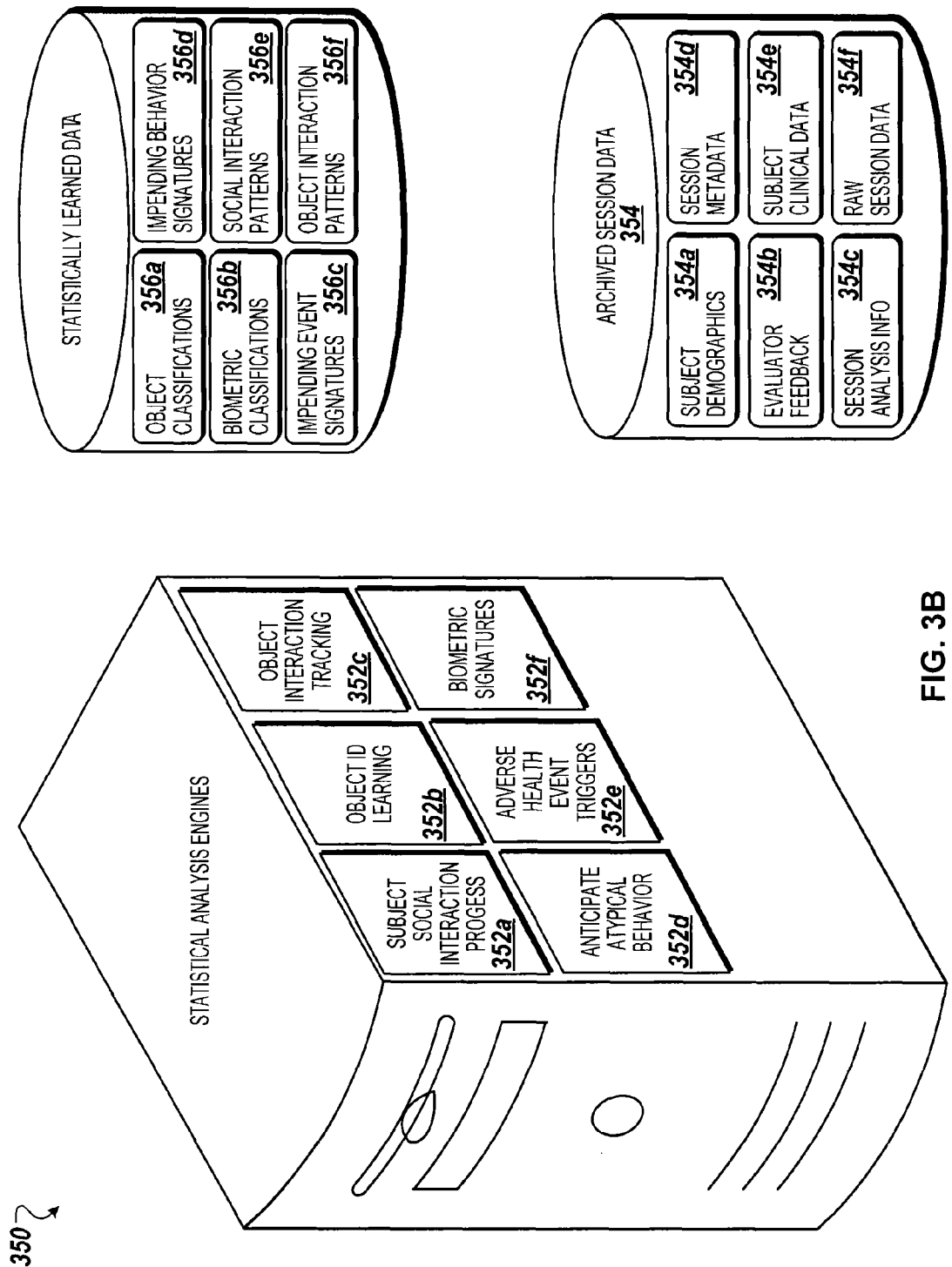
FIG. 3B is a block diagram of an example computing system for analyzing and statistically learning from data collected through wearable data collection devices.

The learning engines 162, in some implementations, generate learning information 164. For example, as illustrated in FIG. 3B, statistically learned data 356 may include social interaction patterns 356e. The learning engines 162 may execute a subject social interaction progress software module 352a to track progress of interactions of the individual 102 with the caregiver 106. Further, statistically learned data 356, in some implementations, may lead to system updates 166 presented to improve and refine the performance of the wearable data collection device 104.

Statistically learned data 356, in some implementations, can be used to predict acting out or episodes in people with ASD. In some implementations, statistically learned data 356 can be used to predict, based on current conditions and environmental features as well as physiological or behavioral signals from the subject, unwellness or health episodes such as seizures or migraine onset or heart attacks or other cardiovascular episodes, or other outcomes such as are related to ASD. Statistically learned data 356 can be used to provide behavioral decoding. For instance, statistically learned data 356 may indicate that one type of self-hitting behavior plus a specific vocalization occurs in an individual 102 most frequently before meal times, and these behaviors are most pronounced if a meal is delayed relative to a regular meal time, and that they are extinguished as soon as a meal is provided and prevented if snacks are given before a regular meal. In this context, these behaviors may be statistically associated with hunger. The prior example is simplistic in nature—a benefit of computer-based statistical learning is that the statistical learning data 356 can allow the system to recognize patterns that are less obvious than this illustrative example. In the present example, at future times, statistical learning data 356 that resulted in recognition of a pattern such as mentioned can provide for behavioral decoding such as recognizing the behaviors as an indicator that the individual 102 is likely hungry.

Behavioral decoding can be used for feedback and/or for intervention. For instance, in terms of feedback, the system, in some implementations, provides visual, textual, auditory or other feedback to the individual 102, caregiver 106, and/or evaluator 114 (e.g., feedback identifying that the individual 102 is likely hungry). Behavioral decoding can also be used for intervention. For instance, in this case, when the aforementioned behaviors start emerging, a control signal can be sent from the system 100 to trigger in intervention that will reduce hunger, such as in this case ordering of food or instruction to the caregiver to provide food.

Figure 2A:
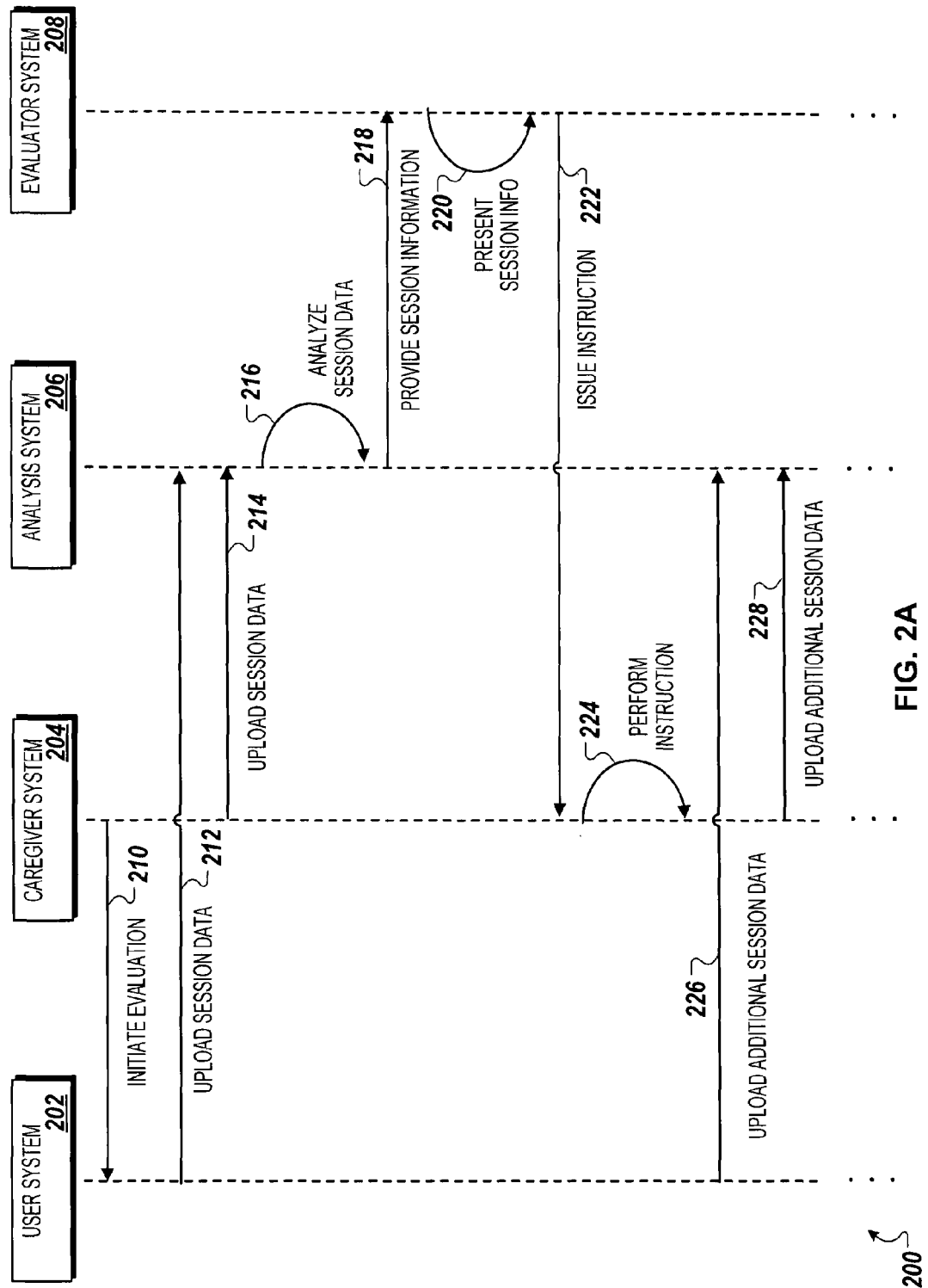
FIGS. 2A and 2B are a swim lane diagram of an example method for performing a remote evaluation of an individual using a wearable data collection device.
Figure 2B:
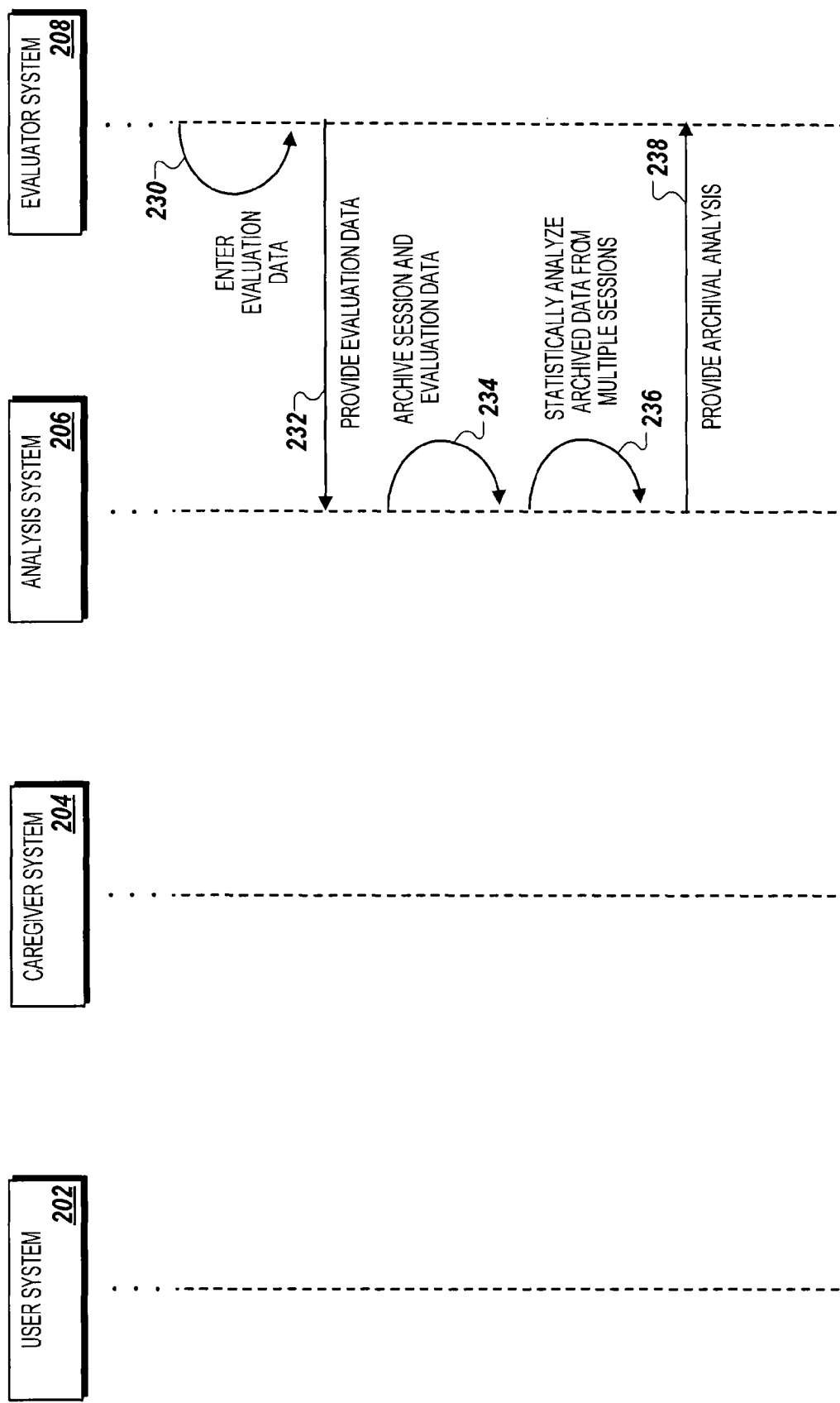

Turning to FIGS. 2A and 2B, a swim lane diagram illustrates a method 200 for conducting an evaluation session through a caregiver system 204 and a user system 202 monitored by an evaluator system 208. Information passed between the evaluator system 208 and either the caregiver system 204 or the user system 202 is managed by an analysis system 206. The caregiver system 204 and/or the user system 202 include a wearable data collection device, such as the wearable data collection devices 104 and 108 described in relation to FIG. 1A. The evaluation system 208 includes a computing system and display for presentation of information collected by the wearable data collection device(s) to an evaluator, such as the evaluator 114 described in relation to FIG. 1A. The analysis system 206 includes a data archival system such as the data buffer 128 and/or the data archive 122 described in relation to FIG. 1A, as well as an analysis module, such as the session data analysis engine 120 described in relation to FIG. 1A.

In some implementations, the method 200 begins with initiating an evaluation session (210) between the caregiver system 204 and the user system 202. An evaluator may have defined parameters regarding the evaluation session, such as a length of time, activities to include within the evaluation session, and props or objects to engage with during the evaluation session. In initiating the evaluation session, a software application functioning on the caregiver system 204 may communicate with a software application on the user system 202 to coordinate timing and initialize any data sharing parameters for the evaluation session. For example, information may be shared between the caregiver system 204 and the user system 202 using techniques described in U.S. Pat. No. 8,184,983 entitled "Wireless Directional Identification and Subsequent Communication Between Wearable Electronic Devices" and filed Jun. 9, 2011, the contents of which are hereby incorporated by reference in its entirety. In a particular example, the caregiver system 204 may issue a remote control "trigger" to the user system 202 (e.g., wearable data collection device) to initiate data collection by the user system 202. Meanwhile, the caregiver system 204 may initiate data collection locally (e.g., audio and/or video recording).

In some implementations, initiating the evaluation session further includes opening a real-time communication channel with the evaluator system 208. For example, the real-time evaluation session may be open between the caregiver system 204 and the evaluator system 208 and/or the user system 202 and the evaluator system 208. In some implementations, the caregiver system 204 initiates the evaluation session based upon an initiation trigger supplied by the evaluator system 208.

In some implementations, session data is uploaded (212) from the user system 202 to the analysis system 206. For example, data collected by one or more modules functioning upon the user system 202, such as a video collection module and an audio collection module, may be passed from the subject system 202 to the analysis system 206. The data, in some embodiments, is streamed in real-time. In other embodiments, the data is supplied at set intervals, such as, in some examples, after a threshold quantity of data has been collected, after a particular phase of the session has been completed, or upon pausing an ongoing evaluation session. The data, in further examples, can include eye tracking data, motion tracking data, EMG data, EEG data, heart rate data, breathing rate data, and data regarding subject repetitions (e.g., repetitive motions and/or vocalizations).

Furthermore, in some implementations, session data is uploaded (214) from the caregiver system 204 to the analysis system 206. For example, audio data and/or video data collected by a wearable data collection device worn by the caregiver may be uploaded to the analysis system 206. Similar to the upload from the subject system 202 and the analysis system 206, data upload from the caregiver system 204 to the analysis system 206 may be done in real time, periodically, or based upon one or more triggering events.

In some implementations, the analysis system 206 analyzes (216) the session data. Data analysis can include, in some examples, identifying instances of social eye contact between the individual and the caregiver, identifying emotional words, and identifying vocalization of the subject's name. The analysis system 206, in some embodiments, determines counts of movement repetitions and/or verbal repetitions during recording of the individual's behavior. Further, in some embodiments, data analysis includes deriving emotional state of the individual from one or more behavioral and/or physiological cues (e.g., verbal, body language, EEG, EMG, heart rate, breathing rate, etc.). For example, the analysis system 206 may analyze the reaction and/or emotional state of the individual to the vocalization of her name. The analysis system 206, in some embodiments, further analyzes caregiver reactions to identified behaviors of the individual such as, in some examples, social eye contact, repetitive behaviors, and vocalizations. For example, the analysis system 206 may analyze body language, emotional words, and/or vocalization tone derived from audio and/or video data to determine caregiver response.

In some implementations, analyzing the session data (216) includes formatting session data into presentation data for the evaluator system 208. For example, the analysis system 206 may process heart rate data received from the user system 202 to identify and color code instances of elevated heart rate, as well as preparing presentation of the heart rate data in graphic format for presentation to the evaluator. If prepare in real time, the session data supplied by the user system 202 and/or the caregiver system 204 may be time delayed such that raw session information (e.g., video feed) may be presented to the evaluator simultaneously with processed data feed (e.g., heart rate graph).

The analysis system 206, in some implementations, archives at least a portion of the session data. For example, the session data may be archived for review by an evaluator at a later time. In another example, archived system data may be analyzed in relation to session data derived from a number of additional subjects to derived learned statistical data (described in greater detail in relation to FIG. 3B).

In some implementations, the analysis system 206 provides (218) session information, including raw session data and/or processed session data, to the evaluator system 208. At least a portion of the session data collected from the user system 202 and/or the caregiver system 204, in one example, is supplied in real time or near-real time to the evaluator system 208. As described above, the session information may include enhanced processed session data prepared for graphical presentation to the evaluator. In another example, the evaluator system 208 may request the session information from the analysis system 206 at a later time. For example, the evaluator may review the session after the individual and caregiver have completed and authorized upload of the session to the analysis system. In this manner, the evaluator may review session data at leisure without needing to coordinate scheduling with the caregiver.

In some implementations, if the evaluator is reviewing the session information in near-real-time, the evaluator system 208 issues (222) an instruction to the caregiver system 204. The evaluator, for example, may provide verbal instructions via a telephone call to the caregiver system 204 or an audio communication session between the evaluator system 208 and the caregiver system 204. For example, a voice data session may be established between the evaluator system 208 and the caregiver's wearable data collection device. In another example, the evaluator system 208 may supply written instructions or a graphic cue to the caregiver system 204. In a particular example, a graphic cue may be presented upon a heads-up display of the caregiver's wearable data collection device (such as the heads up display described in U.S. Pat. No. 8,203,502 entitled "Wearable Heads-Up Display with Integrated Finger-Tracking Input Sensor" and filed May 25, 2011, the contents of which are hereby incorporated by reference in its entirety) to prompt the caregiver to interact with the individual using a particular object.

Rather than issuing an instruction, in some implementations the evaluator system 208 takes partial control of either the caregiver system 204 or the user system 202. In some examples, the evaluator system 208 may assert control to speak through the user system 202 to the individual or to adjust present settings of the wearable data collection device of the caregiver. In taking partial control of the caregiver system 204 or the user system 202, the evaluator system 208 may communicate directly with either the caregiver system 204 or the user system 202 rather than via the relay of the analysis system 206.

Similarly, although the instruction, as illustrated, bypasses the analysis system 206, the communication session between the evaluator system 208 and the caregiver system 204, in some implementations, is established by the analysis system 206. The analysis system 206, in some embodiments, may collect and archive a copy of any communications supplied to the caregiver system 204 by the evaluator system 208.

In some implementations, the caregiver system 204 performs (224) the instruction. For example, the instruction may initiate collection of additional data and/or real-time supply of additional data from one of the caregiver system 204 and the subject system 202 to the evaluator system 208 (e.g., via the analysis system 206). The evaluator system 208, in another example, may cue a next phase on the evaluation session by presenting instructional information to the caregiver via the caregiver system 204. For example, upon cue by the evaluator system 208, the caregiver system 204 may access and present instructions for performing the next phase of the evaluation session by presenting graphical and/or audio information to the caregiver via the wearable data collection device.

In some implementations, the user system 202 uploads (226) additional session data and the caregiver system 204 uploads (228) additional session data. The data upload process may continue throughout the evaluation session, as described, for example, in relation to steps 212 and steps 214.

Turning to FIG. 2B, in some implementations, the evaluator enters (230) evaluation data via the evaluator system 208. For example, the evaluator may include comments, characterizations, caregiver feedback, and/or recommendations regarding the session information reviewed by the evaluator via the evaluator system 208.

In some implementations, the evaluator system 208 provides (232) the evaluation data to the analysis system 206. The evaluation data, for example, may be archived along with the session data. At least a portion of the evaluation data, furthermore, may be supplied from the analysis system 206 to the caregiver system 204, for example as immediate feedback to the caregiver. In some embodiments, a portion of the evaluation data includes standardized criteria, such that the session data may be compared to session data of other individuals characterized in a same or similar manner during evaluation.

In some implementations, the analysis system 206 archives (234) the session and evaluation data. For example, the session and evaluation data may be uploaded to long term storage in a server farm or cloud storage area. Archival of the session data and evaluation data, for example, allows data availability for further review and/or analysis. The session data and evaluation data may be anonymized, secured, or otherwise protected from misuse prior to archival.

In some implementations, the analysis system 206 statistically analyzes (236) the archived data from multiple sessions. In one example, archived session data may be compared to subsequent session data to reinforce characterizations or to track progress of the individual. In another example, as described above, the session data may be evaluated in relation to session data obtained from further individuals to derive learning statistics regarding similarly characterized individuals. The evaluation data supplied by the evaluator in step 230, in one example, may include an indication of desired analysis of the session data. For example, the session data may be compared to session data collected during evaluation of a sibling of the subject on a prior occasion.

In some implementations, the analysis system 206 provides (238) analysis information derived from the archived session data to the evaluator system 208. For example, upon analyzing the session data in view of prior session data with the same individual, progress data may be supplied to the evaluator system 208 for review by the evaluator.

FIG. 3A is a block diagram of a computing system 300 for training and feedback software modules 302 for execution in relation to a wearable data collection device. The training and feedback software modules 302 incorporate various raw session data 304 obtained by a wearable data collection device, and generate various derived session data 306. The training and feedback software modules 302, for example, may include software modules capable of executing on any one of the subject wearable data collection device 104, the caregiver wearable data collection device 108, and the analysis and data management system 118 of FIG. 1A. Further, at least a portion of the training and feedback software modules 302 may be employed in a system 500 of FIG. 5A, for example in a wearable data collection device 504 and/or a learning data analysis system 520, or in a system 1100 of the FIG. 11A, for example in a wearable data collection device 1104 and/or a learning data analysis system 1118. The raw session data 304, for example, may represent the type of session data shared between the subject system 202 or the caregiver system 204 and the analysis system 206, as described in relation to FIG. 2A.

FIG. 3B is a block diagram of a computing system 350 for analyzing and statistically learning from data collected through wearable data collection devices. The archived session data 354 may include data stored as archive data 122 as described in FIG. 1A and/or data stored as archive data 1122 as described in FIG. 11A. For example, the analysis system 206 of FIG. 2B, when statistically analyzing the archived data in step 236, may perform one or more of the statistical analysis software modules 352 upon a portion of the archived session data 354.

Figure 4:
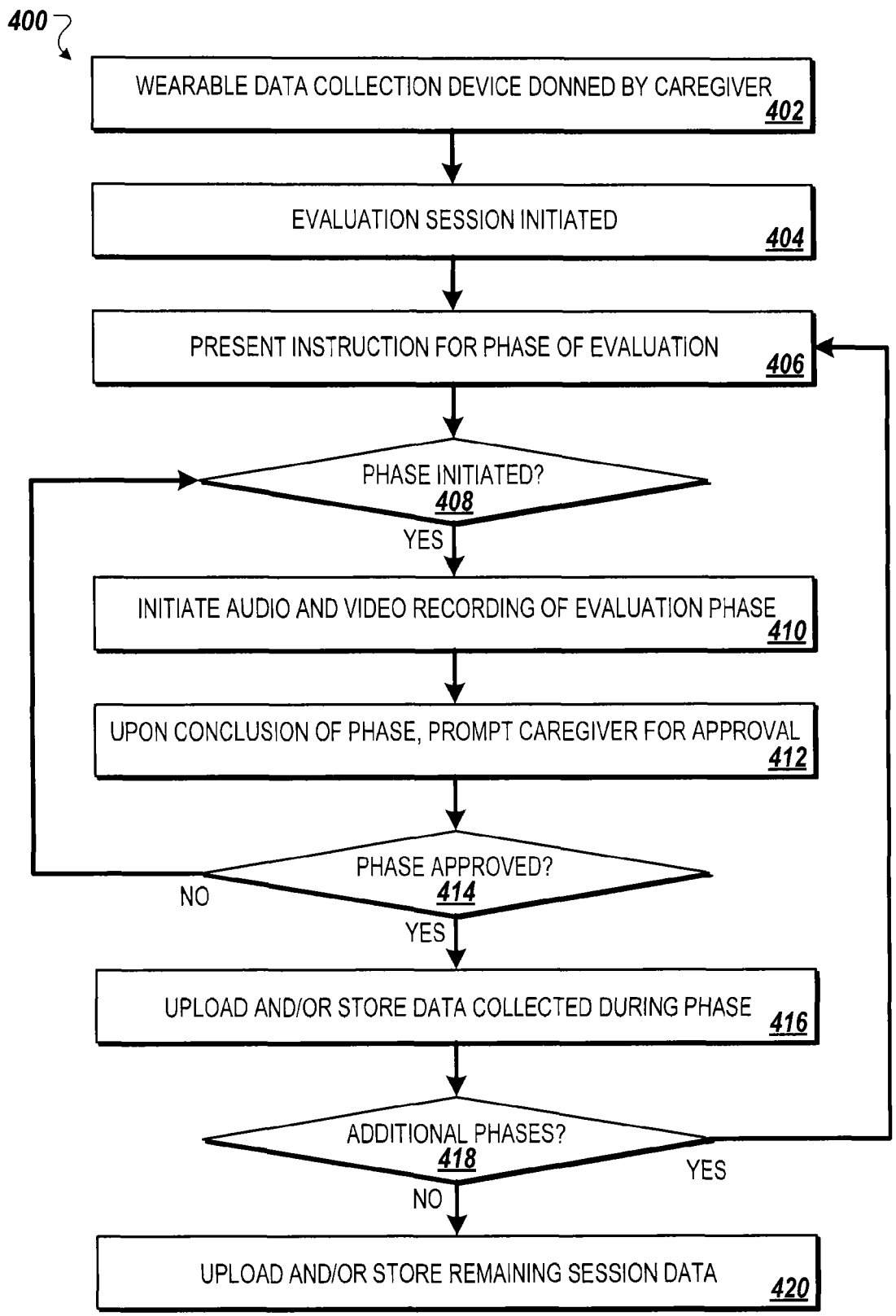
FIG. 4 is a flow chart of an example method for conducting an evaluation session using a wearable data collection device donned by a caregiver of an individual being evaluated for Autism Spectrum Disorder.

FIG. 4 is a flow chart of an example method 400 for conducting an evaluation session using a wearable data collection device donned by a caregiver of an individual being evaluated for Autism Spectrum Disorder. The method 400, for example, may be performed independent of an evaluator in the comfort of the caregiver's home. The caregiver may be supplied with a kit including a wearable data collection device and instructions for performing an evaluation session. The kit may optionally include a wearable data collection device for the individual.

In some implementations, the method 400 begins with the caregiver donning the wearable data collection device (402). Examples of a wearable data collection device are described in relation to FIG. 1A. The wearable data collection device, for example, may include a head-mounted lens for a video recording system, a microphone for audio recording, and a head-mounted display. Further, the wearable data collection device may include a storage medium for storing data collected during the evaluation session.

In some implementations, the evaluation session is initiated (404). Upon powering and donning the wearable data collection device, or launching an evaluation session application, the evaluation session may be initiated. Initiation of the evaluation session may include, in some embodiments, establishment of a communication channel between the wearable data communication device and a remote computing system.

In some implementations, instructions are presented for a first phase of evaluation (406). The instructions may be in textual, video, and/or audio format. Instructions, for example, may be presented upon a heads-up display of the wearable data collection device. If a communication channel was established with the remote computing system, the instructions may be relayed to the wearable data communication device from the remote computing system. In other embodiments, the instructions may be programmed into the wearable data communication device. The evaluation kit, for example, may be preprogrammed to direct the caregiver through an evaluation session tailored for a particular individual (e.g., first evaluation of a 3-year-old male lacking verbal communication skills versus follow-on evaluation of a 8-year-old female performing academically at grade level). In another example, the caregiver may be prompted for information related to the individual, and a session style may be selected based upon demographic and developmental information provided. In other implementations, rather than presenting instructions, the caregiver may be prompted to review a booklet or separate video to familiarize himself with the instructions.

The evaluation session, in some implementations, is performed as a series of stages. Each stage for example, may include one or more activities geared towards encouraging interaction between the caregiver and the individual. After reviewing the instructions, the caregiver may be prompted to initiate the first phase of evaluation. If the phase is initiated, in some implementations, audio and video recording of the evaluation phase is initiated (410). The wearable data collection device, for example, may proceed to collect data related to the identified session.

In some implementations, upon conclusion of the phase, the caregiver is prompted for approval (412). The caregiver may be provided the opportunity to approve the phase of evaluation, for example, based upon whether the phase was successfully completed. A phase may have failed to complete successfully, in some examples, due to unpredicted interruption (e.g., visitor arriving at the home, child running from the room and refusing to participate, etc.).

In some implementations, if the phase has not been approved (414), the phase may be repeated by re-initiating the current phase (408) and repeating collection of audio and video recording (410). In this manner, if the evaluation session phase is interrupted or otherwise failed to run to completion, the caregiver may re-try a particular evaluation phase.

Upon approval by the caregiver of the present phase (414), in some implementations, session data associated with the particular phase is stored and/or uploaded (416). The data, for example, may be maintained in a local storage medium by the wearable data collection device or uploaded to the remote computing system. Metadata, such as a session identifier, phase identifier, subject identifier, and timestamp, may be associated with the collected data. In some implementations, for storage or transfer, the wearable data collection device secures the data using one or more security algorithms to protect the data from unauthorized review.

In some implementations, if additional phases of the session exist (418), instructions for a next phase of the evaluation are presented (406). As described above in relation to step 406, for example, the wearable data collection device may present instructions for caregiver review or prompt the caregiver to review separate instructions related to the next phase.

In some implementations, at the end of each phase, the caregiver may be provided the opportunity to suspend a session, for example to allow the individual to take a break or to tend to some other activity prior to continuing the evaluation session. In other implementations, the caregiver is encouraged to proceed with the evaluation session, for example to allow an evaluator later to review the individual's responses as phase activities are compounded.

If no additional phases exist in the evaluation session (418), in some implementations, remaining session data is uploaded or stored (420) as described in step 416. If the phase data was previously stored locally on the wearable data collection device, at this point, the entire session data may be uploaded to the remote computing system. In other embodiments, the session data remains stored on the wearable data collection device, and the wearable data collection device may be returned for evaluation and reuse purposes. In addition to the session data, the caregiver may be prompted to provide additional data regarding the session, such as a session feedback survey or comments regarding the individual's participation in the evaluation session compared to the individual's typical at-home behaviors. This information may be uploaded or stored along with the data collected for each evaluation phase.

Figure 5A:
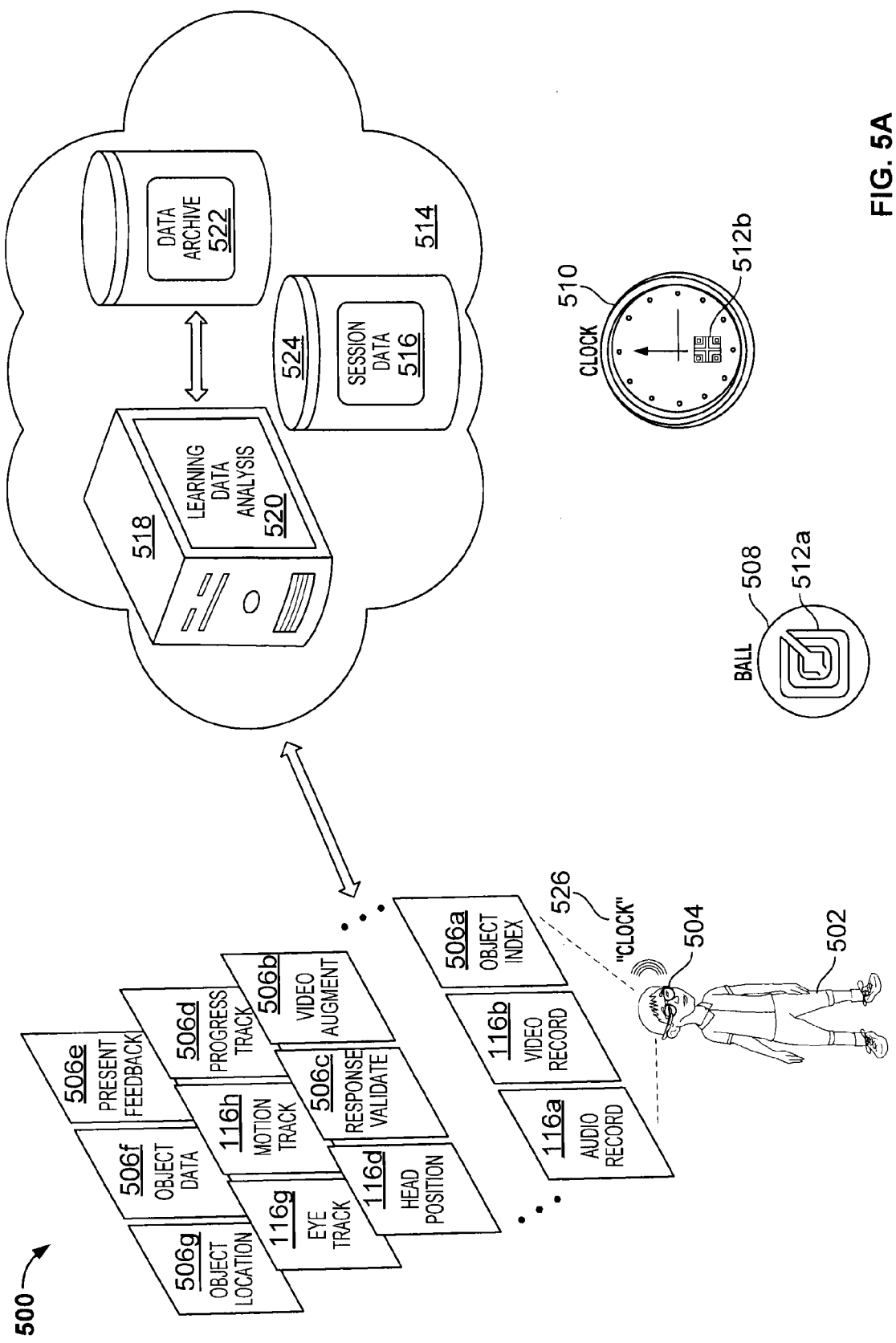
FIG. 5A is a block diagram of an example environment for augmented reality learning using a wearable data collection device.

FIG. 5A is a block diagram of an example environment 500 for augmented reality learning, coaching, and assessment using a wearable data collection device 504. As illustrated, the wearable data collection device 504 shares many of the same data collection features 116 as the wearable data collection devices 104 and 108 described in relation to FIG. 1A. Additionally, the wearable data collection device includes data collection and interpretation features 506 configured generally for identifying objects and individuals within a vicinity of an individual 502 and for prompting, coaching, or assessing interactions between the individual 502 and those objects and individuals within the vicinity.

In some implementations, the example environment includes a remote analysis system 514 for analyzing the data 116 and/or 506 using one or more learning data analysis modules 520 executing upon a processing system 518 (e.g., one or more computing devices or other processing circuitry). The learning data analysis module(s) 520 may store raw and/or analyzed data 116, 506 as session data 516 in a data store 524. Further, the remote analysis system 514 may archive collected data 116 and/or 506 in a data archive 522 for later analysis or for crowd-sourced sharing to support learning engines to enhance performance of the learning data analysis modules 520.

Figure 5B:
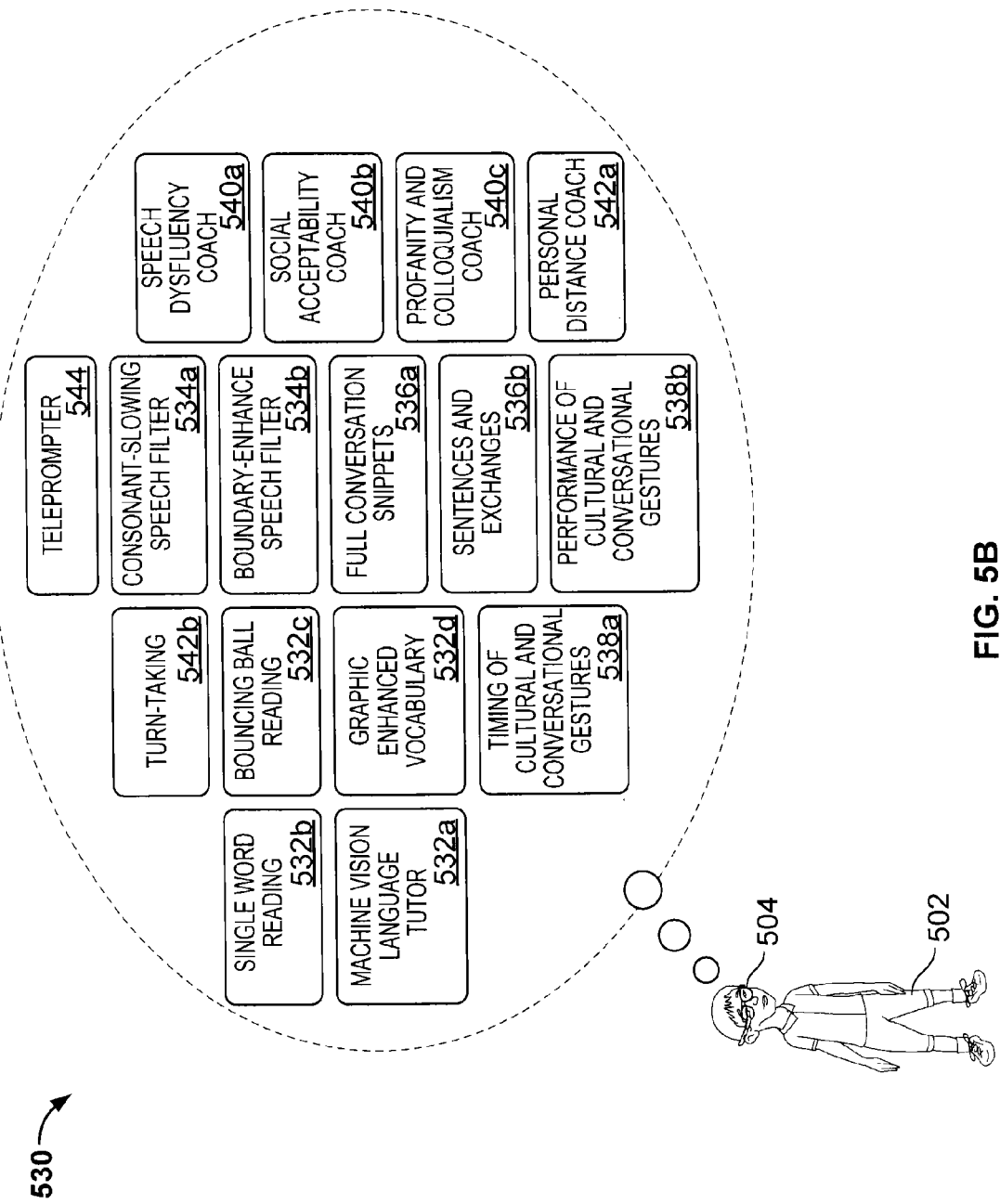
FIG. 5B is a block diagram of an example collection of software algorithms or modules for implementing language and communication skill training, assessment, and coaching using a wearable data collection device.

In addition to or in replacement of the learning data analysis module(s) 520, in some implementations, the processing system 518 includes one or more language and communication algorithms 530 (e.g., software, firmware, and/or hardware-based computing algorithms designed to assess, train, and coach the individual 502 in language and communication skills), illustrated in FIG. 5B. Rather than residing in the remote analysis system 514, in some implementations, one or more of the algorithms 530 (or feature portions thereof) are executed upon the wearable data collection device and/or on a peripheral computing device in communication with the wearable data collection device.

Turning to FIG. 5B, the language and communication algorithms 530 include a set of reading tools 532, a set of speech-filtering tools 534, a set of conversational tools 536, a set of communicative gesture tools 538, a set of speech coaching tools 540, a set of interpersonal communication tools 542, and a teleprompter algorithm 544. Although each set of tools 532-542 includes individual topic algorithms, in other implementations, one or more of the algorithms 532-542 may be combined. Additionally, a particular algorithm 532-544 may be divided into two or more algorithm modules. The algorithms 532-544, together, provide a language tool set configured to support reading, linguistics, interpersonal communications, and speech understanding.

Beginning with the reading tools 532, a machine vision language tutor algorithm 532a, in some implementations, supports recognition and learning modules incorporating machine-encoded objects within the vicinity of the individual 502. Turning to FIG. 5A, the machine vision language tutor algorithm 532a may include, for example, the ability to identify encoded objects within the vicinity of the wearable data collection device 504. For example, the machine vision language tutor algorithm 532a may scan the immediate vicinity of the individual 502 wearing the wearable data collection device 504 to identify objects encoded with standardized index elements 512, such as, in some examples, a two-dimensional barcode, three-dimensional barcode, QR code, radio-frequency identification (RFID) tags, and other machine-readable labels or electronically transmitting smart labels. As illustrated, a ball object 508 includes an RFID tag element 512a and a clock object 510 includes a QR code element 512b. Each standardized index element 512, in turn, may be encoded with or otherwise identify a unique object index 506a. In one example, the machine vision language tutor algorithm 532a, executing upon the wearable data collection device 504 or a computing device in communication with the wearable data collection device (e.g., the processing system 518 or a local computing device such as a smart phone, tablet computer, etc.) 504 may use one or more hardware, firmware, or software elements of the wearable data collection device to scan the immediate vicinity to collect object indices 506a associated with each encoded object 508, 510. In a particular example, the machine vision language tutor algorithm 532a may use an RFID scanner feature of the wearable data collection device 504 to scan the vicinity to identify the RFID tag 512a. In another example, the machine vision language tutor algorithm 532a may analyze video recording data 116b captured by the wearable data collection device 504 or a computing system in communication with the wearable data collection device 504 to identify the standardized index elements 512 (e.g., QR codes or bar codes). In other examples, the machine vision language tutor algorithm 532a uses machine-vision processes, machine-hearing, or other signal processing abilities of the wearable data collection device 504 to identify objects with standardized index elements in the vicinity. To improve recognition of objects encoded with standardized index elements within the vicinity, in some embodiments, the machine vision language tutor algorithm 532a may use two or more separate methods of identifying items. The machine vision language tutor algorithm 532a may cross-reference the objects identified using a first recognition method, for example, with the objects identified using a second recognition method.

In some implementations, each standardized index element 512 is embedded with a particular identifier (e.g., substring) that is otherwise unlikely to occur in that particular type of index element, such that the identifier can be used to identify standardized index elements created for use with the wearable data collection device 504. For example, while scanning the vicinity for standardized index elements, the machine vision language tutor algorithm 532a can ignore those labels (e.g., QR codes, RFID tags) lacking the identifier.

In some implementations, the machine vision language tutor algorithm 532a matches object data 506f to each object index 506a. For example, the machine vision language tutor algorithm 532a may apply the object index 506a to a look-up table to derive associated object data 506f regarding the encoded object. In the event that the object data 506f accessed depends upon a particular functional mode of the machine vision language tutor algorithm 532a and/or the wearable data collection device 504, the machine vision language tutor algorithm 532a may access a mode-specific look-up table to derive associated object data 506f. In another example, the machine vision language tutor algorithm 532a may access a database to derive multiple representations of a particular data group, for example object data 506f including terms for an item in a number of foreign languages. In another example, a smart label such as an RFID tag may include embedded object data 506f which can be read by the machine vision language tutor algorithm 532a.

The machine vision language tutor algorithm 532a, in some implementations, presents a portion of the derived object data 506f to the individual 502. For example, video augmentation data 506b may be used by a video augmentation module of the machine vision language tutor algorithm 532a to portray the names of each object in a display region of the wearable data collection device 504 as written words floating above or upon each object. In another example, the machine vision language tutor algorithm 532a may cause the names of each object may be intoned audibly to the individual 502, for example through a sound system of the wearable data collection device 504 that includes a headphone or bone-conduction speaker such as the bone-conduction speaker described in U.S. Patent Application No. 20140016800 entitled "Wearable Computing Device with Behind-Ear Bone-Conduction Speaker" and filed Jan. 16, 2014, the contents of which is hereby incorporated by reference in its entirety. In further examples, the machine vision language tutor algorithm 532a may present derived object data 506f associated with the object to the individual 502, such as a tick-tock and/or chiming sound associated with a clock.

In some implementations, prior to presenting any object data 506f related to the acquired object indices 506a, the individual 502 may first select a desired object. Selection, in some examples, may be accomplished via a hand gesture, head gesture, eye movement (e.g., double blink), audible command, thought pattern, or other instruction issued by the individual 502 via an input system of the wearable data collection device 504. Upon selection of one of the objects 508, 510, for example, the video augmentation module of the machine vision language tutor algorithm 532a may present the individual 502 with an augmented video representation of the field of vision, including object data 506f regarding the selected object 508. In another example, an audio feedback module of the machine vision language tutor algorithm 532a may play audible object data 506f regarding the selected object 508, 510.

In some implementations, selection of an object triggers a deep information retrieval module of the machine vision language tutor algorithm 532a. For example, in the context of a chemistry lab, initial object data 506f may include the name of a chemical compound, while a second (deeper) level of object data 506f may include a chemistry information sheet regarding the specific compound. Rather than presenting the deeper level object data 506f via the wearable data collection device 504, in some embodiments the machine vision language tutor algorithm 532a may redirect the deeper level object data 506f to a separate computing device, such as, in some examples, a smart phone, tablet computer, laptop computer, or smart television. The wearable data collection device 504, in some embodiments, shares the object data 506f with the separate computing device through a wireless communications link, such as a Wi-Fi or Bluetooth connection.

The type and style of presentation of object data 506*f*, in some implementations, depends upon a mode of operation of the wearable data collection device 504 or the machine vision language tutor algorithm 532*a*, potentially involving one or more additional software modules or algorithms currently active upon the wearable data collection device 504. The mode may in part represent a level of complexity of vocabulary, such as a grade level or reading achievement level. Other mode granulations, in some examples, may include picture presentation versus word presentation, parts of speech, category labels for the objects (which can be partially overlapping) such as animal-word or long-word or concrete-word or happy-word or any other semantic or syntactic or pragmatic category, sentence fragments incorporating information regarding the objects, sentences with words for the objects in them, auditory representations of the objects (e.g., tick-tock for the clock object 510), visual representations of the type of object or category of object, olfactory representations of objects (e.g., flowers, foods, etc.), tactile representations of the objects, haptic representations of the objects, or any mix of types of object representations. In some embodiments, object representations can include items that relate to but might not fully represent the particular object. In one example, upon selection of a particular object 508, 510, the machine vision language tutor algorithm 532*a* may present the individual 502 with a foreign language lesson incorporating the selected object 508 or 510, such as the Spanish word for ball or a sentence describing the present time of day in Mandarin Chinese. The foreign language lesson, in some examples, may involve execution of a single word reading algorithm 532*b* and/or a graphic enhanced vocabulary algorithm 532*d*, described in greater detail in relation to FIG. 5B.

In some implementations, a caregiver, teacher, or other user associates each label with particular object data. For example, a user may print labels to apply to objects around the home, associating each object with at least a first piece of data (e.g., printed name or vocalized name). In another example, the user or caregiver may purchase labels (e.g., sheets of sticker labels), scan each label with a standardized index element scanning application (e.g., built into the wearable data collection device or downloadable to a personal computing device including scanning capability such as a smart phone), and associate each scanned label with object data. The user or caregiver may then apply the labels to the associated objects. In this manner, a user or caregiver may customize information gathering within a chosen vicinity (e.g., classroom, child's bedroom, clinical office, etc.).

The mode of operation may further involve receiving responses from the individual 502 regarding presented object data 506*f*. For example, as illustrated, the word "clock" 526 is intoned to the individual 502. The currently active software module may be a verbal skill building module (e.g., English language or foreign language mode) anticipating repetition of the intoned word. Upon identifying a spoken response within voice recording data 116*a*, the verbal skill building module may validate the response and store the result (e.g., proximity in pronunciation) as response validation data 506*c*. Furthermore, the verbal skill building module may present feedback data 506*e* to the individual 502 regarding relative success of pronunciation. The feedback data 506*e*, in some examples, can include a visual indication (e.g., green check or red "X" presented in a heads up display) and/or audible indication (e.g., fanfare or buzzer). If the software module is presenting a language lesson game, in some implementations, progress tracking data 506*d* is collected to track the success of the individual 502 in learning verbalizations associated with the labeled objects 508, 510. A single word reading algorithm 532*b*, in another example, may behave similarly to the series of events described above in relation to the verbal skill building module 536*c*, but presenting a graphic illustration of the word "clock" 526 in lieu of the intonation.

In some implementations, interactions of the individual 502 with labeled objects 508, 510 can take place in the form of a game. For example, video augmentation data 506*b* may include an augmentation style to convert the vicinity to a virtual reality zone having a particular presentation style. The presentation style, in some examples, can include a line-drawn version of the vicinity, a cartoon-drawn version of the vicinity, or a simplified version of the vicinity, for example where the majority of the scene is reduced to wire frame with only the objects 508 and 510 presented in full color. In another example, the presentation style may include a full color version of the video recording data 116*b* with augmentation of the objects 508, 510 (e.g., cartoon drawing, outlined in colorful lines, sparkling, jiggling, etc.).

In some implementations, the machine vision language tutor algorithm 532*a*, executing upon or in conjunction with the wearable data collection device 504, correlates identified object indices 506*a* with the location coordinates 506*g* of the index elements 512 at the time of acquisition. The location coordinates 506*g*, for example, may include two-dimensional coordinates (e.g., within a video frame reference) or three-dimensional coordinates (e.g., with respect to the individual 102). Identification of the object indices 506*a*, furthermore, may be associated with a time-date stamp identifying the time of acquisition. The location coordinates can be factored into presenting information to the individual 502 related to the objects 508, 510. For example, if the ball object 508 had been moving when the wearable data collection device 504 registered the index element 512*a*, the machine vision language tutor algorithm 532*a* could present a representation of the ball object 508 to the individual 502 showing the ball 508 in a different location based on the passage of time and motion characteristics of the ball 508 (e.g., as identified within the video recording data 116*b*). Likewise, the machine vision language tutor algorithm 532*a* may identify movement of the head of the individual 502 based upon sensor elements within and/or coordinating with the wearable data collection device 504 (e.g., via motion tracking data 116*h* and/or head position data 116*d*) between the time of acquisition of the index element 512*a* and time of output of object data 506*f* regarding the ball object 508 to the individual 502. Based upon the identified movements, the machine vision language tutor algorithm 532*a* may adjust the object data 506*f* accordingly. For instance in the case of a visual image, the machine vision language tutor algorithm 532*a* can cause a shift in the visual image to represent the current head gaze direction as opposed to the one at the time of acquisition—a form of motion correction.

Head gaze direction 116*d* and subject motion data 116*h*, in some implementations, may be used by the machine vision language tutor algorithm 532*a* to identify which object data 506*f* to present to the individual 502. For example, based upon a present gaze trajectory of the individual 502 (e.g., based upon head position data 116*d* and/or eye tracking data 116*g*), object data 506*f* regarding the clock object 510, rather than object data 506*f* regarding the ball object 508, may be presented to the individual 502.

In some implementations, the machine vision language tutor algorithm 532*a* uses the location coordinates 506*g* of the index elements 512 to identify three-dimensional locations of the objects 508, 510 with reference to the individual 502. For example, location coordinates 506g may be derived from triangulation of video recording data 116b obtained at multiple angles. In another example, location coordinates 506g may be obtained from transmission features of the RFID tag 512a or other type of electronic label.

Using the location coordinates 506g, in some implementations, an audible locator module plays audible tones to the individual 502 that indicate relative distance and/or direction of each object 508, 510 from the individual 502. The intensity and directionality (e.g., left/right balance or other speaker distribution) of the audible tones, for example, can be stored as presentation feedback data 506e of the wearable data collection device 504. Each object 508, 510, further, may be associated with a particular sound. For example, the ball object 508 may be indicated by a bouncing noise, while the clock object 510 may be indicated by a tick-tock noise. Using the audible locator algorithm 548, a blind individual 502 could discover the nature of her environment by receiving audible feedback representing the depth and breadth of a room and the location of objects within it by scanning the scene and receiving audible tone-based feedback from the wearable data collection device 504. Alternatively or additionally, the presentation feedback data 506e regarding locations of the objects 508, 510 can include tactile or haptic feedback. For example, the machine vision language tutor algorithm 532a may translate distance and relative position of an object into vibrational intensity, patterns, and application point (should multiple tactile feedback application points be available upon the body of the individual 502).

In some implementations, an object tracking software module of the machine vision language tutor algorithm 532a tracks the three-dimensional object location during a period of time. For example, tracking of the position of each object within a vicinity may aid in inventory management. During chemistry experiments in a chemistry laboratory, for example, the object tracking software module may determine which laboratory technicians interacted with each of the various chemical compounds, pieces of equipment, and other objects with standardized index elements within the vicinity of the laboratory. Based upon timestamps associated with object location data 506f, in one illustration, the object tracking software module may identify, in some examples, when particular laboratory technicians interacted with a particular object, how long a particular object was placed within a freezer, and/or where objects were placed relative to each other in a refrigerated storage area (e.g., on a shelf above or below another object). In other implementations, the object tracking software module functions as a stand-alone algorithm, not including the language learning and/or graphic enhancement features of the machine vision language tutor algorithm 532a.

In some implementations, by analyzing object location data 506f cross-referenced with one or more of motion tracking data 116h, video recording data 116b and audio recording data 116a, the machine vision language tutor 532a (or software tracking module) may identify how the individual 502 has interacted with a particular labeled object 508, 510. For example, the machine vision language tutor 532a may identify that the individual 502 threw the ball 508 to the right of the clock 510. Furthermore, analysis of the audio recording data 116a may derive information regarding the level of familiarity of knowledge the individual 502 has with a particular object, for example through recognition of the individual 502 speaking the name of the object.

In some implementations, the level of familiarity, level of comfort, and/or level of discomfort the individual 502 has with a particular object may be derived through physiological data, such as heart and breath data 116e, EMG data 116i, or EEG data 116f, described in relation to FIG. 1A, as well as voice pitch changes (e.g. derived from audio recording data 116a). Furthermore, in some implementations, the wearable data collection device 504 or peripherals in communication therewith may collect data regarding skin conductance dynamics, skin temperature dynamics, core temperature dynamics, and other physiological data for use in familiarity analysis.

In some implementations, an object learning software module of the machine vision language tutor 532a acquires information regarding objects with standardized index elements, improving in object identification such that a labeled object may eventually be identified even when the standardized index element is not visible within the video recording data 116b. In some implementations, a portion of the data 116 and/or 506 acquired by the wearable data collection device 504 is provided to a remote analysis system 514. The remote analysis system 514 may collect session data 516 provided by the wearable data collection device 504 for analysis by a processing system 518. The remote analysis system 514, for example, may perform parts of the machine vision language tutor 532a functionality described above, such as the object identification software module, the object tracking software module or the audible location identifier module.

As illustrated, the processing system 518 includes a learning data analysis module 520 for learning to identify objects. The learning data analysis module 520, for example, may collect and archive data from a number of wearable data collection devices in a data archive 522. The data archive 522, for example, may include a database or training file providing a machine-learning classifier or cascade of classifiers. Further, the data archive 522 may include a database of object information acquired by multiple wearable data collection devices. The learning and data analysis module 520, for example, may categorize the object information. The term "Ball" such as the ball object 508, for example, can represent a category including yoga balls, beach balls, tennis balls, footballs, soccer balls, etc.

In some implementations, the learning and data analysis module 520 recognizes object identifications and categories of object identifications based in part upon demographic data collected from each wearable data collection device. The demographic data, for example, can identify geographic information and spoken language. Through use of demographic data, for example, the learning and data analysis module 520 may learn to differentiate between images of European pears and images of Asian pears while recognizing each as being a "pear". Further, the learning and data analysis module 520 may identify a yellow curved object as a banana in the Boston but a plantain in Borneo.

In some implementations, the pool of learned data derived by the learning and data analysis module 520 is used to refine standardized index element extraction methods or object recognition accuracy. For example, the learning and data analysis module 520 may collect multiple views and rotations of a given object to enhance recognition of the object. Additionally, the learning and data analysis module 520 may collect many versions of a particular category, such as a ball, mug, or telephone, and extract features of items and relationships between the features within the category to derive information about the category itself (e.g., invariant and variant features and feature-feature relationships). The learning achieved by the learning and data analysis module 520, for example, may feed back to the machine vision language tutor 532*a*, allowing the machine vision language tutor 532*a* to recognize items and categories of items without requiring machine code recognition. A portion of this learning may reside in the learning module of the machine vision language tutor 532*a* rather than with the learning and data analysis module 520. Refinements to software modules, such as an object identification module, object data presentation module, and object location tracking module of the machine vision language tutor 532*a*, in some embodiments, are provided as software updates to the wearable data collection device 504 from the remote analysis system 514.

The individual 504, in some implementations, provides feedback regarding labels applied to objects that do not have standardized index elements (or the standardized index element is not visible from the particular view presented within the video recording data 116*b*). For example, the machine vision language tutor 532*a* may prompt the individual 504 to respond whether a suggested label for an identified object has been correctly applied. The wearable data collection device 504 may forward the feedback to the learning and data analysis module 520 to aid in refinement of the automated recognition feature. For example, the learning and data analysis module 520 may track frequency of incorrect object identification and evolve better recognition patterns.

The learning and data analysis module 520, in some implementations, includes a meta-analysis feature for deriving rich information based upon the data collected from a number of wearable data collection devices. In some examples, the learning and data analysis module 520 may analyze the collected data to determine a set of objects most commonly presented to individuals using the machine vision language tutor 532*a*. At a further level of refinement, the learning and data analysis module 520 may identify commonly presented objects by age or age range of the individual (e.g., toddlers, grade school children, etc.), geographic location of the individual, or other classifications of the individual based upon demographic and/or medical diagnosis information (e.g., as stored within a user profile associated with each individual). In another example, the learning and data analysis module 520 may track and analyze the performance of individuals (e.g., including the individual 504) in learning words, phrases, or other information presented by the machine vision language tutor 532*a*. The performance analysis may be broken down into sub-categories, such as performance by operating mode of the machine vision language tutor 532*a* (e.g., single word vs. short phrases, etc.), age range, geographic location, or other classifications of individuals based upon demographic and/or medical diagnosis information.

In some implementations, the single word reading algorithm 532*b* of FIG. 5B recognizes text being reviewed by the individual 502 wearing the wearable data collection device 504 and highlights particular portions of the text for the individual 502. The single word reading algorithm 532*b*, for example, may use one or more optical character recognition modules to identify that text has been captured within the video recording data 116*b*. Upon recognition of the text, the single word reading algorithm 532*b* may magnify, brighten, sharpen, or otherwise draw forth a portion of the text available to the individual 502 within a display region (e.g., heads up display) of the wearable data collection device 504. Further, the single word reading algorithm 532*b* may adjust a font style or weight, text color, or other aspects of the presented font to enhance readability and/or draw further attention to a particular portion of the text. In adjusting the presentation of the portion of the text identified within the video recording data 116*b*, in some examples, the single word reading algorithm 532*b* may enhance readability based upon preferences or capacities of the individual 502. For example, the single word reading algorithm 532*b* may enhance the text in a manner which allows the individual 502, having impaired vision, to better read the text. The modifications applied by the single word reading algorithm 532*b* to the rendering of the text, for example, may include adjustment of the presented text to factor in astigmatism of the individual 502, partial blindness, color blindness, or other condition which may frustrate interpretation of the text.

The single word reading algorithm 532*b*, in some implementations, selects a portion of the text from a greater body of text (e.g., three lines, five words, etc.) to highlight. The single word reading algorithm 532*b* may additionally de-emphasize the remaining text within the display of the wearable data collection device 504, for example by dimming, blurring, or otherwise obscuring or partially obscuring the remaining text. In this manner, the attention of the individual 502 is directed to a portion of the text that has been highlighted or enhanced by the single word reading algorithm 532*b*.

The single word reading algorithm 532*b*, in some implementations, provides a moving enhancement of the text. For example, to aid in the reading of lengthier text, such as a newspaper article or page of a book, the single word reading algorithm 532*b* may provide the individual 502 with the opportunity to "read along" by adjusting the portion of the enhancement through an input mechanism of the wearable data collection device 504. The individual 502, in some examples, may provide an audible cue (e.g., saying "next"), a visual cue (e.g., "dragging" finger along text within video recording data 116*b* captured by the wearable data collection device 504), and/or a physical cue (e.g., touching a portion of the wearable data collection device 504 or a peripheral in communication with the wearable data collection device 504) to signal the single word reading algorithm 532*b* to advance the highlighting to a next portion of the text.

In some implementations, the learning and data analysis modules 520 may learn a reading speed and/or preferred adjustment style of the individual 502, allowing the single word reading algorithm 532*b* to automatically adjust and present the text accordingly until signaled otherwise by the individual 502 (e.g., via an input cue as described above). For example, the learning and data analysis modules 520 may identify that the individual 502₂ progresses more quickly through text when presented with a serif font than a sans serif font.

In some implementations, the single word reading algorithm 532*b* may parse the text to recognize words and/or phrases, for example matching the terms with associated information. In one illustration, through a database look-up (e.g., resident to the wearable data collection device 504, executed upon a separate computing device in communication with the wearable data collection device 504, and/or implemented within the remote analysis system 514 of FIG. 5A), the single word reading algorithm 532*b* may identify definitions, pronunciations, graphic or video illustrations, audio snippets, and other rich information associated with an identified word of phrase. The single word reading algorithm 532*b* may then present enhanced information to the individual 502 regarding the presented text, automatically or upon selection. In a particular illustration, the single word reading algorithm 532b provides the individual 502 with the opportunity to select a word or phrase within the text for additional information, such as pronunciation, definition, and/or graphic illustration (e.g., what does a crested gecko look like, what is the pronunciation of "inchoate", or what does "lethargy" mean).

The single word reading algorithm 532b, in some implementations, may be combined with other algorithms executing on the wearable data collection device 504, such as, in some examples, a bouncing ball reading algorithm 532c or a graphic enhanced vocabulary algorithm 532d. Similar to the single word reading algorithm 532b, in some implementations, the bouncing ball reading algorithm 532c presents, to the individual 502, enhanced text as identified within the video recording data 116b. The enhanced text, for example, may be superimposed with an attention window or otherwise selectively highlighted by the bouncing ball reading algorithm 532c to identify text for the individual 502 to read. For example, a child may interact with the bouncing ball reading algorithm 532c while reading a favorite book. The bouncing ball reading algorithm 532c may present a portion of the text of the book in a highlighted or enhanced fashion, then analyze audio recording data 116a to identify audible terms corresponding to the text on the page. As the child reads, the bouncing ball reading algorithm 532c may advance the enhanced portion of the text along the page of the book as presented in video data upon a display region of the wearable data collection device 504.

The bouncing ball reading algorithm 532c, in some implementations, rewards the individual 502 for correct reading of the text. In some examples, the bouncing ball reading algorithm 532c may allocate points towards a gaming enhanced interaction (e.g., using a gaming module), illustrate an icon or word of congratulations (e.g., a green checkmark for correct reading), or supply audible or tactile feedback identifying to the individual 502 that the individual 502 read the text successfully.

In some implementations, if the individual 502 struggles with pronunciation of the text or misses or misinterprets words within the text, the bouncing ball reading algorithm 532c supplies corrections. For example, the bouncing ball reading algorithm 532c may correct pronunciation, return to a particular word or phrase to encourage the individual 502 to try again, or supply a visual, audible, or tactile form of feedback to alert the individual 502 that there were problems with the reading performance.

The bouncing ball reading algorithm 532c, in some implementations, includes a reading style learning module (e.g., as part of the learning and data analysis modules) configured to learn, in some examples, the accent, speech patterns, and other verbal mannerisms of the individual 502. For example, the reading style learning module may improve the reading recognition of the bouncing ball reading algorithm 532c in relation to the individual 502, such that the bouncing ball reading algorithm 532c may recover for a lisp, stutter, or other impediment which may cause greater difficulties in interpreting the vocalization of the individual 502 during reading. Further, the bouncing ball reading algorithm 532c may be combined with a speech dysfluency coach algorithm 540a (described in greater detail below) to aid in correction of speech dysfluencies identified while interacting with the bouncing ball reading algorithm 532c.

Upon conclusion of a portion of reading (e.g., a page, chapter, book, article, etc.), in some implementations, the bouncing ball reading algorithm 532c tests comprehension or recall of the individual 502. For example, the bouncing ball reading algorithm 532c may include a quizzing module which correlates information within the text (e.g., phrases, characters, actions, etc.) with questions for the individual 502 to gauge the performance of the individual 502 in reading. In some examples, the bouncing ball reading algorithm 532c may verify understanding of a term (e.g., select an appropriate definition), confirm proper identification of a series of actions within a text (e.g., the baker mixed the bread prior to putting the pan in the oven), or identify a particular character (e.g., is Emily a girl, a boy, or cat). The quizzing module of the bouncing ball reading algorithm 532c may interoperate with the gaming module, awarding points for correct answers. The quizzing module, in another example, may feed information to the learning and data analysis modules 520 to gauge and track the reading level of the individual 502, along with strengths and weaknesses of the reading abilities of the individual 502.

In some implementations, a graphic enhanced vocabulary algorithm 532d illustrates an image or a visual-sentence action to accompany and transliterate what is being read. For example, while using the single word reading algorithm 532b or the bouncing ball reading algorithm 532c, the reading activity may include visual information appended to the display (e.g., proximate to the text being read) by the graphic enhanced vocabulary algorithm 532d. In another example, the graphic enhanced vocabulary algorithm 532d may function in tandem with the machine vision language tutor 532a to provide image data and/or a visual-sentence action corresponding to an identified object in the vicinity of the individual.

In some implementations, a consonant-slowing speech filter algorithm 534a provides an individual with the opportunity to slow verbal dialogue for better comprehension. Individuals with autism spectrum disorder often struggle to hear consonants well. Because of the difficulty with consonant recognition, boundaries between words may be blurred. The consonant-slowing speech filter algorithm 534a may filter audio data captured by the wearable data collection device prior to presentation to the individual 502 (e.g., via an audio output feature such as headphones, ear buds, or bone conduction speaker). In the event that the audio output method is not audio-suppressing (e.g., noise-suppressing headphones), the output of the consonant-slowing speech filter algorithm 534a may be presented such that it overlays speech the individual is naturally hearing.

In some implementations, the consonant-slowing speech filter algorithm 534a functions with other modules and algorithms presenting audio data to the individual 502 such that, prior to output, any speech related audio data is filtered to slow consonants for better comprehension by the individual 502. For example, during review of video training information or presentation of verbal information regarding an object identified through the machine vision language tutor algorithm 532a, the consonant-slowing speech filter algorithm 534a may be called to slow the consonants of the speech portion of the audio output prior to presentation to the individual 502.

A boundary-enhancing speech filter 534b, in some implementations, alters audio data containing verbal components to accentuate words and segment boundaries. In this manner, the boundary-enhancing speech filter 534b may act as an edge-detector or edge-enhancement filter for linguistic elements. The boundary-enhancing speech filter 534b may filter audio data captured by the wearable data collection device 504 prior to presentation to the individual 502 (e.g., via an audio output feature such as headphones, ear buds, or bone conduction speaker). In the event that the audio output method is not audio-suppressing (e.g., as in noise-suppressing headphones), the output of the boundary-enhancing speech filter 534b may be presented overlaying speech the individual is naturally hearing.

In some implementations, the boundary-enhancing speech filter 534b functions with other modules and algorithms presenting audio data to the individual 502 such that, prior to output, any speech related audio data is filtered to slow consonants for better comprehension by the individual 502. For example, during review of video training information or presentation of verbal information regarding an object identified through the machine vision language tutor algorithm 532a, the consonant-slowing speech filter algorithm 534a may be called to slow the consonants of the speech portion of the audio output prior to presentation to the individual 502. Further, the boundary-enhancing speech filter 534b may coordinate with the consonant-slowing speech filter 534a to both slow consonants and enhance boundaries of speech prior to presentation to the individual 502.

A speech dysfluency coach algorithm 540a, in some implementations, reviews audio data collected by a wearable data collection device 504 in real time to identify speech "tics", filler utterances (e.g., umm, err, etc.), stuttering, and/or other speech dysfluencies. Responsive to identifying a speech dysfluency, the speech dysfluency coach algorithm 540a may cue the individual 502 using the wearable data collection device 504, for example using a visual, audible, or haptic cue. Upon providing the cue, the speech dysfluency coach algorithm 540a may assess effectiveness of the cue. For example, the speech dysfluency coach algorithm 540a may assess whether the cue threw the individual 502 off-course (e.g., stammering, excessive pause, starting over with a sentence/topic, etc.). Based upon the assessment of effectiveness, the speech dysfluency coach algorithm 540a may alter the style of the cue when next presenting feedback to the individual 502.

In some implementations, the speech dysfluency coach algorithm 540a tracks progress over time. As a training and management exercise, the speech dysfluency coach algorithm 540a may deduct points for identification of speech dysfluencies, while awarding points for threshold timeframes of speech patterns without evidence of speech dysfluency. Progress tracking may include, for example, providing a report to a caregiver, medical practitioner, or educator for assessment including information regarding point accrual, types of speech dysfluencies identified, and/or a comparison of frequency of speech dysfluencies over time.

Similar to the speech dysfluency coach algorithm 540a, in some implementations, a profanity and colloquialism coach algorithm 540c reviews audio data collected by the wearable data collection device 504 in real time to identify usage of profanity and other base or offensive speech. Additionally, the profanity and colloquialism coach algorithm 540c may monitor gestures of the individual 502 to identify profane gestures made by the individual 502. Based upon identification of profane verbal or physical expressions, the profanity and colloquialism coach algorithm 540c may cue the individual 502, deduct points, and/or track frequency and type of uses and generate progress reports. Unlike the speech dysfluency coach algorithm 540a, the profanity and colloquialism coach algorithm 540c may modify response based upon context (e.g., identification of other members of a conversation, location, tone of the conversation, etc.). For example, the profanity and colloquialism coach algorithm 540c may provide strict correction in the school environment when communicating with a teacher, but relaxed correction in the home environment when communicating with a friend.

On a broader range, a social acceptability coach algorithm 540b, in some implementations, reviews audio data collected by the wearable data collection device 504 in real time to identify topics of conversation that may not be socially acceptable in the individual's present environment. The social acceptability coach algorithm 540b, for example, may identify key words and phrases, as well as densities of key words in extended speech, to determine topics of conversation that may be better avoided. The questionable topics of conversation may be cross-referenced with a present environment. For example, a topic of conversation appropriate at the playground may not be as socially appropriate at a funeral. Additionally, the social acceptability coach algorithm 540b may consider a cultural environment of the individual 502 in determining whether a topic of conversation is appropriate. The cultural environment, in some examples, may include information regarding ethnicity, race, gender, age group, context (e.g., school, home, family member's residence, etc.), or religion. Similar to the speech dysfluency coach algorithm 540a and the colloquialism coach algorithm 540c, the social acceptability coach algorithm 540b may issue a warning to the individual 502 to cue the individual 402 to cease engaging in the present topic of conversation. Further, the social acceptability coach algorithm 540b may alert a caregiver or begin recording depending upon the level of inappropriateness of a topic of conversation.

A teleprompter algorithm 544, in some implementations, calls upon a number of the features of other algorithms 532, 538, and 540 to support the individual 502 in giving speeches or otherwise engaging in social interactions with others. For example, the teleprompter algorithm 544 may present a script to the individual 502 in a heads-up display of the wearable data collection device 504. The teleprompter algorithm 544, for example, may present a portion of the script at a time in a similar manner as the bouncing ball reading algorithm 532c. The script, in some examples, may be a transcript of an actual speech or socially appropriate conversations snippets.

In some implementations, a full conversation snippets algorithm 536a, working in tandem with the teleprompter algorithm 544, accesses archetype conversation snippets appropriate to a given circumstance. The conversation snippets, for example, may be stored in a database within the wearable data collection device 504 or on another computing device in communication with the wearable data collection device 504. In another example, conversation snippets may be fed to the individual 502 through a live coach (e.g., human) feeding conversation snippets to the individual 502 over a network through the full conversation snippets algorithm 536a. The coach, in some examples, may be a personal conversational assistant, a caregiver, or a colleague. For example, if the individual 502 is meeting with a potential business partner, other colleagues of the individual 502 may attend the discussion through a live video feed established with the wearable data collection device 504, similar in manner to the evaluation features described in relation to FIG. 1A. The colleagues may supply information, such as budget numbers, time estimates, and other information, to the individual 502 through the full conversation snippets algorithm 536a.

In automatically selecting an appropriate conversation snippet, in some implementations, the full conversation snippets algorithm 536a uses features of the social acceptability coach 540b and/or the personal distance coach 542a to identify situational circumstances (e.g., type of event, location, ages of other members of the conversation, as well as cultural, racial, religious, or other factors) as well as present attitudes of the other members of the conversation (e.g., emotional and body language cues demonstrating a current emotional state of each member of the conversation).

Additionally, in some implementations, a sentences and exchanges algorithm 536b coordinates with the teleprompter algorithm 544 to parse elements of the conversation, identifying emotional cues within the speech of the individual 502. While the individual 502 is speaking, for example, the sentences and exchanges algorithm 536b may parse audio data collected by the wearable data collection device for speech elements such as, in some examples, the tone of voice and the ongoing lilt and rhythm (prosody) of the individual's voice, using this analysis to derive verbal emotional cues provided by the individual 502 to the other members of the conversation. In the example of prosody, the sentences and exchanges algorithm 536b may analyze individual word choices, words and phrases used as colored by the greater conversations, and/or characteristics applied to words or phrases (e.g., boldness, formality, familiarity, etc.). Further, based upon analysis of the ongoing conversation, the sentences and exchanges algorithm 536b may present one or more cues to the individual 502 through the wearable data collection device 504. For example, the sentences and exchanges algorithm 536b may present an audible cue and/or visual cue to identify a point at which the individual 502 should pause or should emphasis a word while presenting a conversation snippet or speech fed to the individual 502 by the teleprompter algorithm 540.

In some implementations, the teleprompter algorithm 544 coordinates with the timing of cultural and conversational gestures algorithm 538a and/or the performance of cultural and conversational gestures algorithm 538b to prompt the individual 502 to insert appropriate gestures (e.g., nodding, smiling, etc.) at the appropriate time. Further, the timing of cultural and conversational gestures algorithm 538a may prompt the individual 502 to reduce gesturing, for example upon identifying that a level of movement of the individual 502 is likely to have a distracting effect on the other members of the conversation or audience. In some implementations, the timing of cultural and conversational gestures algorithm 538a may monitor a gaze position of the individual 502, prompting the individual 502 to recycle his gaze through the audience during presentation of a speech or to look towards the member of the conversation who is presently speaking.

In some implementations, the teleprompter algorithm 544 coaches the individual 502 on conversational pace during performance of a speech or while in conversation with others. For example, the teleprompter algorithm 544 may prompt the individual 502, visually and/or audibly, to slow down.

The teleprompter algorithm 544, in some implementations, coaches the individual 502 on loudness of speech. For example, the teleprompter algorithm 544 may analyze data captured by a microphone feature of the wearable data collection device 504 to measure the sound level of the individual's voice. Further, the teleprompter algorithm 544 may adjust its analysis to take into consideration background noise and/or nearness of other members of the conversation (for example by estimating distances using features of the personal distance coach algorithm 542a). Responsive to analysis, the teleprompter algorithm 544 may prompt the individual 502 through the wearable data collection device 504, visually and/or audibly, to adjust speaking volume. In a particular example, the teleprompter algorithm 544 may present, upon a heads up display of the wearable data collection device 504, an icon of a cartoon covering its ears and saying ouch when the individual 502 is speaking too loud or a cartoon tilting its ear and cupping its hand when the individual 502 is speaking too softly.

In some implementations, the individual 502 can invoke the teleprompter algorithm 544 to practice a speech or impromptu conversational skills. For example, the sentences and exchanges algorithm 536b may be used to automatically "respond" to the individual 502 through analysis of sentences verbalized by the individual 502 within audio data captured by the wearable data collection device 504 and selection of appropriate response conversation snippets based upon the analysis. While the individual 502 is practicing performance of a speech or practicing conversation skills, the teleprompter algorithm 544 may analyze the vocalizations of the individual 502 to evaluate strengths and weaknesses of a performance. For example, the teleprompter algorithm 544 may invoke the speech dysfluency coach algorithm 540a to coach the individual 502 on avoiding filler utterances during practice. Additionally, while practicing a predetermined speech, such as a political speech or lines of a play, the teleprompter algorithm 544 may provide the individual 502 with the opportunity to scroll backwards or forwards within the body of the speech (e.g., repeat practice of a particular line or section of a speech prior to continuing to another portion), for example through features of the bouncing ball reading algorithm 532c.

FIGS. 6A-6D are flow charts of example methods for augmented reality learning using a wearable data collection device having capability to obtain one or both of video recording data and electronic label data (e.g., wireless label transmissions such as those described in relation to FIG. 5A regarding standardized index elements). Augmentation, in one example, may be achieved using techniques described in U.S. Pat. No. 8,188,880 entitled "Methods and Devices for Augmenting a Field of View" and filed Mar. 14, 2011, and in U.S. Patent Application No. 20130021374 entitled "Manipulating and Displaying an Image on a Wearable Computing System and filed Nov. 8, 2011, the contents of each of which is hereby incorporated by reference in its entirety. The wearable data collection device may further have the capability to obtain audio recording data and/or present audible feedback. Additional capabilities of the wearable data collection device may include motion sensors, eye tracking sensors, and head position sensors, such as the hardware and sensors described in relation to FIG. 1A. The motion and/or eye tracking data, for example, may be used by a method 630 to track the gaze of a subject wearing the wearable data collection device. Methods 600, 610, and/or 630 may be performed by one or more software modules executing upon a wearable data collection device such as the wearable data collection device 504 described in relation to FIG. 5A. In another example, one or more of the methods 600, 610, and 630 (or portions thereof) may be executed upon a computing device in communication with a wearable data collection device.

Figure 6A:
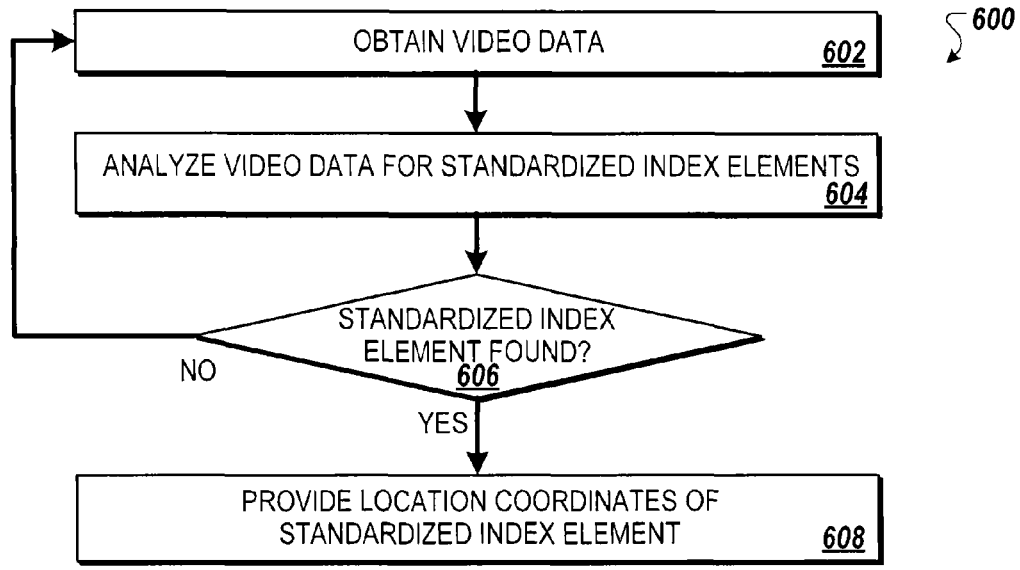
FIG. 6A through 6D illustrate a flow chart of an example method for augmented reality learning using a wearable data collection device.

Turning to FIG. 6A, in some implementations, the method 600 begins with obtaining video data (602). The video data, for example, may include images captured by a head-mounted or otherwise body-mounted camera of a vicinity surrounding an individual. The video data may represent the surroundings of the individual as viewed more-or-less through the eyes of the individual.

In some implementations, the video data is analyzed to identify one or more standardized index elements (604). The standardized index elements may be applied as labels to objects, such as the objects described in relation to FIG. 5A. In other implementations, the standardized index elements may include visible markings upon or built into the objects. In further implementations, the standardized index elements may include electronic signals emitted from one or more objects. The standardized index elements, in some examples, may include a two-dimensional barcode, three-dimensional barcode, QR code, radio-frequency identification (RFID) tags, and other machine-readable labels or electronically transmitting smart labels.

In some implementations, if a standardized index element is located (606), location coordinates of the standardized index element are provided for further analysis (608). The location coordinates, for example, may include two-dimensional coordinates (e.g., within a video frame reference) or three-dimensional coordinates (e.g., with respect to the point of capture). Subsequent analysis, for example, may be executed upon a same or different processing system involving a same or different software module or algorithm. The method 600, for example, may call a separate software algorithm for analyzing the video data at the identified location coordinates to extract information from the standardized index element. In addition to location coordinates, a time stamp of the time of video capture may be provided for further analysis.

In other implementations, instead of or in addition to identifying standardized index elements, an object or classification of an object may be identified. For example, the video data may be analyzed to identify features corresponding to various objects. As with the standardized index elements, the location coordinates of the identified objects may be provided for use by a separate software module, algorithm, and/or computing system. Although described as a linear analysis, in other implementations, the video data is analyzed in parallel (e.g., using multiple threads) and/or recursively to identify standardized index elements.

Figure 6B:
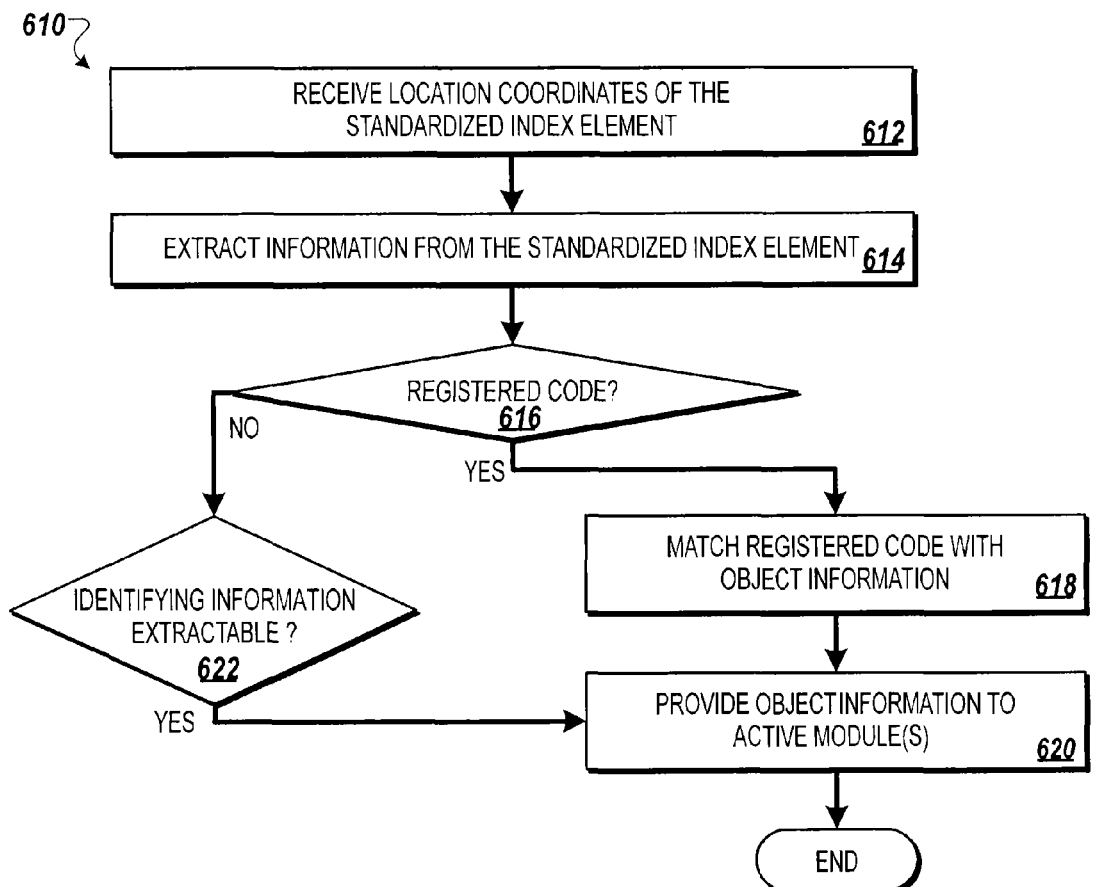

Turning to FIG. 6B, a flow chart illustrates an example method 610 for analyzing an identified standardized index element to derive object information. In some implementations, the method 610 begins with receiving the location coordinates of the standardized index element (612). As described in relation to FIG. 6A, the location coordinates may be supplied from a separate algorithm or module executing upon a same or different processing system. In some implementations, information is extracted from the standardized index element (614). One or more hardware, firmware, or software elements of a wearable data collection device, for example, may be used to scan the video data for the standardized index element. For example, an RFID scanner feature of a wearable data collection device or other machine-vision processes may be used to scan the standardized index element for information. To improve recognition of objects encoded with standardized index elements within the vicinity, in some implementations, two or more separate methods may be used to identifying items. Objects identified using one recognition method may be cross-referenced with the objects identified using the second recognition method. In other implementations, audio data and/or wireless transmission data may be reviewed using machine-hearing or other signal processing abilities to identify audible or other electronic signals of standardized index elements.

In some implementations, a standardized index element only partially identifiable within the video feed may be read (if readable by one or more scanning systems) to obtain an object index. Further, if the object was previously scanned and recognized, based upon a visible portion of the standardized index element, the method 610 may be able to identify the particular object (e.g., using information in a local database or training file entry associated with the object having the standardized index element). A shape of the object in combination with a partial standardized index element, in a particular example, may be used to uniquely identify the object.

In some implementations, the information extracted is reviewed for a known index or other code (616). Each standardized index element configured for use with the method 610, for example, may be embedded with a particular identifier (e.g., substring) that is otherwise unlikely to occur in that particular type of standardized index element, such that the identifier can be used to identify standardized index elements created for use with the wearable data collection device. Alternatively, the standardized index element may be embedded with a simple indexing term, such as a noun identifying the associated object.

If the standardized index element includes a known index or other code, in some implementations, object information is matched to the registered code or indexing term (618). For example, the object code or index may be applied to a look-up table to derive associated object data regarding the encoded object. In other examples, the standardized index element is a smart label such as an RFID tag including embedded object data. In this circumstance, the embedded object data is extracted from the standardized index element.

In some implementations, the object information is provided to one or more active modules configured to utilize the object information (620). The method 610, for example, may call a separate software algorithm for using the object information to present feedback to an individual.

In some implementations, if the information extracted does not include a known index or other code (616), the standardized index element is reviewed for identifying information (622). If identifying information is extractable by the method 610 from the standardized indexing element, in some implementations, the object information is provided to one or more active modules configured to utilize the object information (620). For example, if a machine-readable code derived from an object can be used to positively identify the object, such as the UPC code upon a product, the name of the product may be provided to the one or more active modules for use. Further, in some implementations, the object, identified by the machine-readable code, may be added to a database or training list of identified objects (e.g., stored within a wearable data collection device or another computing device in communication with the wearable data collection device).

Figure 6C:
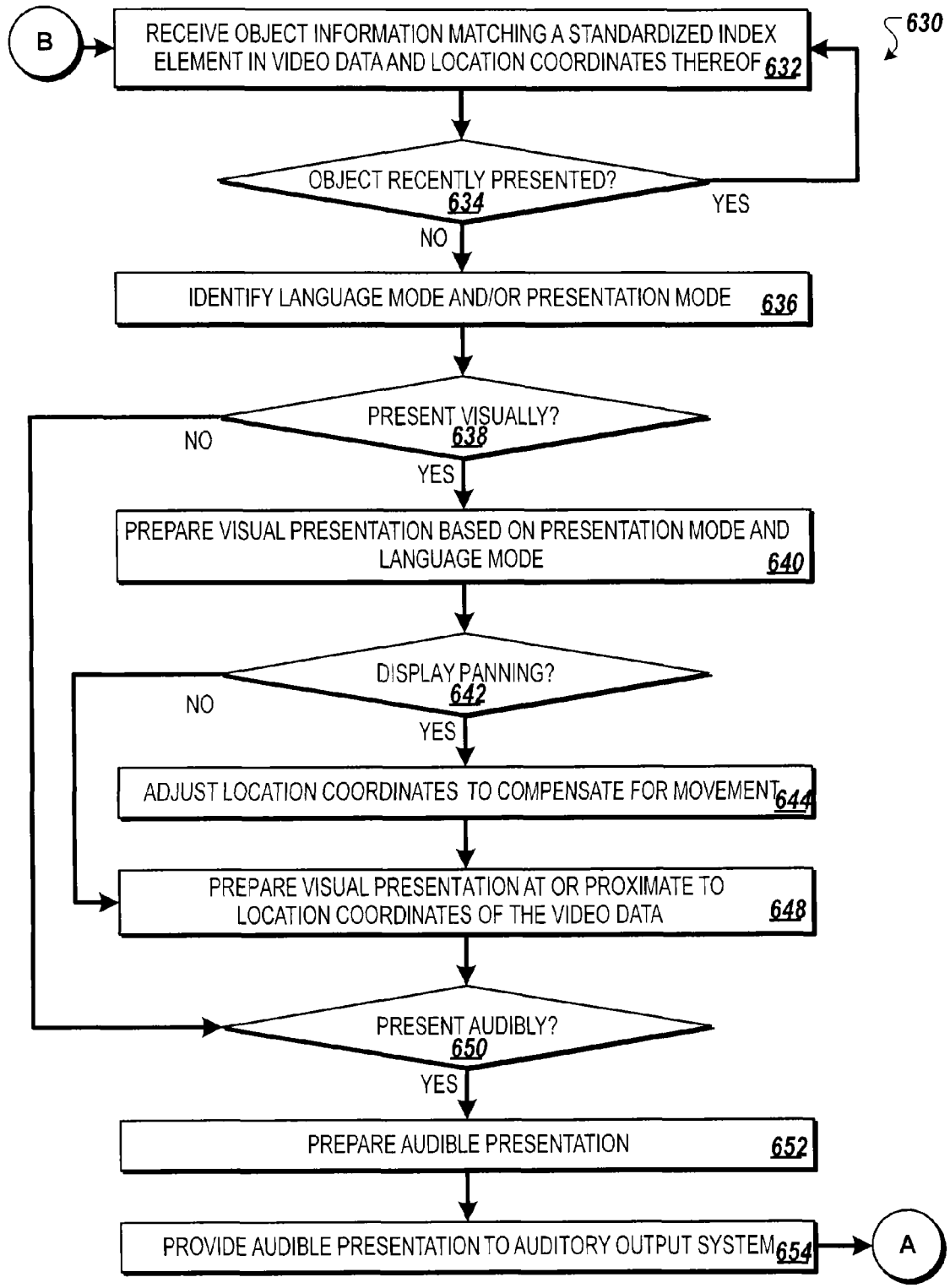
Figure 6D:
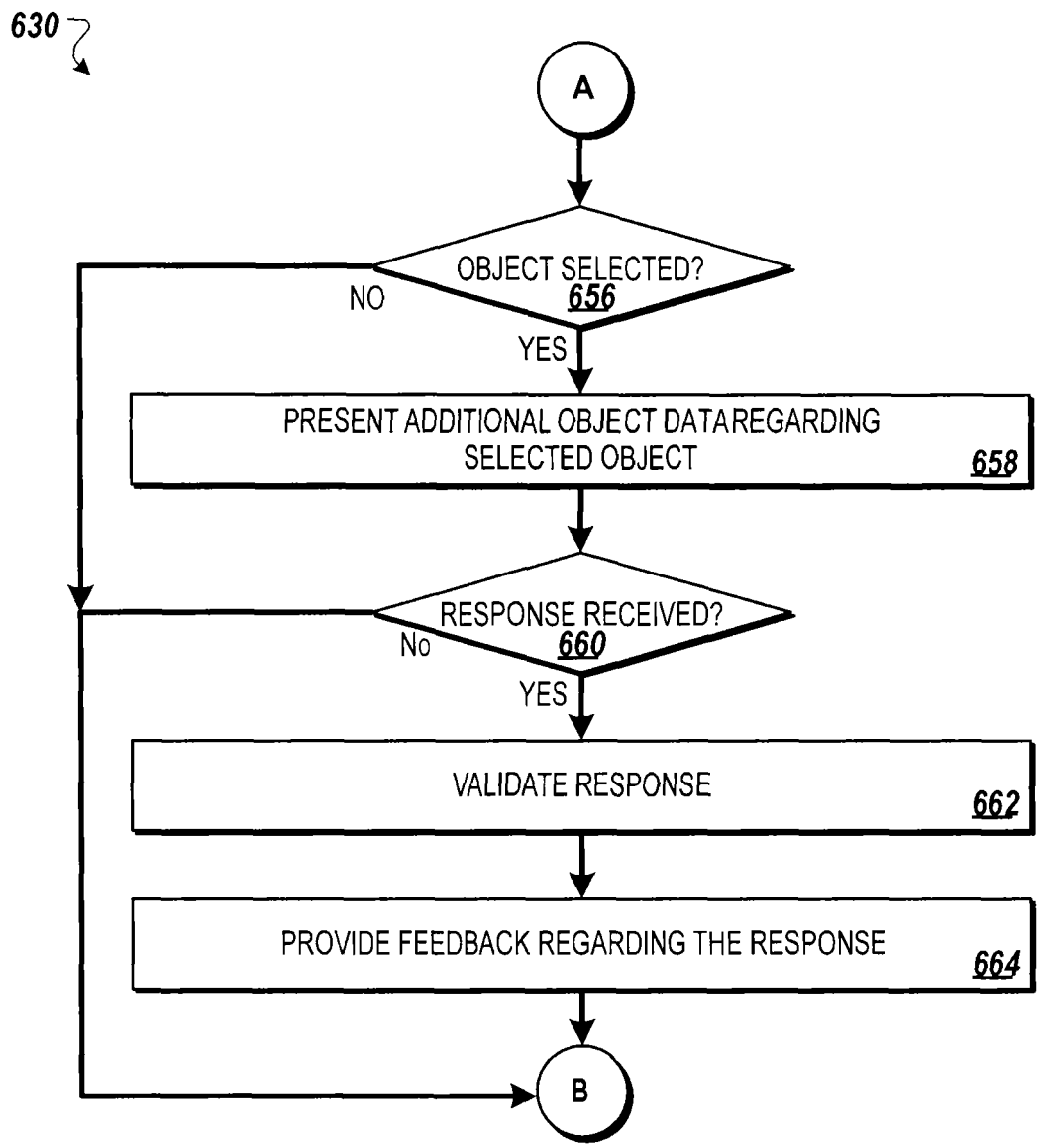

Turning to FIGS. 6C and 6D, a method 630 uses identified objects to present information to an individual donning a wearable data collection device. In some implementations, the method 630 begins with receiving object information matching a standardized index element extracted from video data as well as location coordinates identifying a location of the object within the video data (632). As described above, the object information and location coordinates may be supplied from a separate algorithm or module executing upon a same or different processing system.

If the object information corresponds to an object which was recently presented to the individual (634), in some implementations, the method 630 returns to awaiting receipt of additional object information. In this manner, if an individual was recently presented with information regarding the object, the individual is not repeatedly presented with identical information. A database or log file lookup, for example, may identify when (if ever) the object information was last presented. A threshold time, for example, may be used to determine whether to present information to the individual regarding the identified object.

If the object was not recently presented to the individual (634), in some implementations, a language mode and/or presentation mode is identified (636). For example, a target language setting (or language settings when presenting both a native language and foreign language) may be accessed to determine a language for presentation of any textual and/or verbal feedback presented to the individual. If a language setting includes a language not stored within the object data, the term in a stored language (e.g., English) may be provided to a translation module (internal to the wearable data collection device or externally accessed via a network connection) for translation. Presentation options, in some examples, may include a visual text display setting, a verbal (audible) presentation display setting, and an associated sound (audible) setting. Other presentation settings can include options of learning level or information scope, such as a level of vocabulary, whether to use meta-category labels (e.g., object "dog" belongs to category "animal", etc.), and whether to present single terms or sentences.

If one or more visual presentation settings are active (638), in some implementations, a visual presentation is prepared based upon the presentation mode and language mode (640). The visual presentation, for example, may be prepared for overlay upon current video data. For example, as described in relation to FIG. 5A, the video recording data 116b may be overlaid with a textual representation of one of the labeled objects, such as the word "ball" applied upon or over the ball object 508.

Rather than overlaying with object data, in another example, each the object may be identified as selectable within presented video data by augmenting the video data at or proximate to the location coordinates of the object. For example, the presentation may colorfully outline the object, render the object as a cartoon, cause the object to shimmer, or otherwise augment the object to draw the attention of the individual.

In some implementations, if it is determined that the focal point of the video data captured after the time of identification of the standardized index object has moved (642), the location coordinates are adjusted to compensate for the movement (644). For example, based upon motion of the head of the individual donning the wearable data collection device, the current location of the object may be calculated and the placement of the graphic overlay of the video data adjusted. Conversely, if the object was in motion during video capture, motion data associated with the object may be used to estimate a present position of the object within the video.

In some implementations, the visual presentation is presented at or proximate to the location coordinates within the video data (648). The presentation, for example, may be overlaid upon a present video data frame and caused to display to the user. The user, for example, may see the visual presentation upon a heads-up display of the wearable data collection device.

If one or more audio presentation settings are active (650), in some implementations, audible feedback is prepared for presentation to the individual (652). The audible feedback, for example, may include a word, sentence, and/or sound associated with the identified object.

In some implementations, the audible feedback is provided to an auditory output system (654). The auditory output system, in some examples, may include a speaker system, bone conduction speaker system, or a tethered audio output device (e.g., headphones or ear buds, etc.).

The method 630 continues in FIG. 6D. Turning to FIG. 6D, in some implementations, the individual is presented with an opportunity to select an object (656). Selection of an object, in some examples, may be performed by the individual through an input feature of the wearable data collection device such as a tap, voice command, gesture, or thought pattern.

If an object is selected (656), in some implementations, additional object data regarding the selected object is presented (658). The additional data, for example, can include a deeper level of information, such as, in some examples, one or more terms associated with the object used in a grammatically correct sentence, a description associated with the selected object (e.g., brief encyclopedia-style write-up regarding the object), or other terms used to describe the object (e.g., a car can further be called a vehicle, auto, automobile, etc.). In a particular example, the additional object data includes a vocalized pronunciation of the name of the object.

Selection of the additional information, in some implementations, may depend upon an options menu. The menu may include options such as sentences, usage guides and tips, long definition, images of alternative versions of the object or previous exemplars in the world viewed by the wearer.

In some implementations, a response is received from the individual (660). The individual's response, in some examples, can include a vocal response (e.g., name of the object or other vocalization that may represent familiarity with the object), a physical response (e.g., picking up, touching, or otherwise interacting with the object), and/or an emotional response (e.g., an emotional reaction that may be gauged using voice reflection analysis of audio recording data and/or analysis of various physiological data collected by the wearable data collection device, as described, for example, in relation to FIG. 1A).

If a response is received from the individual (660), in some implementations, the response is validated (662). A vocalized response may be analyzed to identify familiarity with the object. A physical response, in some examples, may be analyzed to identify a comfort level the subject has with the object, dexterity demonstrated regarding use of the object, and/or correctness of use of the object (e.g., a ball object is thrown, not bitten). Further to the example above, the individual may repeat the vocalized pronunciation of the name of the object. The individual's utterance may be recorded as audio recording data and analyzed to determine how well the individual pronounced the name of the object. Validation data, in some implementations, may be recorded to aid in assessment of the individual and/or to track progress of the individual in interacting with objects within the vicinity (e.g., home environment).

In some implementations, feedback regarding the response is provided to the individual (664). The feedback, in some examples, may be presented to encourage a desired reaction to or interaction with the object, discourage an undesired reaction to or interaction with the object, and/or represent relative success in performing a task associated with the object, such as pronouncing the name of the object. Feedback data, in some examples, can include visual feedback, audible feedback, and/or tactile feedback. In the particular example of representing relative success in performing a task associated with the object, a visual indication of a green check or red "X" presented in a heads up display of the wearable data collection device may visually represent success or failure related to the task (e.g., pronouncing the name of the object). Further to the example, in addition to or instead of a visual indication, an audible indication (e.g., fanfare or buzzer) may be used to provide feedback to the individual. Additional discussion regarding the use of feedback and selection of styles of feedback is provided in relation to the method 800 of FIG. 8.

Figure 7A:
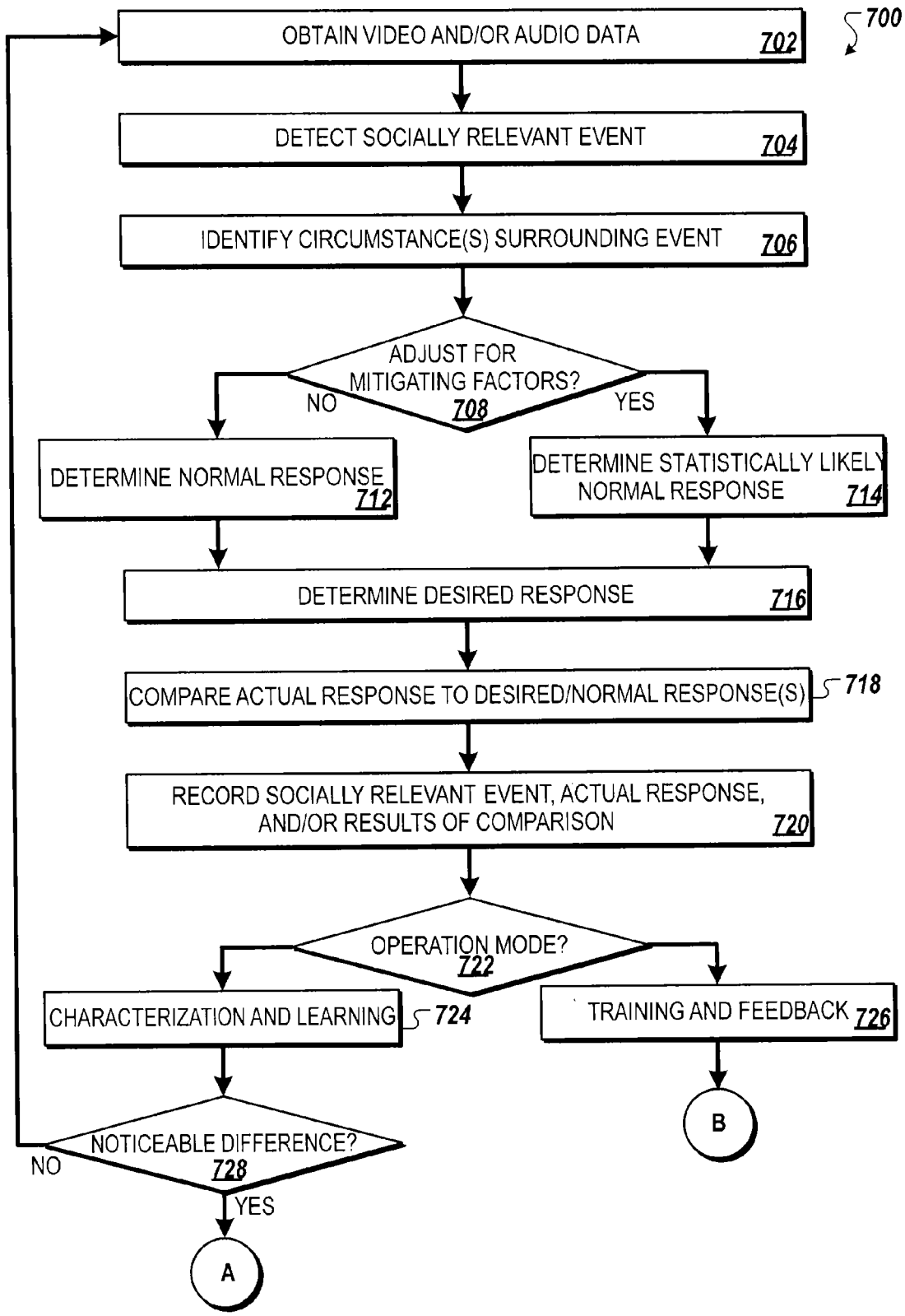
FIGS. 7A through 7C illustrate a flow chart of an example method for identifying socially relevant events and collecting information regarding the response of an individual to socially relevant events.
Figure 7B:
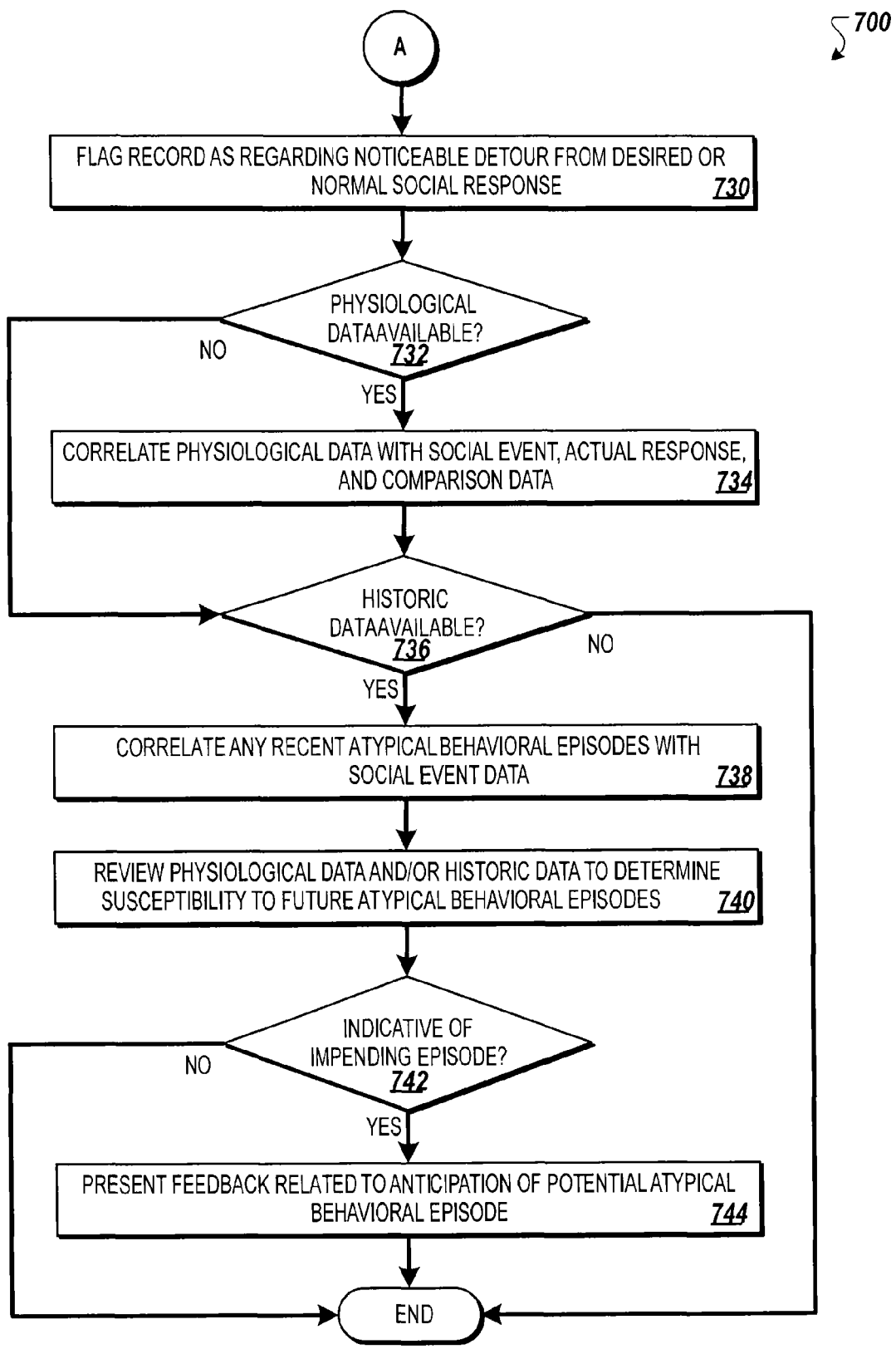
Figure 7C:
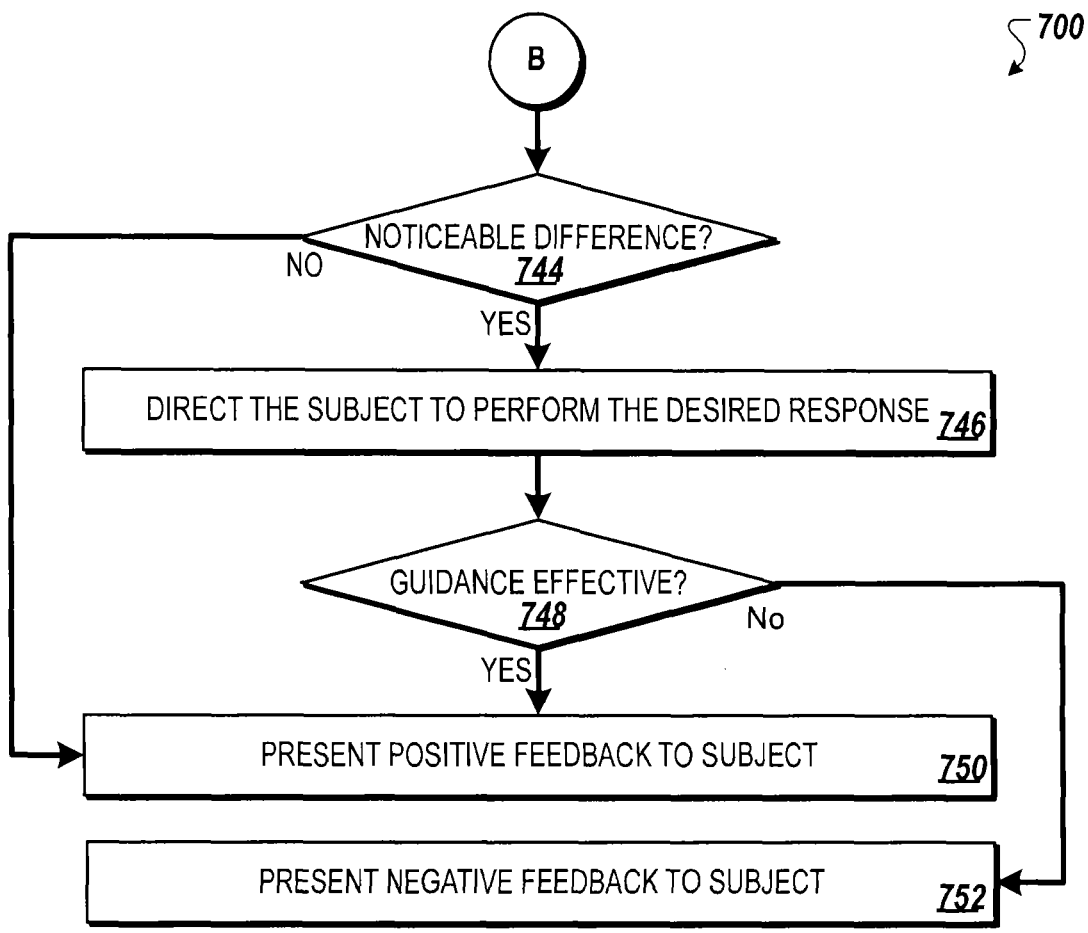

FIGS. 7A through 7C illustrate a flow chart of an example method 700 for identifying socially relevant events and collecting information regarding the response of an individual to socially relevant events using a wearable data collection device. The method 700 may be used in the assessment of an individual's reactions as compared to anticipated typical reactions (e.g., from a typical person sharing characteristics with the subject such as age, sex, developmental stage, etc.). Further, the method 700 may be used in coaching an individual in appropriate responses to social situations.

The wearable data collection device may be capable of collecting video data and/or audio data. The wearable data collection device may further have the capability to present audible and/or visual feedback. Additional capabilities of the wearable data collection device may include motion sensors, eye tracking sensors, and head position sensors, such as the hardware and sensors described in relation to FIG. 1A. The motion and/or eye tracking data, for example, may be used by the method 700 to track the gaze of an individual wearing the wearable data collection device. The method 700 may be performed by a software module executing upon a wearable data collection device such as the wearable data collection device 104 described in relation to FIG. 1A or the wearable data collection device 504 described in relation to FIG. 5A. In another example, the method 700 may be executed upon a computing device in communication with a wearable data collection device.

In some implementations, video data and/or audio data are obtained (702). The video data, for example, may include images captured by a head-mounted or otherwise body-mounted camera of a vicinity surrounding an individual and a second person (e.g., caregiver, family member, evaluator, etc.). The camera may collect video data from the perspective of the individual or the second person. Further, a second camera may be used, such that video data represents both the viewpoint of the individual and the second person. The video data may represent the surroundings of the individual and/or second person, for example, as viewed more-or-less through the eyes of the individual/second person. The audio data, similarly, captures at least vocalizations between the individual and the second person, for example via a microphone mounted on the wearable data collection device or separate computing device.

In some implementations, based upon the video data and/or audio data, a socially relevant event is detected (704). The social relevant event can include an emotional expression typically evocative of an appropriate response by the other party such as, in some examples, smiling, laughing, crying, admonishing in an angry tone, asking a question, using profanity, or invoking the name of the other party. In analyzing the video and/or audio data for a socially relevant event, emotional responses can be characterized by one or more of voice fluctuations, tone, cadence, volume, and prosodic variation of the voice of the speaker, facial expressions, body language, and hand gestures. Furthermore, emotional responses may be derived, in some embodiments, through collection of physiological data, such as the physiological data types described in relation to FIG. 1A (e.g., heart rate, breathing rate, EMG, EEG, etc.). In one example, determining an emotional state associated with the socially relevant event includes providing the various data described above to a classifier which applies a classification of emotion and valence.

In some implementations, it is determined whether to adjust for mitigating factors (708). The method 700, in some embodiments, reviews collected data for extenuating circumstances or other characteristics that may depress typical emotional response. For example, while invocation of the individual's name may typically cause the individual to turn to the attention of the speaker, if the individual is presently distracted (e.g., by a television show, loud noises, nearby activity, or deep concentration in a personal activity) the normal (anticipated) response may be suppressed in the typical individual. Similarly, the individual may respond differently based upon the emotional state of the individual prior to the socially relevant event. In some examples, mitigating factors can include whether the individual was excitable, angry, sad, or otherwise emotionally stimulated in a manner that could accentuate or depress typical response to the socially relevant event. In some examples, an emotional state identifying module may evaluate various physiological data captured by the wearable data collection device and/or peripheral devices in communication with the wearable data collection device such as, in some examples, heart and breath data 116*e*, EMG data 116*i*, or EEG data 116*f*, described in relation to FIG. 1A, as well as voice pitch changes (e.g. derived from audio recording data 116*a*). Furthermore, in some implementations, the wearable data collection device or peripherals in communication therewith may collect data regarding skin conductance dynamics, skin temperature dynamics, core temperature dynamics, and other physiological data for use in emotional state analysis.

If adjusting for mitigation factors (708), in some implementations, a statistically likely normal response, based upon emotional state, external factors, and/or other internal factors (e.g., level of concentration on a task), is determined (714). The statistically normal response, for example, may be derived from data collected from educators, clinicians, and/or physicians regarding behavioral studies and common emotional response patterns. Otherwise, a normal (desired) response is determined (712), similarly based upon collected data regarding common emotional response patterns. In other implementations, the method 700 determines both the normal (desired) response and a statistically likely normal response based upon present mitigating factors.

In some implementations, based at least in part upon the statistically likely normal response and/or the normal response, a desired response is determined (716). The desired response, for example, may include a response determined to be appropriate to the particular individual and/or reasonable for the particular individual to achieve. The desired response, for example, may be based upon a spectrum of known responses common to the particular individual and/or a personality assessment of the particular individual.

In some implementations, the actual response of the individual is compared to the desired response and/or the normal response(s) (718). The comparison may represent a closeness in match between the individual's actual response and one or both of the desired response and the normal response. In some examples, the comparison may include a percentage match or numerical (e.g., level) match. The comparison may refer, in a particular example, to a numerical value indicating a positive (e.g., overreaction) difference between the normal response and the actual response or a negative (e.g., suppressed reaction) difference between the normal response and the actual response.

In some implementations, data regarding the socially relevant event, actual response and/or comparison data is recorded (720). The wearable data collection device, for example, may record the data locally (e.g., in storage built in or directly accessible to the wearable data collection device) and/or remotely (e.g., accessing a network-based system for collection and later assessment/statistical learning analysis of the data). Furthermore, data regarding emotional state, circumstances, and/or other mitigating factors may be recorded in relation to the socially relevant event and response thereto.

In some implementations, the method 700 is used for a number of purposes. These purposes are described herein as operational modes. Although represented as separate and discrete modes in the illustrated flow chart, alternatively, the method 700 may perform at least a portion of the steps associated with each of a characterization and learning mode 724 and a training and feedback mode 726.

In some implementations, a characterization and learning (724) operational mode is determined (722). In the characterization and learning (724) operational mode, if no noticeable/noteworthy difference is discerned between the individual's actual response and at least one of the desired and normal responses (728), the method 700 returns to the beginning and continues to obtain video and/or audio data (702). The concept of "noticeable difference" may represent a statistically significant comparison value, for example as determined by behavioral experts, or may be noticeable in some other way or according to some other thresholding than traditional statistical significance.

If, instead, a noticeable difference is identified (728), turning to FIG. 7B, in some implementations, the data record regarding the socially relevant event is flagged as a noticeable detour from a desired or normal social response (730). In this manner, for example, later analysis can incorporate details regarding any failures of the individual in reacting appropriately to social events.

In some implementations, if physiological data is available (732), the physiological data is correlated with the social event, actual response, and comparison data. As described above, the physiological data can include heart and breath data, EMG data, or EEG data, as well as other physiological factors such as, in some examples, metabolic data, neurological signals, chemodynamics signals, and/or central nervous activity.

In some implementations, if historic data is available (736), one or more recent atypical behavioral episodes may be correlated with the social event data (738). Atypical behavioral episodes, in some examples, can include inappropriate behaviors such as acting-out, extreme emotional fluctuations, and stimming and similar behaviors. Conversely, in some implementations, upon identification of an atypical behavioral episode, historical records regarding recent social response may be reviewed to identify any common behaviors leading up to atypical behavioral episodes. Identification and management of atypical behavioral episodes is discussed in greater detail in relation to FIGS. 11A through 11C.

In some implementations, the physiological data and/or historic data are reviewed to identify susceptibility of the individual to future atypical behavioral episodes (740). As described above, various physiological data captured by the wearable data collection device and/or peripheral devices in communication with the wearable data collection device such as, in some examples, heart and breath data 116e, EMG data 116i, or EEG data 116f, described in relation to FIG. 1A, as well as voice pitch changes (e.g. derived from audio recording data 116a) may be compared to common physiological factors leading up to atypical behavior episodes. The comparison, for example, can be both objective and subjective. Objective comparison of physiological data, for example, can include comparing the individual's physiological data to that of other individuals exhibiting atypical behavioral episodes similar to those of the individual and/or other individuals diagnosed similarly to the individual (e.g., ASD level identification). Subjective comparison of physiological data, for example, can include comparing the individual's present physiological data to historic physiological data of the individual that has been flagged as leading to a past atypical behavioral episode. The comparison may result in a numeric value indicative of present relative susceptibility to an atypical behavioral episode.

Prior to comparison, in some implementations, emotional and physiological states may be derived from the individual's physiological data. The states, for example, can include one or more of a mental state, an arousal level, and an irascibility level. The state information, in turn, may be used to identify a measurement of the individual's present susceptibility to an atypical behavioral episode.

Figure 7D:
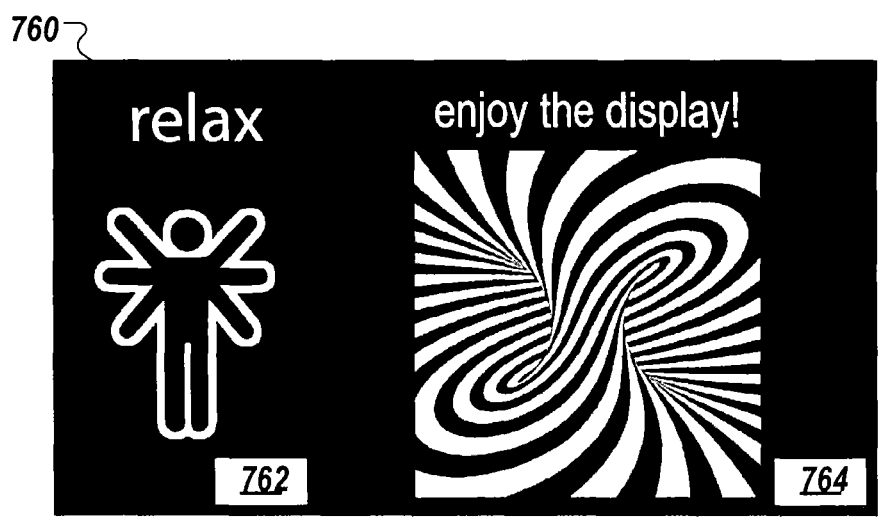
FIG. 7D illustrates a screen shot of an example feedback display for suggesting an intervention to a user.

If the review outcome is indicative a likelihood of an impending atypical behavioral episode (742), in some implementations, feedback related to anticipation of a potential atypical behavioral episode is presented (744). In some implementations, a caregiver is alerted to the likelihood of an impending atypical behavioral episode. For example, the wearable data collection device donned by the caregiver may present an audible and/or visual warning regarding the likelihood of an impending atypical behavioral episode and, potentially, an indication of the type of atypical behavior anticipated (e.g., acting out, stimming, etc.). Furthermore, the caregiver may be prompted with recommendations of measures to take to best prevent, redirect, and/or minimize the atypical behavioral episode. In some implementations, the individual is alerted to the likelihood of an impending atypical behavioral episode. The wearable data collection device donned by the individual, for example, may present an audible and/or visual warning regarding the likelihood of an impending atypical behavioral episode similar to the warning supplied to the caregiver. Further, the individual may be prompted with recommendations of measures to take to minimize or protect against the impending behavioral episode. The individual, in some implementations, may be presented with feedback designed to divert a pending atypical behavioral episode. For example, feedback may be presented via the individual's wearable data collection device (e.g., visual, audible, tactile, etc.) designed to alter one or more physiological conditions indicative of a pending atypical behavioral episode. The feedback, in a particular example, may be designed to calm the emotional state of the individual or focus the individual's attention to divert from a present thought pattern. A variety of particular feedback examples follow. The individual may be presented with a short episode of a game that has proven previously to attract the attention of this individual or others like this individual. The individual may be encouraged to focus on a particular sensation and try to eliminate another sensation from mind. The individual may be instructed to chew or crunch on a food or toy that provides comfort or inward focus for the individual. In a particular example, turning to FIG. 7D, a screen shot 760 includes a prompt pane 762 encouraging the user to relax alongside an image pane 764 configured to provide a pleasurable sensory experience for the user.

Beyond feedback, in some implementations, interventions may be provided on behalf of the individual. For example, a caregiver may be notified and instructed to provide the individual a timeout moment, a pleasant toy, a brief instruction, an enjoyable food or other sensory experience.

In some implementations, the intervention includes a pharmacological or electrical or magnetic form of interaction. For example, the intervention may include triggering of implanted pharmaceutical dispensers or systems for selective release of medicines (including pharmacological agents whose absorption can be influenced externally such as by radio frequency (RF), light, or other method for imparting energy). Furthermore, in some implementations, a stimulator device (described in detail below in relation to FIG. 12) may be used to provide direct intervention via stimulation. For instance, electrical or magnetic pulses may be administered directly to the individual via a stimulator, and the electrical or magnetic pulses may be associated with an instruction or guided behavior that inhibits a potential atypical behavioral episode, or it may directly cause said atypical behavioral episodes to be less likely, for instance by direct neural action or influence. The stimulation, for example, may be used to influence brain circuits by triggering a pleasurable or hedonistic response. Other variations for applying non-invasive effects upon brain functions include, in some examples, transcranial direct-current stimulation (TDCS), transcranial magnetic stimulation (TMS), and radio-frequency energy deposition into tissue, energy deposition into tissue such as brain tissue via radio-frequency oscillations of electromagnetic fields. The magnetic, energy, electrical, and/or pharmaceutical interventions may be automated or semi-automated (e.g., supplied upon approval by a caregiver, medical practitioner, or other authorizing individual). Further, the magnetic, energy, electrical, and/or pharmaceutical interventions, in some implementations, may be used to provide feedback, such as game feedback, to the individual in other tools described herein.

At this point, in some implementations, the method 700 may return to step 702 of FIG. 7A and continue to collect video and/or audio data. In other implementations, the method 700 may further record presentation of feedback such that later analysis can discern whether a particular feedback style appears to stem atypical behavioral episodes in the individual or not.

Turning to FIG. 7C, if the method 700 is performing in the training and feedback mode (726), in some implementations, if a noticeable/noteworthy difference is discerned between the individual's actual response and at least one of the desired and normal responses (744) (e.g., as described in relation to step 728 of FIG. 7A), the individual is directed to perform the desired response (746). In some examples, visual, haptic, and/or audible coaching mechanisms may be used to trigger a desired response from the individual. In a particular example, a funny sound may be played to invoke a smile or giggle from the individual in response to a socially relevant event that normally invokes pleasure. The video feed of a heads-up display, in another example, may be augmented to highlight a face for the individual to look at or otherwise direct the gaze of the individual towards a speaker, such as by using a graphic arrow indicating to the individual to turn her head in a particular direction. Further to the example, a video icon of an arrow may "grow" and "shrink" based upon whether the individual is turning away or towards the direction of the arrow. Additionally, audio or video feedback may spell out to the individual the particular desired behavior to invoke, such as an audible cue directing the individual to "smile now" or a visual cue including the text "shake hands". This functionality, in one example, may be supplied in part using features of the performance of cultural and conversational gestures algorithm 538b, described in relation to FIG. 5B.

In some implementations, effectiveness of the presented guidance is determined (748). For example, based upon recorded video and/or audio data, the socially relevant event identifier can identify a socially relevant response invoked by the individual and compare the response to the prompted response. This step and the following steps 748 and 750, in one example, may be performed at least in part by features of the social acceptability coach algorithm 540b, described in relation to FIG. 5B.

In some implementations, if the guidance is determined as having been effective (748) positive feedback is presented to the individual (750). The feedback, in some examples, can include visual feedback, audible feedback, and/or tactile feedback. In the particular example, a visual indication of a green check is presented in a heads up display to represent success of the subject in following through on the presented response guidance. Furthermore, in some implementations, the feedback may include triggering magnetic, energy, electrical, and/or pharmaceutical doses for enhancing pleasure signals of the individual.

Conversely, if the guidance is determined as having been ineffective (748), in some implementations, negative feedback is presented to the individual (752). In the particular example, a visual indication of a red "X" is presented in a heads up display of the wearable data collection device to represent failure of the individual in following through on the presented response guidance. Additional discussion regarding the use of feedback and selection of styles of feedback is provided in relation to the method 800 of FIG. 8.

Figure 8:
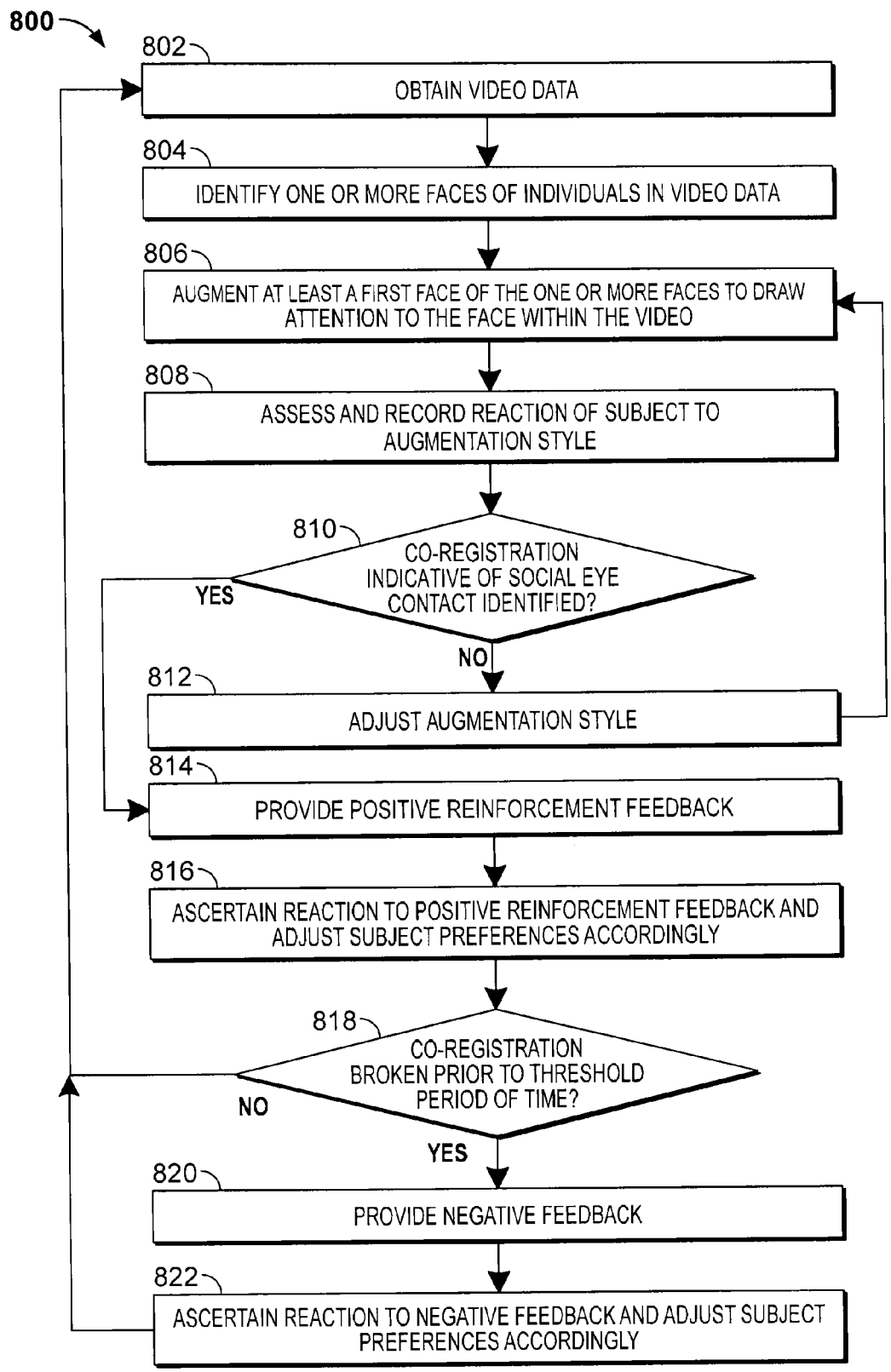
FIG. 8 is a flow chart of an example method for conditioning social eye contact response through augmented reality using a wearable data collection device.

Turning to FIG. 8, a flow chart illustrates an example method 800 for conditioning social eye contact response through augmented reality using a wearable data collection device. The method 800, for example, may incorporate a type of game or virtual reality activity aimed at conditioning a user assessed for ASD to engage in social eye contact.

In some implementations, the method 800 begins with obtaining video data (802). The video data, for example, includes images captured by a head-mounted or otherwise body-mounted camera of a vicinity surrounding the user. The video data may represent the surroundings of the user as viewed more-or-less through the eyes of the user.

In some implementations, one or more faces of individuals are identified within the video data (804). The faces, for example, can include family members, social peers, colleagues, or other people in the surroundings. Additionally, in some embodiments, the faces can include animals or inanimate objects, such as a family pet, a therapy dog, or a toy doll.

In some implementations, at least a first face of the one or more faces in captured video data is augmented to draw attention to the face within the video output to the user (806). In some examples, the face may be outlined in colors, overlaid with a shimmer, or caricatured in an animated fashion to draw the attention of the user. In other examples, silly hair may be applied to an individual identified within the video data or a distortion field applied to the face region. Alternatively or additionally, in some examples, background video surrounding the face may be dimmed, reduced in complexity, or blurred to reduce focus on any aspects in the video besides the face. In a particular example, a favorite cartoon character may be superimposed upon the face region of an individual (e.g., in an opaque or semi-transparent manner) within the video data to draw the attention of the user to the face of the individual.

Alternatively, in other implementations, faces may be removed from the video output to the user. For example, the face regions of each individual may be edited out of the video feed or supplanted with an overlay (e.g., solid color, animated grayscale noise pattern, etc.).

In some implementations, data is analyzed to identify social eye contact between the user and the first face (808). For example, as described in relation to FIG. 1A, an eye tracking module may analyze eye tracking data 116g obtained from a face-directed video capture element of the wearable data collection device to determine when the gaze of the user co-registers with the first face of the video data. In another example, video captured by a wearable data collection device worn by the other person is analyzed to determine whether the gaze of the user is directed at the face of the person. Further, in some embodiments, both the user and the other person have donned wearable data collection devices, and a straight line wireless signal, such as a Bluetooth signal, infrared signal, or RF signal, is passed between the user's wearable data collection device and the other person's wearable data collection device, such that a wireless receiver acknowledges when the two wearable data collection devices are positioned in a substantially convergent trajectory.

In some implementations, reaction of the user to the augmentation style is assessed and recorded (808). If the augmentation style failed to catch the user's attention towards the first face, for example, the first augmentation style may be recorded as being "ineffective." Conversely, if the user's attention turned towards the first face, the first augmentation style may be recorded as being "effective." In this manner, the method 800 may include a learning aspect to identify most effective methods of gaining and holding the user's attention.

In some implementations, if co-registration indicative of social eye contact between the user and one of the faces is not identified (810), an augmentation style is adjusted (812). For example, if the first augmentation style included a line surrounding the first face, the augmentation style may be adjusted to instead apply a jiggling movement to the face. In another example, if the first augmentation style included a black and white caricature version of the face, a second augmentation style may include a colorful caricature version of the face. Furthermore, augmentation style of the background scenery may be applied and/or adjusted.

In some implementations, if co-registration is identified (810), positive reinforcement feedback is provided to the user (814). Positive reinforcement feedback can include audio, visual, and/or tactile (haptic) feedback designed to reward the user for directing attention to the augmented face. Positive reinforcement feedback may include an enjoyable or celebratory sound, such as a fanfare, cheering, or happy music. Verbal positive feedback, such as the words "success", "hooray", "good job", or "way to go" may be audibly or visually presented to the user. The positive reinforcement feedback may include a color, image, animation, or other pleasing visual representation presented, for example, in the heads-up display of the wearable data collection device. In some embodiments, positive reinforcement feedback includes adding points, for example in the form of a heads-up display icon representing accumulated points, in a game-style interface. Levels of positive reinforcement may vary based upon desirability of reaction. For example, for a brief period of social eye contact, the user may be presented by pleasing sounds or other encouragement. After a threshold period of time, the positive reinforcement feedback may be enhanced to include an indication of success. For example, any social eye contact may be rewarded in part, but social eye contact for at least a threshold period of time (e.g., one second, three seconds, etc.) may be rewarded with points or a more elaborate/celebratory feedback mechanism.

In some implementations, the user's reaction to the positive reinforcement feedback is ascertained and the user's preferences adjusted accordingly (816). For example, upon presentation of positive reinforcement feedback, if the user maintains social eye contact for the threshold period of time, the particular positive reinforcement feedback provided to the user may be flagged as being effective with the user. For example, points associated with the feedback may be incremented or the feedback may be promoted within a list of feedback options. If, instead, the user terminates social eye contact with the face prior to the threshold period of time despite the use of positive reinforcement, the particular positive reinforcement feedback presented may be flagged as being ineffective with the user. For example, points associated with the feedback may be decremented or the feedback may be demoted within a list of feedback options. In this manner, the method 800 may learn the most effective manners of positive feedback for the particular user.

In some implementations, assessment of the user's reaction to the positive reinforcement feedback is ascertained in part by analyzing various data associated with the user. For example, levels of pleasure or displeasure with the currently presented feedback may be derived from reviewing a subject-pointing video recording to review relative pupil dilation, eye moistness, or eyebrow position. Further, levels of pleasure or displeasure may be derived from reviewing subject physiological data such as heart rate, breathing rate, or neurological data such as EEG/EMG/EKG data.

If, instead of maintaining co-registration for the threshold period of time, the user terminates social eye contact with the face (818), in some implementations, negative feedback is provided to the user (820). Negative feedback, for example, may be selected to discourage an undesirable behavior of the user, such as glancing briefly at the face rather than maintaining social eye contact. The negative feedback may include one or more of audible, visual, and tactile feedback. In particular examples, an irritating vibration may be applied to a point on the skin of the user or an annoying noise may be played to the user.

In some implementations, the user's reaction to the negative feedback is ascertained and the user's preferences adjusted accordingly (822). As described above in relation to step 816 regarding positive reinforcement feedback, similar analysis and promotion/demotion of negative reinforcement mechanisms may be made to learn the most effective negative feedback mechanisms to use with the user. Success of negative reinforcement mechanisms, for example, may be based in part upon how quickly the user returns his or her gaze to the face.

Figure 9:
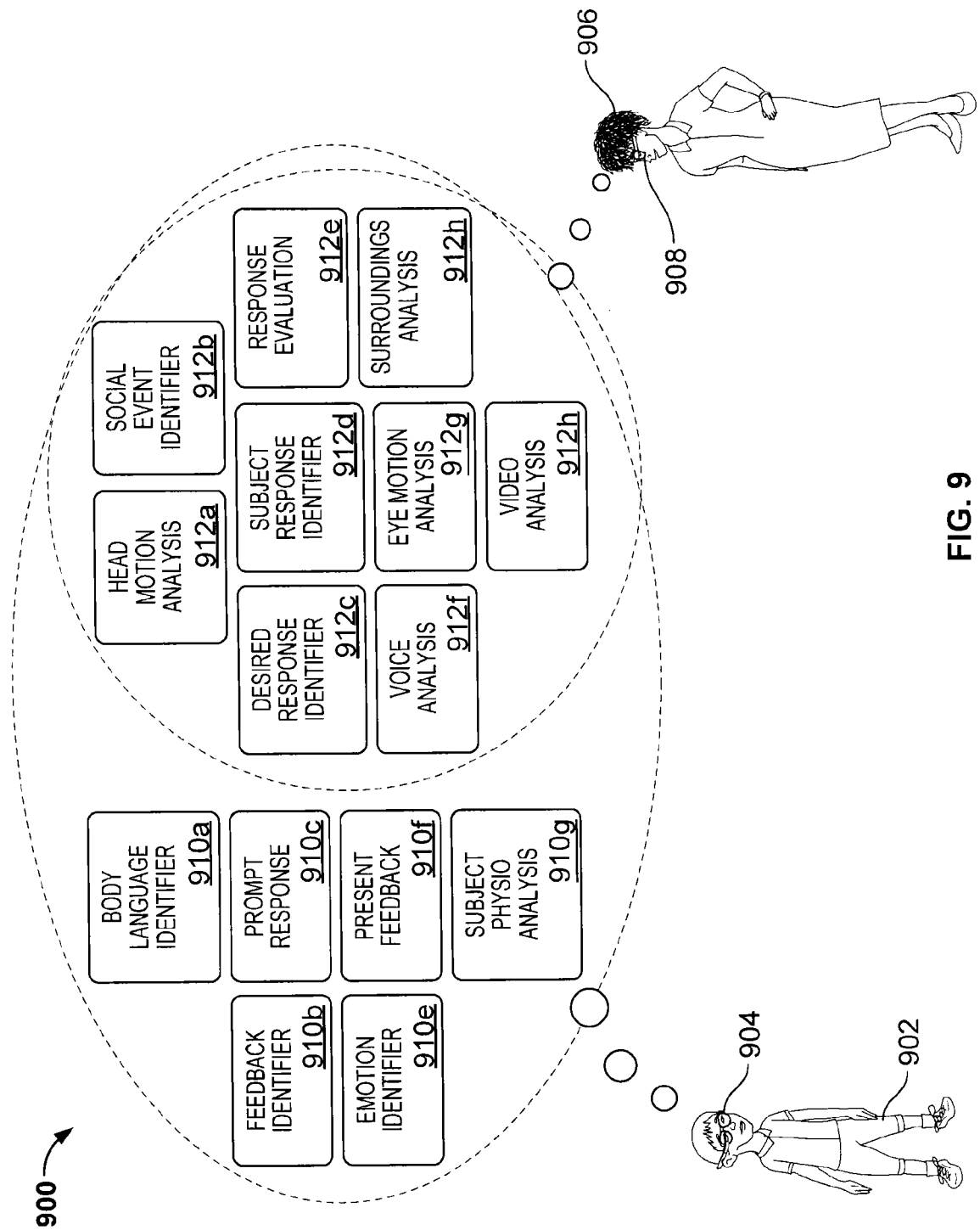
FIG. 9 is a block diagram of an example collection of software algorithms for implementing identification of and gauging reaction to socially relevant events.

FIG. 9 is a block diagram of an example collection of software algorithms 910 and 912 for implementing identification of and gauging reaction to socially relevant events. Based upon particular implementations, individual software algorithms 910 and 912 may execute upon a wearable data collection device 904 (or 906), a computing device in direct communication with the wearable data collection device 904 (or 906) such as a smart phone, tablet computer, or smart watch, or a computing system accessible to the wearable data collection device 904 (or 906) via a network connection, such as a cloud-based computing system. The subsets of the software algorithms 910 and 912, in a particular example, may be configured for performance of a software application developed for assessment and/or training of a subject with ASD.

The software algorithms 912 may differ in functionality based upon whether they are executing upon or in coordination with a wearable data collection device 904 of an individual 902 or upon or in coordination with a wearable data collection device 908 of a caregiver 906. For example, the eye motion analysis algorithm 912g designed for execution upon the caregiver wearable data collection device 908 may analyze eye motion based upon video recording data capturing the face of the individual 902, while the eye motion analysis algorithm 912g may analyze eye motion based upon a camera mechanism of the individual's wearable data collection device 904 directed at the face of the individual 902 (e.g., directed at and capturing substantially the eye region of the face of the individual 902). In another example, a head motion analysis algorithm 912a, designed for execution upon the caregiver wearable data collection device 908, may analyze movements of the head of the individual 902 based upon recorded video data of the individual 902, while the head motion analysis algorithm 912a designed for execution upon the individual's wearable data collection device 904 may analyze movements of the individual's head based upon one or more motion sensors built into the individual's wearable data collection device 904. Further, the software algorithms 910 are unique to providing features for the individual 902.

Figure 10A:
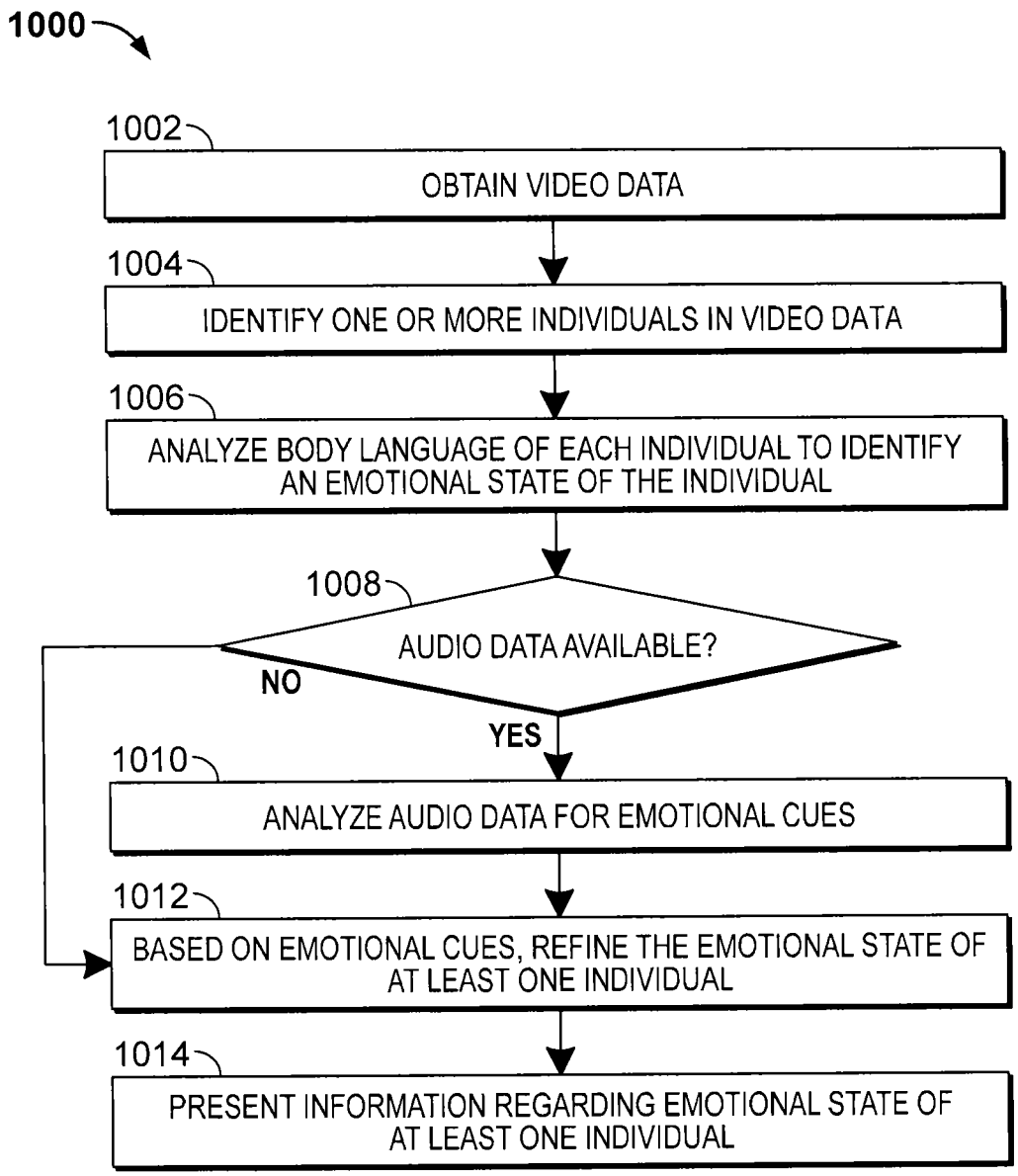
FIG. 10A is a flow chart of an example method for identifying and presenting information regarding emotional states of individuals near an individual.

The software algorithms 910 and 912, in some examples, may be used to perform portions of method 700 described in relation to FIGS. 7A through 7C, method 800 described in relation to FIG. 8, and/or method 1000 described in relation to FIG. 10A.

Further, the software algorithms 910 may be used to support functionality of one or more software algorithms designed as learning tools or behavioral management aids for the subject 902. For example, in some implementations, a timing of cultural and conversational gestures algorithm 538a (illustrated in FIG. 5B) may use the body language identifier 910a to analyze performance of cultural and conversational gestures by the individual 902. The cultural and conversational gestures algorithm 538a may provide the individual 902 with coaching and training on the timing and appropriateness of gestures such as, in some examples, handshake styles, bows, nods, smiles, and hand and arm gestures during speech. Through the emotion identifier 910e, for example, the cultural and conversational gestures algorithm 538a may identify that the caregiver 906 is smiling at the individual 902. An appropriate response would be to smile back. The subject physio analysis algorithm 910g may assess the emotional state of the individual 902 and/or determine if the individual 904 is already smiling. The prompt response algorithm 910c may be invoked by the cultural and conversational gestures algorithm 538a to prompt the individual 902 to smile. Upon recognition of a smile of the individual 904, further to the example, the present feedback algorithm 910f may be invoked to provide positive feedback to the individual 902.

Figure 5C:
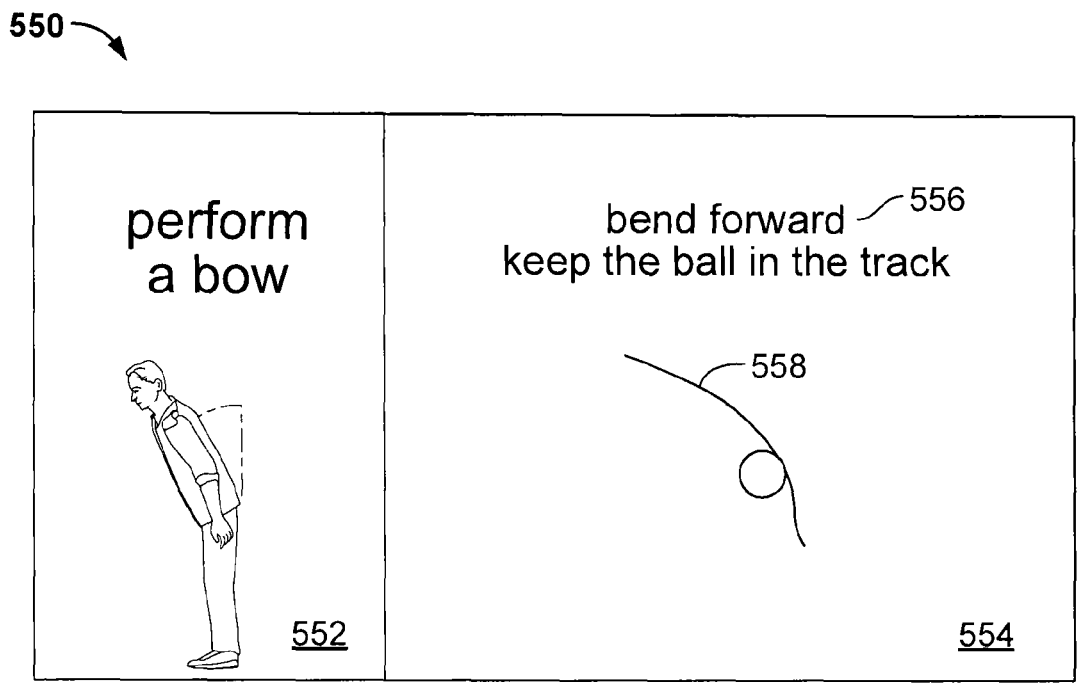
FIG. 5C is a screen shot of an example display for coaching a user in performing a bow.

In some implementations, the cultural and conversational gestures algorithm 538a of FIG. 5B may coordinate with a performance of cultural and conversational gestures algorithm 538b of FIG. 5B to train the individual 902 in proper performance of gestures involving large motions. The performance training, in some examples, may be used to coach the individual 902 in proper performance of bowing at proper depth with proper head angle, dancing postures, distress signals, sign language, and other non-verbal communication signals. In a particular example, turning to FIG. 5C, a screen shot 550 illustrates an example user interface for coaching an individual in performing a bow. An image pane 552 contains an illustration of an avatar performing a bow movement with a textual label "perform a bow", while a coaching pane 554 includes both a message 556 "bend forward keep the ball in the track" as well as an animated illustration 558. In operation, as the individual performs the bow, a ball icon portion of the animated illustration 558 will move within the image pane 552 according to sensed movements of the individual's head (e.g., based upon data provided by one or more motion sensing devices incorporated into or in communication with the wearable data collection device). If the individual maintains the ball icon portion of the animated illustration 558 substantially following a path portion of the animated illustration 558, the individual's body will appropriately perform the gesture of the bow. In other implementations, additional sensor data captured from sensors upon the individual's body may be analyzed to validate positioning and motion corresponding to the motion of the head of the individual such as, in some examples, a motion sensor attached to a wrist-mounted device validating that at least one of the individual's hands is positioned at his or her side. Although illustrated as a two-dimensional coaching animation, in other implementations, the visual display may present a three-dimensional animated graphic for guiding the individual through proper performance of the gesture. Further, in other embodiments, the avatar icon may be replaced by an animated illustration or video demonstration of the gesture.

Returning to FIG. 9, aspects of the cultural and conversational gestures algorithm 538a, in some implementations, are used to coach the individual 902 in martial arts movements and techniques, yoga postures, role-playing game and re-enactment motions, fighting or defense techniques, and other controlled physical gestures. In further implementations, aspects of the cultural and conversational gestures algorithm 538a are used to provide quantification and feedback for anomalous body motions such as in dystonia or Parkinson's Disease and Huntington's Disease or motor ticks. Similar to the cultural and conversational gestures algorithm 538a, the performance of cultural and conversational gestures algorithm 538b may coordinate with the body language identifier algorithm 910a. For example, the cultural and conversational gestures algorithm 538a may invoke the body language identifier algorithm 910a in support of identifying opportunities for performing a large motion gesture, and the cultural and conversational gestures algorithm 538a, responsive to identifying an opportunity, may invoke the performance of cultural and conversational gestures algorithm 538b to coach the individual 902 in performing the gesture.

Although the cultural and conversational gestures algorithm 538a and the performance of cultural and conversational gestures algorithm 538b are described in relation to interactions with another person, in some implementations, the individual 902 may invoke the algorithms 538a and/or 538b for practice mode training in cultural and conversational gestures.

In some implementations, a personal distance coach algorithm 542a of FIG. 5B provides the individual 902 with a tool for coaching appropriate distance to maintain when interacting with another person, such as the caregiver 906. The personal distance coach algorithm 542a, for example, may review video data such as video recording data 116b described in relation to FIG. 1A to estimate distance between the individual 902 and another person. For example, the personal distance coach algorithm 542a may estimate distance based upon depth cues and parallax cues in the video recording data 116b. In another example, a signal transmitted between the individual's wearable data collection device 904 and the caregiver's wearable data collection device 906 may be used to measure a present distance. In a further example, distance may be estimated based upon reflection of signals using a laser or sound-based system of the wearable data collection device 904.

In some implementations, the emotion identifier module 910e may contribute to assessment of appropriate distance by gauging a level of comfort of the person communicating with the individual 902, such as the caregiver 906. In one example, the level of comfort of the person communicating with the individual 902 may be based upon an estimated emotional state of the other member of the interaction by invoking the emotion identifier algorithm 910e. In another example, the level of comfort of the person communicating with the individual 902 may be based upon a posture of the other member of the interaction by invoking the body language identifier 910a.

The personal distance coach algorithm 542a, in some implementations, factors in the distance between the individual 902 and the other member of the interaction, the estimated emotional state and/or posture cues of the other member of the interaction, and, potentially, information related to cultural norms (e.g., geographic, racial, religious, etc.) to determine appropriateness of the current personal distance. The personal distance coach algorithm 542a may invoke the prompt response algorithm 910c to prompt the individual 902 to adjust a present distance accordingly.

A turn-taking algorithm 542b of FIG. 5B, in some implementations, monitors conversation and calculates a relative amount of time that the individual is contributing to a conversation in relation to the amount of time each other member of the interaction is speaking. Individuals diagnosed with ASD are frequently quiet and remiss to contribute to conversations, while other individuals diagnosed with ASD will talk on at length without providing opportunity for others to contribute to the discussion. Through reviewing audio data collected by the individual's wearable data collection device 904, such as audio recording data 116a described in relation to FIG. 1A, the turn-taking algorithm 542b may prompt the individual 902a to speak up or, conversely, to politely pause to allow another member of the conversation to jump in. Further, the turn-taking algorithm 542b may monitor appropriate turn-taking during a period of time, tracking progress of the individual 902.

Figure 5D:
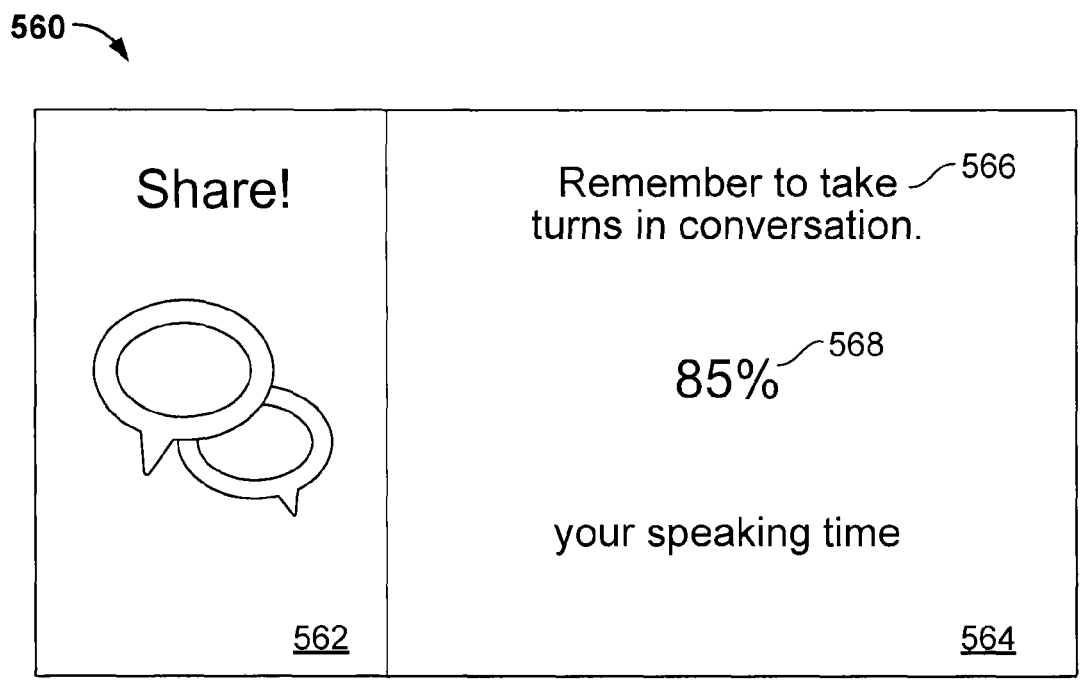
FIG. 5D is a screen shot of an example display for providing conversation skill feedback to a user.

Turning to FIG. 5D, in some implementations, the turn-taking algorithm 542b presents visual feedback, such as the feedback user interface presented within a screen shot 560. As illustrated in the screen shot 560, a topic pane 562 contains an illustration of a speech bubble icon with the textual label "Share!", while a feedback pane 564 includes both a message 566 "Remember to take turns in conversation" as well as statistical feedback 568 representing a percentage time that the individual has dominated the conversation (e.g., illustrated as 85% and labeled "your speaking time"). The screen shot 560, for example, may be presented within a heads up display of a wearable data collection device to prompt a user to take turns in conversations with other members of the conversation.

Returning to FIG. 9, in some implementations, the turn-taking algorithm 542b generates a report regarding the individual's progress in conversational turn-taking. The report, for example, may be generated on a periodic basis and supplied to a caregiver, medical practitioner, educator, or other person tasked with assessing the progress of the individual 902.

FIG. 10A is a flow chart of an example method 1000 for identifying and presenting information regarding emotional states of individuals near a user. Individuals living with ASD frequently struggle with identifying and reaction appropriately to emotional states of others. The method 1000 can support understanding by an ASD individual of the emotional states of those around them and appropriate response thereto through automated identification of emotional states of nearby individuals.

In some implementations, the method 1000 begins with obtaining video data (1002). The video data, for example, may include images captured by a head-mounted or otherwise body-mounted camera of a vicinity surrounding a user. The video data may represent the surroundings of a user as viewed more-or-less through the eyes of the user. In one example, the video data is video recording data 116a captured by the wearable data collection device 104, as described in relation to FIG. 1A.

Figure 10B:
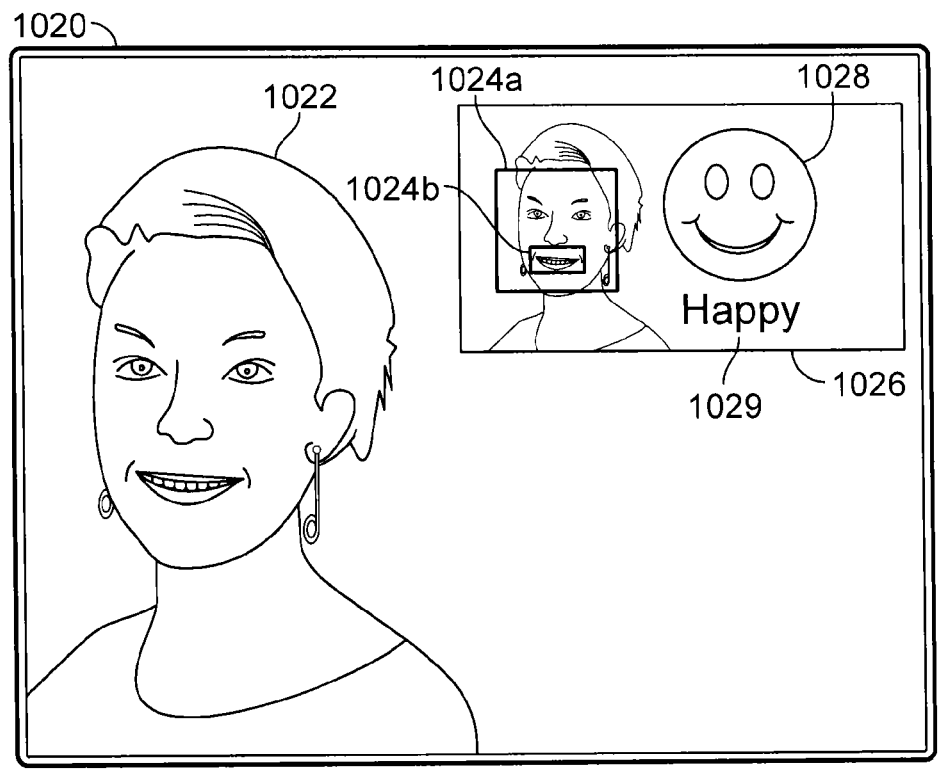
FIGS. 10B and 10C are screen shots of example user interfaces for identifying and presenting information regarding emotional states of an individual based upon facial expression.

In some implementations, one or more individuals are identified within the video data (1004). The individuals, for example, can include family members, social peers, colleagues, or other people in the surroundings. Additionally, in some embodiments, the individuals can include animals, such as a family pet or a therapy dog. For example, as illustrated in FIG. 10B, an individual 1022 is identified within video data, as illustrated in a screen shot 1020.

In some implementations, for each individual identified, body language is analyzed to identify the emotional state of the individual (1006). For example, an emotional identification and training module may review an individual's posture, including head position, arm position, and hand gestures or other gestures (e.g., hugging, self-hugging, cheek stroking, head scratching, head holding, high-fiving, fist-bumping, patting another on the shoulder) for evidence of body language associated with a particular emotion. In another example, the emotional identification and training module may review an individual's facial expression, including mouth shape, eyebrow position, pupil dilation, eye moistness, and other facial cues regarding emotional state. Turning to FIG. 10B, for example, the emotional identification and training module has identified both a face (designated by a focus frame 1024a) of the individual 1022 and a mouth position 1026 (designated by a focus frame 1024b) of the individual 1022, as illustrated in an analysis pane 1026. Returning to FIG. 10A, the emotional identification and training module may also review body dynamics such as, in some examples, trembling, bouncing, shaking, rocking, or other motions associated with emotional state.

If audio data is available (1008), in some implementations, the audio data is analyzed for emotional cues (1010). For example, the emotional identification and training module may extract audio associated with verbalizations of a particular individual identified within the video recording data. The audio may be reviewed for tone, volume, pitch, patterns in pitch (e.g., sing-song, questioning, etc.), vocal tremors, sobbing, hiccuping, laughing, giggling, snorting, sniffing, and other verbalizations and/or intonations that may be associated with emotional state. In some implementations, the emotional identification and training module may further identify one or more emotional words or phrases within the audio data.

In some implementations, the audio-derived emotional cues are applied to the identified emotional state(s) to refine the emotional state of at least one individual (1012). For example, if the emotional state of the individual, based upon video analysis alone, suggested two or more potential emotional states, the audio-derived emotional cues may be used to promote or demote the various options to identify a most likely emotional state candidate. In other implementations, for example if the audio-derived emotional cues are more reliable because the video is obscured or the individual is not facing the camera, the audio-derived emotional cues may be used as primary reference or sole reference to determine the emotional state of at least one individual.

In some implementations, information regarding the emotional state of at least one individual is presented to a user (1014). For example, a feedback algorithm may augment the video feed of a heads-up display of a data collection device to overlay a description of the emotional state of the individual, such as the word "irritated" floating above the individual's head or a simplified cartoon icon representing an emotional state such as bored, happy, tired, or angry may supplant the individual's face in the heads-up display or hover hear the individual's face within the heads-up display. As illustrated in the screen shot 10B, for example, an icon 1028 representing the emotional state of the individual 1022, as well as a label 1029 ("happy"), are presented within the analysis pane 1026. Alternatively or individually, a term or sentence for the emotional state may be presented audibly to the user, such as "mom is happy." Further, audio or video feedback may spell out to the user the particular response behavior to invoke, such as an audible cue directing the subject to "smile now" or a visual cue including the text "nod your head and look concerned." If the individual is an animal, the user may be presented with verbal and/or audible warnings, such as "may bite" or "back away".

Figure 10C:
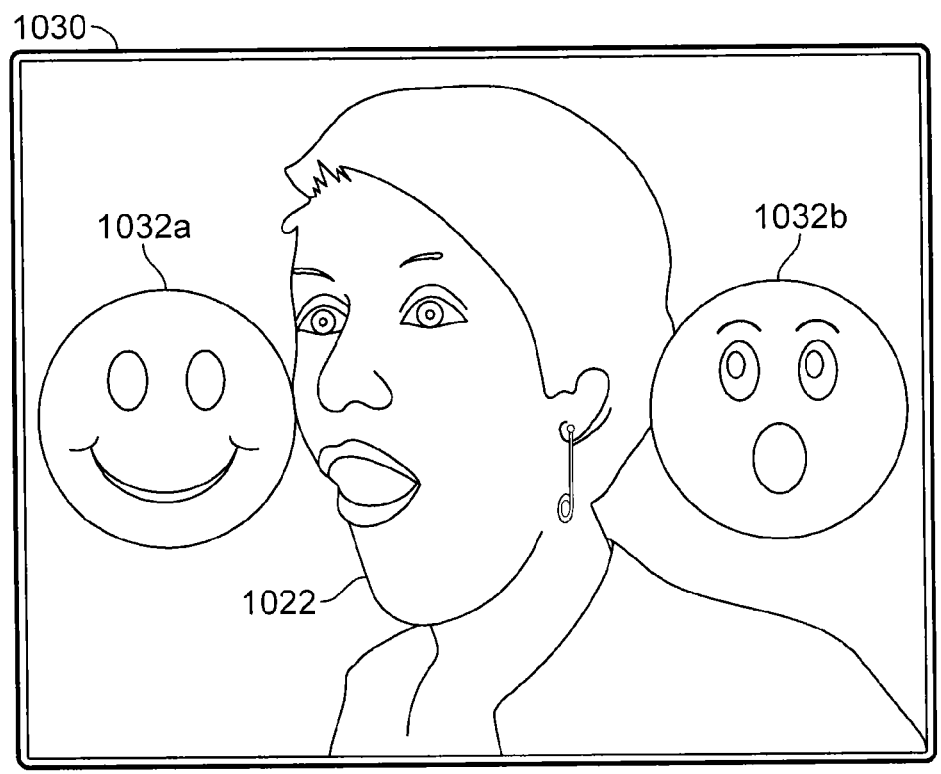

In some implementations, rather than presenting an emotional state of the individual, the application may take a form of a game, where the user is presented with a multiple choice selection of three potential emotional states. In this manner, the user may be quizzed to pay close attention to learning physical and audible cues identifying emotional states. Further, based upon the user's responses, an emotional state awareness tracking module may learn which emotional states are difficult for the user to identify or whose emotional states are difficult for the user to identify. For example, the user may have difficulty recognizing emotional states of bearded men. To aid in recognition, feedback to the user may include hints for identifying particular emotional states, such as "raised eyebrows indicate surprise". Turning to FIG. 10C, for example, a screen shot 1030 including the individual 1022 includes a set of selectable emoticons 1032, were emoticon 1032a represents a happy emotional state and emoticon 1032b represents a surprised emotional state. The user may select one of the emoticons 1032 (e.g., through an input device of a wearable data collection device such as a tap, head movement, verbal command, or thought pattern). The game may then present feedback to the user to correct or congratulate the user, based upon a selected emoticon 1032.

Although described in a particular series of steps, in other implementations, the method 1000 may be performed in a different order, or one or more steps of the method 1000 may be removed or added, while remaining in the spirit and scope of the method 1000. For example, rather than analyzing live video data and presenting information related to emotion, in some implementations, the method 1000 may be adjusted to present a review exercise incorporating images of people that the individual interacted with recently (e.g., in the past hour, day, week, etc.). In a familiar faces review exercise module, for example, aspects of the method 1000 may be used to quiz the individual on emotional states represented by images or short video segments of one or more faces identified in video data captured by the wearable data collection device. By using short video segments rather than still images, for example, the familiar faces review exercise module may allow the individual to derive emotional cues from body language, vocalizations, and other additional information.

Figure 11A:
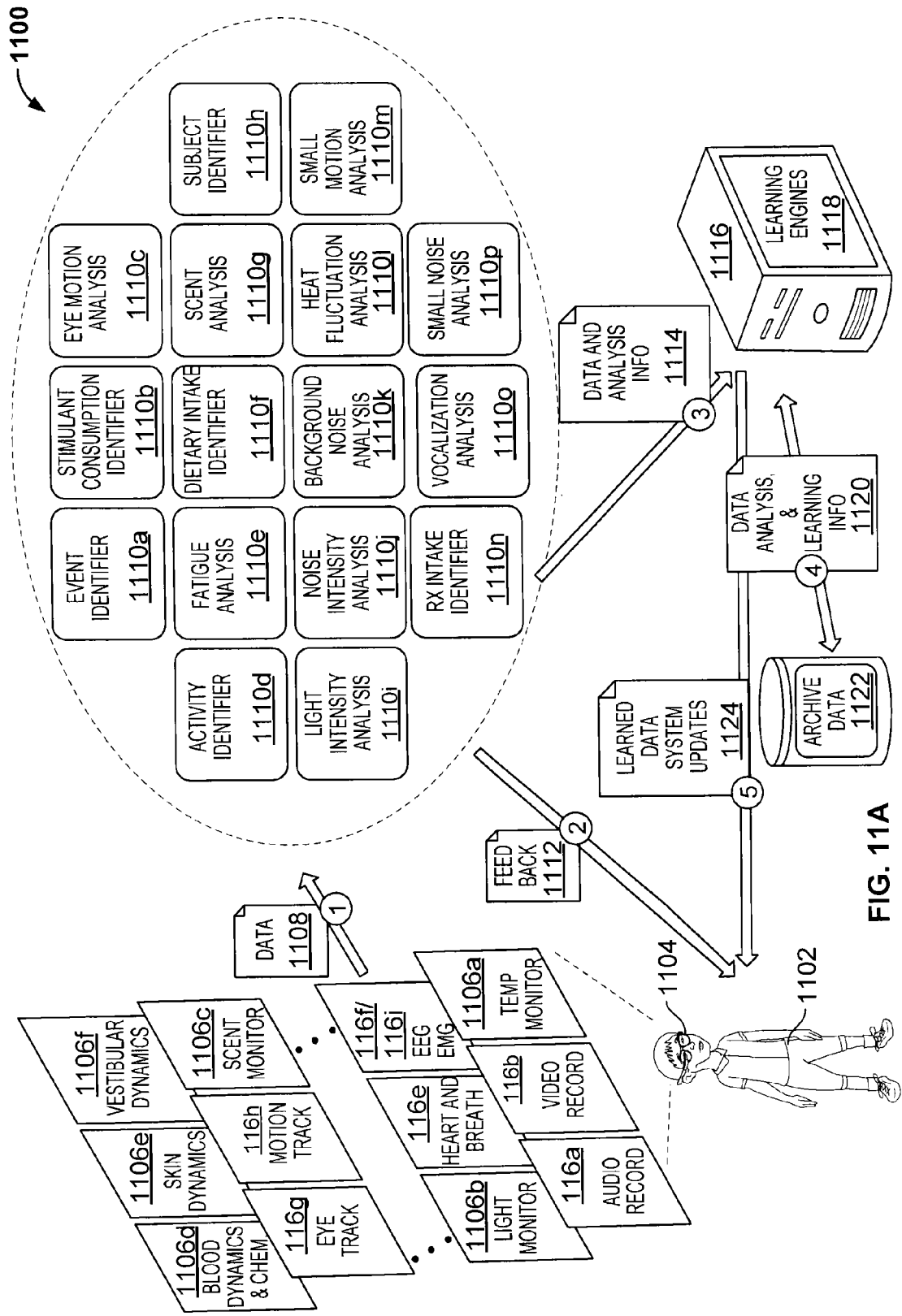
FIG. 11A is a block diagram of an example system for identifying and analyzing circumstances surrounding adverse health events and/or atypical behavioral episodes and for learning potential triggers thereof.

FIG. 11A is a block diagram of an example system 1100 for identifying and analyzing circumstances surrounding adverse health events and/or atypical behavioral episodes and for learning potential triggers thereof. The system 1100 may analyze factors surrounding the onset of adverse health events and/or atypical behavioral episodes to anticipate future events. The factors may include, in some examples, dietary factors, fatigue, light sensitivity, noise sensitivity, olfactory sensitivity, and prescription and/or over-the-counter drug consumption patterns. Adverse health events, for example, may include migraine headaches, epileptic seizures, heart attack, stroke, and/or narcoleptic "sleep attacks". Particular individuals may be monitored for adverse events related to known health conditions, such as individuals in congestive heart failure or in presence of aneurysm, individuals recovering from stroke, or individuals suffering from cardiac disease, diabetes, or hypo/hypertension. Further, individuals may be monitored due to psychiatric conditions such as panic disorders. Atypical behavioral episodes may include, in some examples, swings in manic-depressive behavior or bipolar behavior, emotional outbursts triggered by post-traumatic stress disorder (PTSD), and acting out or stimming episodes related to ASD.

In another aspect, the example system 1100 may be used to measure motions and vibrations associated with recurring transitory physiological patterns (e.g., physiological states and events). The recurring transitory physiological patterns, in some examples, may include a slow-wave change within physical motions of the individual or a pronounced head motion pattern of the individual. Pronounced head motion patterns, in some examples, may be indicative of specific heart defects, neurodegenerative conditions, or types of cardiac disease. Slow-wave changes may be indicative of temporary conditions such as intoxication, fatigue, and/or narcotic ingestion as well as temporary or periodic normal events, such as ovulation, pregnancy, and sexual arousal. Particular individuals may be monitored for recurring transitory physiological states and events, in some examples, to aid in diagnosis of balance problems, cardiac abnormalities, or neurodegenerative conditions. Further, the motion and vibration measurements may be used to monitor chronic normal events in individuals, such as heart rate and breathing rate.

An individual 1102 wears or otherwise carries a data collection device 1104, such as the wearable data collection device 104 or 108 described in relation to FIGS. 1A and 1B. In further examples, the data collection device 1104 may be incorporated in a general purpose personal electronics device such as a smart phone, tablet computer, or smart watch or in a specialized health and fitness computing device such as a Fitbit® wireless activity monitor by Fitbit, Inc. of San Francisco, Calif. The data collection device 1104 is configured for collection of various data 116, including, in some illustrated examples, audio recording data 116a, video recording data 116b, EEG data 116f, EMG data 116i, heart and breathing data 116e, motion tracking data 116h, and eye tracking data 116g, as discussed in relation to FIGS. 1A and 1B. Furthermore, in some implementations, the data collection device 1104 may be configured to collect temperature monitoring data 1106a, including a skin or body temperature of the individual 1102 and/or ambient temperatures of the area surrounding the individual 1102. In some implementations, the data collection device 1104 may be configured to collect light monitoring data 1106b, for example as derived from a camera device or simpler light sensor. Scent monitoring data 1106c may identify various fragrances in the vicinity of the individual 1102. Enhanced physiological data monitoring of the data collection device 1104, in some examples, may include blood dynamics and chemistry data 1106d (pulse oximetry, blood flow or volume changes, etc.), skin dynamics data 1106e (galvanic skin response and skin conductance response measurements, etc.), and vestibular dynamics data 1106f used to monitor the movements of the individual 1102 to gauge whether they are standing upright versus falling or wobbling and gyrating, such as a horizon monitor in combination with a motion monitor.

Data 1108 collected by the wearable or portable data collection device 1104 (and, potentially, data collected by peripheral devices in communication with the data collection device 1104), in some implementations, are used by a number of algorithms 1110 developed to analyze the data 1108 and determine feedback 1112 to provide to the individual 1102 (e.g., via the data collection device 1104 or another computing device). The algorithms 1110 may further generate analysis information 1114 to supply, along with at least a portion of the data 1108, to learning engines 1118. The analysis information 1114 and data 1108, along with learning information 1120 generated by the learning engines 1118, may be archived as archive data 1122 for future use, such as for pooled statistical learning. The learning engines 1118, furthermore, may provide learned data 1124 and, potentially, other system updates for use by the data collection device 1104 or the subject 1102 (e.g., through a software application for presenting crowd-sourced feedback and data analysis). The learned data, for example, may be used by one or more of the algorithms 1110 executed upon the data collection device 1104. A portion or all of the algorithms 1110, for example, may execute upon the data collection device 1104. Conversely, in some implementations, a portion or all of the algorithms 1110 are external to the data collection device 1104. For example, certain algorithms 1104 may reside upon a computing device in communication with the data collection device 1104, such as a smart phone, smart watch, tablet computer, or other personal computing device in the vicinity of the individual 1102 (e.g., belonging to a caregiver, owned by the individual 1102, etc.). Certain algorithms 1110, in another example, may reside upon a computing system accessible to the data collection device 1104 via a network connection, such as a cloud-based processing system.

The algorithms 1110 represent a sampling of potential algorithms available to the data collection device 1104. The algorithms 1104 may vary based upon the goal of a particular implementation. For example, a first set of algorithms may be used to anticipate migraine headaches, while a second set of algorithms are used to anticipate ASD-related acting out events. Basic to anticipation of events or atypical behavior episodes is an event identifier algorithm 1110a, configured to recognize occurrence of an adverse event or episode. Data collected by the data collection device 1104 immediately leading to and during the event identified by the event identifier algorithm 1110a, for example, may be presented to the learning engines 1118 for review and analysis.

Based upon data collected regarding the individual 1102 and, optionally, additional individuals having the same disorder and potentially sharing similarities of symptoms, the learning engines 1118 may derive correspondence between events and one or more corresponding factors. Many of the algorithms 1110 are designed to identify factors which may contribute to one or more health events. For example, an activity identification algorithm 1110d identifies activities the individual 1102 is engaged in such as, in some examples, driving, watching television, eating, sleeping, bicycling, working out at a gym, working at a computer, reading a book, and tooth brushing. The activity identification algorithm 1110d, in some implementations, provides information to a fatigue analysis algorithm 1110e which monitors sleep patterns and/or other symptoms of fatigue (e.g., skin temperature data 1106a, EEG data 116f and/or EMG data 116i, heart and breathing data 116e, etc.).

Certain algorithms 1110, in some implementations, are designed to monitor consumption factors. For example, a stimulant consumption identification algorithm 1110b may identify consumption of caffeinated beverages, such as coffee and soda, while a dietary intake identification algorithm 1110f may identify consumption of various types of foods. The stimulant consumption identification algorithm 1110b and/or the dietary intake identification algorithm 1110f, in some implementations, identifies food "objects" through data learned by the learning and data analysis modules 520 described in relation to FIG. 5A towards object identification. For example, label scanning capabilities as described in relation to object identification in FIG. 5A may be used to identify packaged food items (e.g., bottles of soda, etc.) and identify ingredients within packaged food items which may prove to be triggers (e.g., aspartame, monosodium glutamate, etc.). Further, the prescription intake identification algorithm 1110n may use one or more label scanning capabilities, described in relation to FIG. 5A, to identify prescription or over-the-counter drug consumption.

In monitoring consumption factors, in some implementations, the learning engines 1118 may include a dietary intake analysis module for tracking (or estimating) consumption factors such as, in some examples, calories, vitamins, minerals, food category balance, fats, sugars, salt, and/or fluid volume. Based upon video recording data 116b, for example, the dietary intake identification algorithm 1110f may estimate (from relative sizes of items within an image) a portion of various foods consumed by the individual 1102. For example, the dietary intake identification algorithm 1110f may recognize, through label scanning, dietary intake analysis of a prepackaged food item. Additionally, the dietary intake identifier may recognize the consumption of an apple. A learning engine 1118 may correlate a medium-sized apple with a particular intake analysis, as well as logging the apple as belonging to the fruits food group.

Food intake data collected by the dietary intake identifier 1110f and analyzed by one of the learning engines 1118, in some implementations, may be provided to the individual 1102 via feedback 1112, for example, to aid in healthy eating choices and weight loss monitoring. In another example, food intake data may be provided to a caregiver, personal coach, or health professional for review in relation to treatment of a health condition, such as hypertension.

In some implementations, a portion of the algorithms 1110 are designed to monitor triggering factors such as, in some examples: loud, irritating, or potentially frightening noises via a noise intensity analysis algorithm 1110i; strobing, intense, or unusually colored ambient light via a light intensity analysis algorithm 1110j; subtle but potentially aggravating noises via a background noise analysis algorithm 1110k, and strong or potentially evocative scents via a scent analysis algorithm 1110g (e.g., fed by scent data 1106c collected by a scent monitor). In the example of ASD, a potential trigger includes vowel-consonant boundary analysis to identify when nearby speakers may be mumbling or slurring words. The vowel-consonant boundary analysis, furthermore, can indicate the state of the individual 1102, such as contributing to fatigue analysis 1110e or identifying a drugged state (e.g., building into the prescription intake identifier 1110n).

In some implementations, a portion of the algorithms 1110 are designed to monitor for physiological factors leading to an event. For example, a vocalization analysis algorithm 1110o may identify voice fluctuation patterns that may later be identified (e.g., by the learning engines 1118) to commonly precede adverse health events. EMG data 116i and/or EEG data 116f may further be analyzed by the learning engines 1118 to identify neurological data patterns commonly preceding events. Algorithms 1110 may then be designed to identify the advent of such neurological data patterns.

In some implementations, rather than collecting EMG data 116i and/or EEG data 116f, the data collection device 1104 is designed to indirectly monitor cardiovascular dynamics to reveal underlying physiological functions. The core principle is the following: when the heart beats, an impulse-wave of blood courses through the body via the vasculature. As the impulse travels through the body, the body actually moves, physically. Certain parts, such as extremities, move in more pronounced ways. The head, for instance, moves in a bobble fashion, perhaps in part because the exquisite joints of the neck allow many degrees of freedom of motion and because the head is weighty and receives a large amount of the force of traveling blood and because muscles in the neck serve to stabilize the head and may cause reverberations with each beat. This may result in particularly pronounced head motions in the case of anomalous heart beats, such as in disease or sudden exertion, if the musculature evolved and learned to accommodate for healthy and statistically more frequent heart beat and pulse-wave dynamics. Specific heart defects or types of cardiac disease typically result in anomalous head motions. In one example, a different pronounced head pattern corresponds to atrial failure as compared to the pronounced head pattern corresponding to ventricular failure.

A portion of the algorithms 1110, thus, may be designed to indirectly measure physiological dynamics of the body, such as heart rate and cardiovascular dynamics by means of motion sensors, such as one or more accelerometers, gyroscopes, magnetometers, gravity sensors, and/or linear accelerometers. The motion sensors may be positioned at strategic points on the body of the individual 1102 such as on the head or at other extremities. Various configurations and deployments of motion sensors may include standalone motion sensors, one or more motion sensors incorporated into a separate device, and one or more sensors incorporated into the wearable data collection device 1104. The wearable data collection device 1104, for example, may be head-mounted, incorporating a number of sensors feeding data to a small motion analysis algorithm 1110m to derive cardiovascular dynamics information. The small motion analysis algorithm 1110m, for example, may be designed to measure motions of the body, especially body parts distant from the heart, that are secondary to actual heart (muscular) motions. For example, the small motions may relate to flow dynamics of blood, impulse waves in the vascular system related to heart contractions (healthy or atypical), motions related to muscular contractions in the body functioning as part of bodily systems to control and counteract pulse-related motions (e.g., such as pulses in the neck region, temples, etc.), and/or other related motions.

In some implementations, a body motion analysis system includes number of algorithms 1110 as well as one or more learning engines 1118 to extract physiological-motion data and to interpret the physiological-motion data. For example, the small motion analysis algorithm 1110m separates motions related to relevant physiological events (such as heart beats or breaths, among other possible physiological target motions) from other motions (such as those from walking or gestures). The motions, in some examples, may be derived from one or more motion sensors, small noise analysis of small noises indicative of motion, and/or motion analysis of visual data captured by one or more video capture elements such as video data 116b. An additional algorithm 1110 or learning engine 1118 component of the body motion analysis system, further to the example, receives physiological event motion data from the extraction component and operates on the information, in order to reveal physiological information such as heart dynamics or breathing dynamics.

In a simple illustrative example, the wearable data collection device 1102 includes an inertial measurement unit (IMU) sensor system such as an accelerometer and gyro complex, integrated directly with hardware and software drivers. While worn by the individual 1102, the sensor system physically moves with the head with the pulsatile motion of the blood coursing through, e.g., the carotid and cerebral arteries (the "ballistocardiogram"). The sensor system, further to the example, may be directly attached to a sensor driver complex including a printed circuit board with components that drive the IMU and acquire data from it, an analysis unit, and a power source.

In another illustrative example, the wearable data collection device 1102 includes a video recording device, integrated directly with hardware and software drivers. While worn by the individual 1102, the video camera physically moves with the head while recording. Pronounced head motion patterns and/or slow-wave changes may be identified through analysis of the motions captured within the video data. While disabling lens stabilization may aid in identifying small motions via image capture, even when a lens stabilization system is in place, a small motion signature related to the lens stabilization system itself may be detected and effectively removed or compensated for when monitoring for small motion data related to the individual. Additionally, while identifying and monitoring pronounced head motion patterns and/or slow-wave changes, movements outside the range of compensation boundaries of the lens stabilization system (e.g., medium-sized motions of the individual) may result a reaction of the lens stabilization system (such as in a resetting of the lens stabilization system, etc.) recognized as being indicative of a particular motion of the individual.

In some implementations, to allow the data collection device 1104 to collect physiological data based upon small motions, the individual 1102 first calibrates the data collection device 1104 to identify the pulse or breathing patterns through motion data. For example, if the data collection device 1104 includes a portable personal electronics device such as a smart phone, the individual 1102 may hold the data collection device 1104 at arm's length while aiming a camera lens at his face to determine pulse, and calibrate motion-based one. For the wearable data collection device 1104 with a face-presenting camera device, in another example, a calibration mode may include standing quietly and still while the data collection device 1104 calibrates based on motions identified via the face-presenting camera.

In addition to motion sensors, other sensors incorporated into the data collection device, in some implementations, are used to derive small motion data. For example, the small motion analysis algorithm 1110*m* may analyze video recording data 116*b* to interpret deflections of a head-mounted camera as motions indicative of heartbeat, or sinusoidal arc motions as breathing. In another example, a laser sensor, for example incorporating interferometry readings, may be used to sense small motions. A light sensor collecting light monitoring data 1106*b*, for example, may provide interferometry data for the analysis. In a further example, an electromagnetic sensor may be used to infer motion data based upon disruptions of electromagnetic fields proximate to the sensor.

In some implementations, additional data sources may be used to infer cardiovascular dynamics data. For example, a heat fluctuation analysis algorithm 1110*l* may measure heat fluctuations related to small motions of the body. These heat fluctuations, for example, may be related to cardiovascular or other dynamics. Heat fluctuations may be measured by any number of available heat measurement devices for surface and radiant heat, including commercially available thermometers, thermistors, digital heat sensors, and other temperature sensors as well as devices or elements thereof having thermoelectric and pyroelectric materials and/or generators. When incorporating thermoelectric and pyroelectric materials, the wearable data collection device 1104 may further be configured to collect heat energy as a supplemental source of power for charging a battery system of the wearable data collection device 1104 and/or one or more peripheral devices. In an example configuration, the wearable data collection device 1104 may include a heat measurement device such as a far-infrared camera or sensor mounted proximate to the face of the individual 1102 and separated by a small distance (e.g., mounted on a short stalk extending from the wearable data collection device 1104), with a line of sight to the facial skin or other bodily skin. In another example, a small noise analysis algorithm 1110*p* may "listen" for breathing and/or other small sounds associated with heart beat or pulse, such as, in some examples, blood blockages or lung congestion. The small noise analysis algorithm 1110*p*, in a further example, may "listen" for sounds associated with small body motions that result from the pulse and/or breathing. The small sounds, for example, may be measured by one or more bone conduction microphones. An eye motion analysis algorithm 1110*c*, in a further example, may analyze eyelid dynamics (blinks, winks, twitches, etc.), and/or eye movement dynamics (e.g., saccades, smooth pursuit movements, vergence movements, vestibulo-ocular movements, vibrations of the eye, changes in pupil dilation, etc.).

Using the data collected by the small motion analysis algorithm 1110*m*, eye motion analysis algorithm 1110*c*, heat fluctuation analysis algorithm 1110*l*, and/or small noise analysis algorithm 1110*p*, in some implementations, one or more learning engines 1118 may infer a variety of physiological data. The physiological data can include heart dynamics such as, in some examples, heart rate, heart rate variability, QRS complex dynamics, heart beat amplitude, or murmur, and fibrillation. Further, the physiological data can include breathing dynamics such as breathing depth, breathing rate, and identification of yawning (e.g., potentially feeding back to the fatigue analysis algorithm 1110*e*). Other possible extensions include gut dynamics, body motions associated with seizures or autistic tantrums, and cerebral blood flow dynamics (e.g., providing insight into brain dynamics).

Using the data collected by the small motion analysis algorithm 1110*m*, eye motion analysis algorithm 1110*c*, heat fluctuation analysis algorithm 1110*l*, and/or small noise analysis algorithm 1110*p*, in some implementations, one or more learning engines 1118 may infer information related to various unwellness conditions or health states. The unwellness conditions can include, in some examples, neurodegenerative conditions such as Huntington's Disease, Alzheimer's Disease, Parkinson's Disease, prion diseases, other spongiform encephalopathies, or other neurodegenerative conditions, as well as other neural conditions such as dystonia.

For instance, in the case of Parkinson's Disease, the wearable data collection device 1104 may be configured to collect data, using the small motion analysis algorithm 1110*m* and/or other algorithms 1110, related to rhythmic, side-to side and rotational head motions that are characteristic of the condition. Further, the learning engines 1118 corresponding to the Parkinson's Disease condition may apply pattern analysis and/or other analysis to identify variance(s) in those motions corresponding to data capture-related metadata such as, in some examples, time of day of data capture, location at time of capture, etc. Further, the learning engines 1118 may correlate collected data to subject clinical data, such as contemporaneous medical interventions and/or medication schedule (e.g., accessed from a separate system and/or identified by the prescription intake identifying algorithm 1110*n*). In an additional example, the learning engines 1118 may correlate small motion data with data obtained through other algorithms 1110 such as, in some examples, diet data collected by the dietary intake identifier 1110*f*, activity data collected by the activity identifier 1110*d*, mental tasks and engagement cues collected, for example, by the fatigue analysis algorithm 1110*e*, eye motion analysis algorithm 1110*c*, and/or vocalization analysis algorithm 1110*o*, and/or environmental conditions and events collected by the noise intensity analysis algorithm 1110*j*, event identifier 1110*a*, and/or scent analysis algorithm 1110*g*. Further, additional algorithms 1110 and/or external data may provide cyclical fluctuation data such as circadian rhythms and/or seasonal rhythms for correlation with the small motion data by the learning engines 1118. Although described in relation to the various algorithms 1110, in other implementations, data may be accessed form a separate system (e.g., such as a patient information portal connecting the learning engines 1118 to user medical records), input directly by the wearer, and/or input to an independent software application accessed by a caregiver, physician, or other individual.

In some implementations, small motion data collected by the wearable data collection device 1104 (e.g., via algorithms such as the small motion analysis algorithm 1110*m*, eye motion analysis algorithm 1110*c*, heat fluctuation analysis algorithm 1110*l*, and/or small noise analysis algorithm 1110*p*) may be used to assist in diagnosis of an unwellness condition such as Parkinson's. For example, a practitioner may employ the wearable data collection device 1104 as a tool for gathering information regarding an individual outside of a clinician's office. The individual, for example, may be instructed to don the wearable data collection device 1104 for a certain period of time to provide data to the practitioner in identifying an unwellness condition or stage/progression of the unwellness condition. The learning engines 1118 may include a diagnosis support module configured to identify similarities between data patterns collected by the wearable data collection device 1104 and physiological patterns associated with one or more unwellness conditions and provide this information to the practitioner for analysis. Additionally, data collected may be "crowd sourced" and analyzed to refine small motion recognition patterns for behaviors related to an unwellness condition such as Parkinson's as well as small motion recognition patterns matching particular stages or progressions of a particular unwellness condition. In a particular example, pattern analysis may be used to identify a physiological pattern of small motions indicating an imminent seizure episode in individuals with epilepsy.

In some implementations, as an ongoing support tool for practitioner monitoring of an individual diagnosed with an unwellness condition, the practitioner may review data collected by the wearable data collection device 1104 for periodic evaluations or check-ups, for example to track symptoms, symptom severity, and/or frequency of symptomatic behaviors. Additionally, with the support of data collected by other algorithms 1110, the practitioner may be presented with physiological patterns and/or neurological patterns identified by the learning engines 1118 related to controlled and non-controlled factors trending to correlate with the expression of symptoms or with symptom severity.

In some implementations, the individual 1102 uses the wearable data collection device 1104 in an ongoing manner to aid in managing symptoms and/or evaluating interventions or treatments related to behaviors identified through the algorithms 1110. The individual 1102, in a particular example, may wear the wearable data collection device 1104 as part of a clinical trial related to a particular treatment or intervention for an unwellness condition. In another example, the wearable data collection device 1104 may be configured to provide feedback directly to the individual 1102 to support management of symptoms. In either of the above cases, the learning engines may identify patterns of behaviors correlating to elements within direct control of the individual 1102 which appear to contribute to the frequency or severity of symptoms and recommend non-clinical interventions that the individual 1102 can personally attempt to manage the unwellness condition. The behaviors, in some examples, may include diet, meditation, exercise, sleep patterns, or ingestion of stimulants.

In some implementations, the wearable data collection device 1104 may provide cues for immediate management of symptoms or behaviors corresponding to an unwellness condition. For example, the learning engines 1118 may use the data 1114 related to small (e.g., head) motions and their dynamics to make ongoing assessments or quantifications of the symptoms and behaviors of the individual 1102 and feed back learned data 1124, such as volitional control or biofeedback data, for use in empowering the individual 1102 to conduct "smart management" of symptoms or behaviors, thus gaining better control and autonomy. The feedback, for example, may be presented to the individual 1102 via the wearable data collection device 1104 or another peripheral computing device to provide cues to the individual 1102 for suppressing or extinguishing symptoms or behaviors. In a particular example for an unwellness condition involving vestibular system damage, leading to loss of balance, based upon how level the individual 1102 is maintaining head position, the wearable data collection device 1104 may prompt the individual 1102 (e.g., with a visual target on a heads-up display) to adjust head positioning. Further to this example, the wearable data collection device 1104 may include a balance coaching module for training the individual 1102 to accurately compensate for the effects of the vestibular system damage through correction and feedback. Similar management techniques may be applied an individual 1102 with Huntington's Disease to support the individual 1102 in management of stereotypical Huntington's Chorea movements. In another illustration, the system 1100 may analyze small motion data 1114 to anticipate onset of a seizure in an epileptic individual 1102. In anticipation of seizure activity, the system 1100 may issue a warning to the individual 1102 via the wearable data collection device 1104 or other peripheral computing device.

In some implementations, feedback may incorporate suggestions of coping mechanisms for coping with behavioral episodes stemming from a particular unwellness condition, such as, in some examples, panic disorders and attention deficit hyperactivity disorder (ADHD). The wearable data collection device 1104, in a particular example, may visually present and/or "whisper" an attention focusing mechanism for an individual 1102 coping with ADHD to perform to regain focus. The system 1100, further, may monitor and assess effectiveness of a given coping mechanism for the particular individual 1102, such as a deep breathing exercise for controlling panic.

Rather than or in addition to feeding information back to the individual 1102, in some implementations, the learning engines 118 may generate learned data 1124 for use by one or more systems within or in communication with the wearable data collection device 1104 and/or the individual 1102 to support automated or semi-automated interventions. Such interventions may include, but are not limited to, triggering an implanted device that can disseminate drugs into the body of the individual 1102 appropriately to treat the symptoms or mechanisms of the unwellness condition (e.g., injecting L-Dopa or related pharmaceuticals into the body, etc.) or triggering a neural stimulation device such as a deep brain electrical stimulator or a stimulator using transcranial magnetic or direct-current stimulation.

In a semi-automated intervention, rather than triggering a therapeutic response to identified symptoms, the wearable data collection device 1104 may prompt the individual 1102 for approval of the intervention. For example, a message may appear on a heads-up display of the wearable data collection device 1104, requesting approval to proceed with an identified intervention. In another example, rather than prompting for approval of the individual 1102, the system 1100 may prompt a caregiver or practitioner for authorization to exercise the intervention. Combinations of these features are possible. For example, based upon the perceived immediacy and criticality of the intervention, the system 1100 may exercise an automatic intervention rather than a semi-automatic intervention (e.g., in the circumstance where the system 1100 anticipates that the individual 1102 is not in a condition to provide approval).

In the event of a serious condition needing intervention, in some implementations, the system 1100 may present a medical alert to medical professionals, such as calling for an ambulance or directing a medic at a treatment facility to the current location of the individual 1102. The wearable data collection device 1104, for example, may derive coordinates (e.g., GPS coordinates, an address, etc.) for directing aid to the individual 1102. If the medical professionals addressed are connected to the system 1100 (e.g., via a coordinating software application, etc.), the system 1100 may provide a feed of data and other information for immediate assessment of the condition, such as a portion of the data and analysis information 1114 most recently and/or currently captured. In another example, if the system 1100 has a direct communication link with the medical professionals (e.g., telephone number for text message or short recorded message), the system 1100 may issue a message to the medical professionals with brief assessment data.

In some implementations, the algorithms 1110, individually, in concert, or through data review provided by one or more learning engines 1118, may provide information to a video and/or gaming system to assess the individual's response to a video or game presented to the individual 1102. The video or gaming system may be part of the wearable data collection device 1104 or another computing system in communication with the system 1100. In a particular example, a marketing algorithm may assess the individual's response to the video or game to identify or anticipate the individual's interest in material such as advertisements, political campaign materials, products, product marketing, or other materials involving personal preferences and/or having commercial interests. In another example, a simulation or training system may include one or more algorithms for assessing responses to participants of a simulation (e.g., military training, police officer training, flight training, etc.), such as emotional response.

In some implementations, the video or gaming system may use the assessment of the response of the individual 1102 to the video or game to influence the structure of a game or video that the individual 1102 is presently engaged in. For example, data derived from the algorithms 1110 may be used to alter a difficulty level, direction, or mode of the video game to enhance a desired response from the individual 1102. In a particular example, if the individual 1102 appears bored or disinterested, the difficulty, direction, and/or mode of the game may be altered to encourage great interest from the individual 1102. In another example, the video or gaming system may identify responses of excitement, fear, or other arousal and, in response, provide additional video or game sequences which are similar in nature (e.g., anticipated to elicit the same or similar response from the individual 1102).

In some implementations, the algorithms 1110, individually, in concert, or through data review provided by one or more learning engines 1118, provide feedback 1112 regarding inclination towards an impending adverse health event or atypical behavioral episode. For example, depending upon the severity and/or certainty of the impending adverse health event, the individual 1102, a caregiver, and/or a physician may be alerted to the impending health concern. For example, the wearable data collection device donned by the individual 1102 may present an audible and/or visual warning regarding the likelihood of an impending health event or atypical behavioral episode and, potentially, an indication of the type of event anticipated. Furthermore, the individual 1102 may be prompted with recommendations of measures to take to best prevent, redirect, and/or minimize the atypical behavioral episode (e.g., take an aspirin). The subject, in some implementations, may be presented with feedback 1112 designed to divert a pending health event. For example, feedback 1112 may be presented via the subject's wearable data collection device 1104 (e.g., visual, audible, tactile, etc. feedback) designed to alter one or more physiological conditions indicative of a pending health event, such as subduing a panic attack.

In some implementations, the learning engines 1118 evaluates events identified by the event identifier 1110*a* associated with many individuals as well as corresponding metadata (e.g., demographics, geographic location, time, weather patterns, and other aspects associated with the onset of the event) to identify event patterns similar to a subject group. In some examples, the learning engines 1118 may identify a particular location at a particular time of day associated with multiple events, such as Tuesdays at 12:00 at a particular intersection of a downtown area. Further, the learning engines 1118 may recognize, from archive data 1122, that the events are all associated with a loud noise. For example, a train may pass nearby the intersection on one or more days of the week at particular times, and the whistle of the train may trigger events in one or more individuals susceptible to loud noises. In identifying geographic (and, optionally temporal) "hot spots", the system 1100 may further evolve the capability of issuing warnings to other individuals (or caregivers thereof) within the suspect geographic area at a suspect time.

Further, in some implementations the learning engines 1118 analyze event data corresponding to a collection of individuals to generate a hot spot map. The hot spot map, for example, may be supplied to researchers and clinicians for further review and analysis. In another example, the hot spot map may be supplied to individuals and/or caregivers for informational purposes. As the learning engines 1118 evolve in analysis of event data, the hot spot map may be refined to maps corresponding to individuals having similar demographic, diagnostic, and/or clinical backgrounds. For example, a PTSD hot spot map may differ from a ASD hot spot map.

Although described above as learning algorithms 1118, in other implementations, a portion or all of the learning algorithms 1118 may be replaced with assessment algorithms 1118 lacking an adaptive learning capability. For example, static algorithms for analyzing the data and analysis information 1114 may perform similar roles to learning algorithms 1118 but are not learning algorithms in that they do not change or evolve relative to new data. Instead, static algorithms may be designed to filter or extract information from the data and analysis information 1114, transform, analyze, and/or combine data 1114 with externally obtained data to perform various functions described above while remaining stable over time until they are altered, updated, or replaced. As with the learning engines 1118, one or more static algorithms may be programmed initially into the software, firmware, and/or hardware of a component of the wearable data collection device 1104 or other peripheral computing system. As with the learning engines 1118, static algorithms may also be updated from time to time, for instance in the process of updating software or firmware or hardware as may be accomplished, in some examples, via remote-pushed updates, by user intervention, or by servicing by service technicians.

In some implementations, one or more of the learning algorithms 1118 are replaced or enhanced by concierge intervention via a concierge intervention system (not illustrated) including a data connection to one or more computer systems, such as a network portal connection, to supply data and analysis information 1114 and/or data, analysis, and learning information 1120 to a human operator. In this manner, the concierge intervention system may be used in a manner whereby data related to the individual 1102 may be processed in part by human operators, including, for example, trained health practitioners, data analysts, and/or technicians, rather than being processed solely by automated processes (e.g., algorithms 1110 and/or learning engines 1118). The human operator, for example, may review the data and analysis information 1114 and/or data, analysis, and learning information 1120, performing actions and mental tasks that replace or augment one or more functions or roles performed by learning algorithms 1118. During review of the data and analysis information 1114 and/or data, analysis, and learning information 1120, the actions and mental tasks performed by a human operator may involve or be supplemented by actions or data transformations executing upon a computing device. In one illustrative example, a human operator may review data obtained by the small motion analysis algorithm 1110*m* to manually count heart beats or breaths, potentially with the assistance of some analysis or computation software. The human operator may further enter results of the manual count into the computing device to feed the information back into the system 1100. In another illustrative example, the concierge intervention system can receive the voice recording data 116*a* collected by the wearable data collection device 1104. In such as example, a human operator may listen to the voice recording data 116*a*, count the breaths based on the sound of the person breathing in and out, and then forward the results of this analysis (e.g., manual breath count) to the system 1100 (e.g., the learning engines 1118, wearable data collection device 1104, archive data 1122, etc.). In some implementations, the concierge intervention system may perform the same or similar functions performed by the learning algorithms 1118 and/or algorithms 1110, for instance in cases of quality assurance or oversight or during testing.

In another example, feedback 1112 may be designed to correct for an issue exhibited by the individual 1102. For example, based upon analysis of vestibular dynamics data 1106*f*, feedback 1112 regarding present balance may be presented to the individual 1102. Further, a game or and task such as virtual balance beam may be presented to the individual 1102 to encourage corrective behavior.

In some implementations, a subject identification algorithm 1110*h* may review the data 1108 or analysis information derived by one or more of the other algorithms 1110 to uniquely identify the individual 1102 based upon biometric identification. The biometric identification, in turn, may be used to recognize a current user of the data collection device 1104 in view of a group of potential users (e.g., family members, health club members, etc.). Furthermore, the biometric identification may be used in an authentication process when communicating with third party systems via the data collection device 1104 such as, in some examples, web sites, banks, ATMs, or building security access systems.

The learning engines 1118, in some implementations, review the data 1108 and analysis information 1114 for biometric signatures regarding groups of individuals. For example, biometric similarities may be derived in families, age groups, racial classifications, and/or disease categories. Further, the learning engines 1118 may review the data 1108 and analysis information 1114 to determine an individual biometric signature (e.g., a unique signature based upon particular chronic physiological patterns of the individual). An individual biometric signature, such as an EEG-based biometric signature or a vasculature dynamics signature, may be used to uniquely identify a person. In a particular example, an individual may be recognized via a unique pronounced head pattern. An individual biometric signature may include physiological patterns of heart beats, for instance, or characteristic changes in heart rate or occasional anomalous beats, which may stereotypically occur and thus identify a person at any point; and/or such cardiovascular dynamics may emerge only upon a challenge or change of state, such as when a person stands up or sits down, or after climbing stairs. An individual biometric signature may include physiological patterns of locomotion or driving or other translational motions, for instance periodic oscillations related to arm motion oscillations or oscillations in the vestibular system or oscillations in the eyes or within standard eye movements, any of which can lead to oscillations in the act of driving and in turn can lead to characteristic weaving patterns or oscillations in speed and acceleration. These may be detectable via on-body sensors such as IMUs or via external sensors such a traffic cameras or arrays of cameras or satellite or road pressure sensors or magnetic sensors or other sensors.

In some implementations, an individual biometric signature is used as an individual's running baseline, and the system 1100 may compare against this baseline to detect changes in general state such as sleepiness, drunkenness, drug use, anger, seizure activity, seizure-like brain activity that does not result in frank and clinically noticeable symptoms, distress, cognitive overload, oncoming tantrum or meltdown, oncoming behavioral episodes, oncoming heart attack or stroke, or other such changes from the individual's characteristic baseline. An individual biometric signature may be incorporated with some of the changes from baseline mentioned above, to form a dynamic biometric signature. For instance, the particular manner in which a biometric signal changes during a state change may itself form a signature. For instance, the particular changes to heart and breathing dynamics that happen just before a seizure, or when the person consumes alcohol or coffee or takes a prescription or non-prescription drug, or walks up stairs, for instance, may form or be part of a biometric signature for that person. Therefore, an individual can be monitored, identified, or ruled out as legitimately the target person, by monitoring the particular changes that occur when the person is otherwise known to be tired or drunk or after a seizure or medicine dose.

An individual biometric signature, in some implementations, is derived from multiple types of signals, for instance physiological patterns of heart rate variability in combination with physiological patterns of walking style or gait, even if only one of the types of signal is not enough on its own to uniquely identify an individual. An individual biometric signature also may be used to recognize the probability of a given unknown person being a specific individual, where that probability is neither 0% nor 100%, such as in the case where an exact and certain match cannot be determined. An individual biometric signature may also be used to determine if (or how likely) a given unknown person is a specific individual when only a limited set of possible individuals is considered, not the set of all possible people, such as in the case where a fully unique identification may not be possible but selecting the individual from amongst a smaller set of people (for instance those in a family or a school or a neighborhood) may in fact be possible.

Using the information regarding the individual biometric signature obtained from the learning engines 1118, the system 1100 may supply feedback 1112 related to anomalies, small motion pattern differences, and/or slow-wave changes in the individual 1102. For example, the feedback 1112 may relate to a reduction in sleep, a change in gait that may be indicative of a limp or other injury, a suppression of activity, or other diversion from one or more typical behavioral patterns of the individual. Divergence from typical behavioral patterns, further, may be monitored by the system 1100 to identify physiological patterns leading to expression of a symptom of a disorder, such as seizure activity, meltdown, fainting, heart attack, and/or narcoleptic "sleep attack".

Figure 11B:
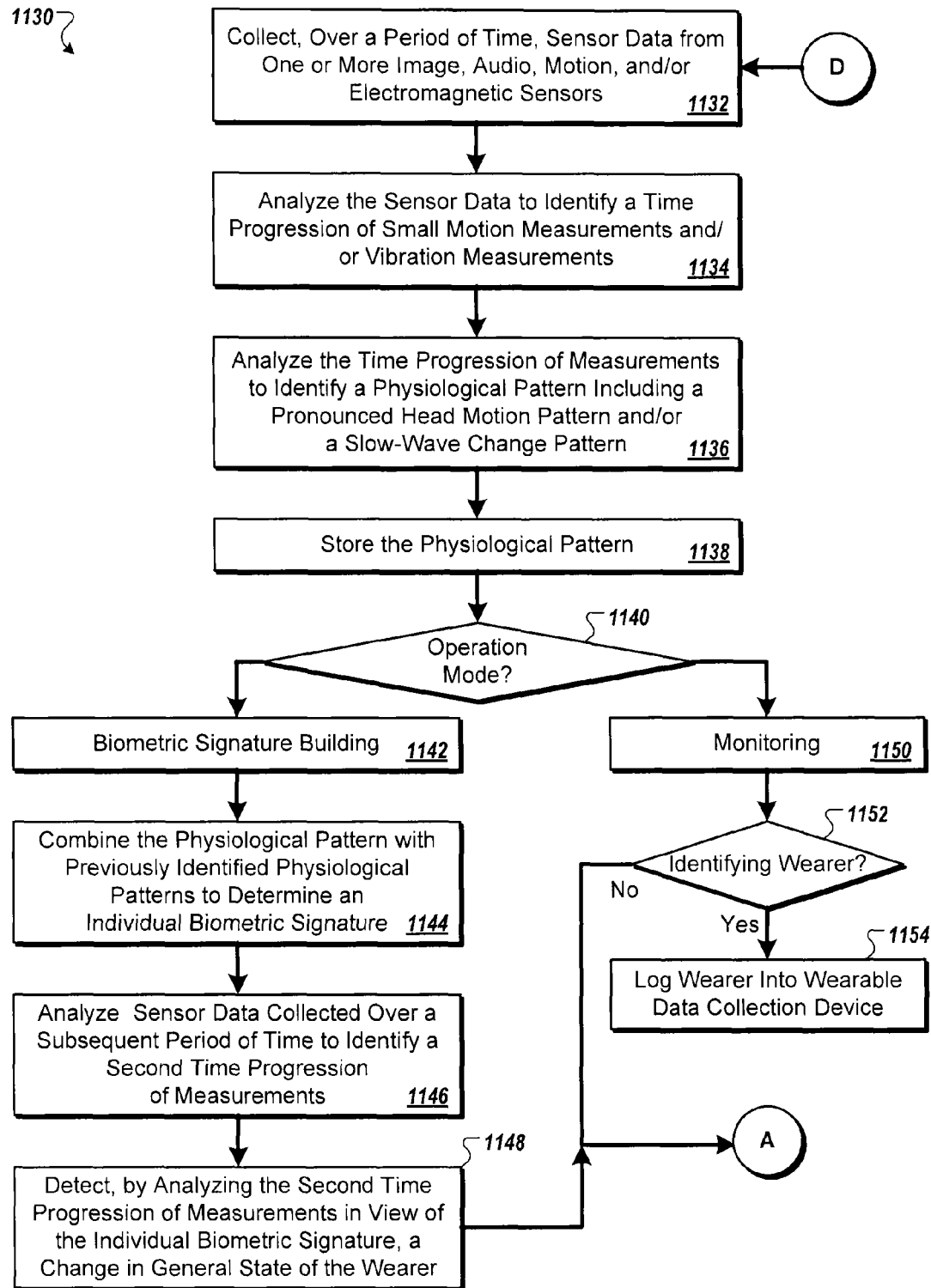
FIGS. 11B and 11C illustrate a flow chart of an example method for identifying and analyzing circumstances surrounding adverse health events and/or atypical behavioral episodes.
Figure 11C:
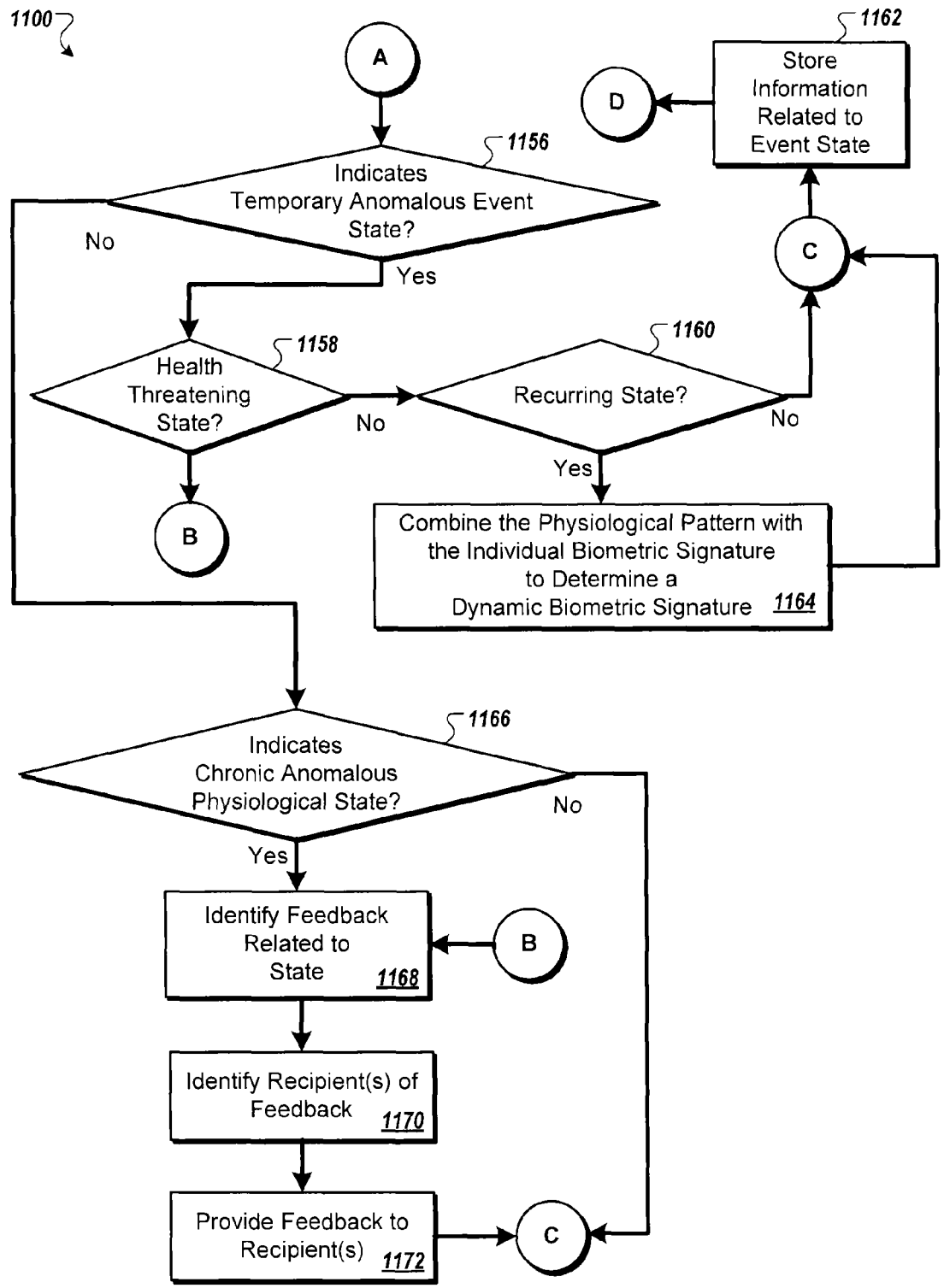

FIGS. 11B and 11C illustrate an example method 1130 for analyzing small motion data and vibration data to determine physiological patterns indicative of events, medical conditions, and physiological states of an individual donning a wearable data collection device. The method 1130, for example, may be implemented by the system 1110, described in relation to FIG. 11A.

Turning to FIG. 11B, in some implementations, the method 1130 begins with collecting, over a period of time, sensor data obtained from one or more image, audio, motion, and/or electromagnetic sensors (1132). For example, a wearable data collection device may include one or more motion sensors and/or electromagnetic sensors capable of discerning small motions of the body. Further to the example, the wearable data collection device may include (additionally or alternatively) one or more microphones capable of discerning small noises of the body, such as bone conduction microphones. In a further example, the wearable data collection device may include one or more imaging sensors for capturing a time series of images or video imagery, as described in relation to FIG. 11A. Additional sensor data may be collected, in some examples, from a laser sensor incorporating interferometry readings to sense small motions, a light sensor collecting light monitoring data to provide interferometry data for small motion analysis, or an electromagnetic sensor to infer motion data based upon disruptions of electromagnetic fields proximate to the sensor. Further, the method 1130 may monitor changes in physiological data via one or more heat measurement devices, such as thermometers, thermistors, or digital heat sensors which may measure heat fluctuations related to small motions of the body. The heat fluctuations, in a particular example, may be related to cardiovascular or other dynamics.

In some implementations, the sensor data is analyzed to identify a time progression of small motion measurements and/or vibration measurements (1134). In some examples, the small motion analysis algorithm 1110*m*, eye motion analysis algorithm 1110*c*, heat fluctuation analysis algorithm 1110*l*, and/or small noise analysis algorithm 1110*p* described in relation to FIG. 11A may analyze the sensor data to quantify and/or infer a time progression of small motion measurements and/or vibration measurements. Further, a time series of image data, such as video data, may be analyzed to derive small motions of the head attributed to movements of a head-mounted image sensor (described in further detail in relation to FIG. 11A). Additionally, the time progression of measurements (1134) may include other motion data, and identifying the physiological pattern (1136) may involve interpreting the physiological-motion data and separating the physiological-motion data from other motions (such as those from walking or gestures) to isolate the small motion data. In some examples, large movements of the users, background noise, outlier data, and other "extraneous" data may be separated to isolate small motion measurements or inferred small motion calculations. In a particular example, background noise may be subtracted from audio data capturing breaths of the individual.

In some implementations, the time progression of measurements is analyzed to identify a physiological pattern including a pronounced head motion pattern and/or slow-wave change pattern (1136). The small motion analysis algorithm 1110*m* described in relation to FIG. 11A, for example, may be designed to analyze sensor data quantifying or inferring small motions of the individual wearing the wearable data collection device to determine a physiological pattern. The physiological pattern may relate to flow dynamics of blood, impulse waves in the vascular system related to heart contractions (healthy or atypical), motions related to muscular contractions in the body functioning as part of bodily systems to control and counteract pulse-related motions (e.g., such as pulses in the neck region, temples, etc.), and/or other related cardiovascular dynamics and/or blood dynamics motions such as cerebral blood flow dynamics. Further, the small motion analysis algorithm 1110*m* may be designed to analyze sensor data quantifying or inferring small motions of the individual wearing the wearable data collection device to determine breathing dynamics.

In some implementations, the physiological pattern is stored upon a computer readable storage device (1138). The physiological pattern, for example, may be stored to a computer-readable medium connected to or in communication with the wearable data collection device. Further, the physiological pattern may be uploaded to a network-accessible storage region. In one example, the data may be stored as archive data 1122 as described in FIG. 11A. In uploading the physiological pattern to the network-accessible storage region, the physiological pattern may contribute to learning engines, such as the learning engines 1116, to analyze physiological patterns corresponding to individuals sharing particular factors, such as demographic factors, medical diagnosis factors, and/or clinical background factors (e.g., sensitivity profiles such as audio, visual, and/or haptic sensitivities, aversions, responsiveness to pharmaceuticals, behavioral therapies, digestive problems, etc.).

In some implementations, the method 1130 determines an operational mode (1140). The operational modes include a biometric signature building mode (1142), pertaining to recognizing and establishing one or more physiological patterns of the individual and determining an individual biometric signature. While in the biometric signature building mode (1142), in some implementations, the physiological pattern is combined with previously identified physiological patterns to determine an individual biometric signature (1144). For example, the learning engines 1118 (described in relation to FIG. 11A) may determine the individual biometric signature based upon multiple chronic physiological patterns of the individual. In a particular example, an individual biometric signature may include both a cardiovascular dynamics signature as well as a breathing dynamics signature. Additional patterns contributing to the individual biometric signature, in some examples, can include eye movement dynamics, neural dynamics, vascular dynamics, blood flow dynamics, skin dynamics, and vestibular dynamics. Further, activity-based physiological patterns may contribute to an individual biometric signature or dynamic biometric signature (described below). The activity-based physiological patterns may include, in some examples, locomotion (e.g., gait) dynamics, driving-related physiological dynamics, and/or behavioral patterns (e.g., emotional patterns, mood patterns, rocking, self-hugging, self-injurious behaviors, etc.).

In some implementations, sensor data collected over a subsequent period of time is analyzed to identify a second time progression of measurements (1146). The second time progression of measurements may include similar and/or dissimilar data to the initial time progression of measurements. The collection and analysis, for example, may be conducted similar to the collection and analysis described in steps 1132 through 1136 of the method 1130 by the same sensor elements and/or different sensor elements.

In some implementations, a change in general state of the wearer is detected by analyzing the second time progression of measurements in view of the individual biometric signature (1148). The change in general state, for example, may include a noticeable (e.g., statistically relevant) difference between the individual biometric signature and at least one component of the biometric signature. In other words, the change may be related to one or more physiological patterns contributing to the individual biometric signature. A change in general state, in some examples, can include a state of fatigue, intoxication, narcotic ingestion, anger, seizure activity, seizure-like brain activity that does not result in frank and clinically noticeable symptoms, distress, cognitive overload, oncoming tantrum or meltdown, oncoming behavioral episodes, oncoming heart attack or stroke, or other such changes from the individual's characteristic baseline. Further, the change in general state may include a periodic normal event, such as ovulation, pregnancy, or sexual arousal.

Returning to operational mode (1140), a second operational mode of the method 1130 includes monitoring (1150). While in the monitoring operational mode (1150), in some implementations, the identity of the wearer may be ascertained by identifying a match between the physiological pattern and a known physiological pattern of the individual, such as the individual's biometric signature. (1152). If the identity of the wearer is ascertained through comparison between the physiological pattern and the known individual biometric signature (or physiological pattern portion thereof) (1152), the wearer may be logged into the wearable data collection device (1154). In one example, the biometric signature of the wearer may be used as a security code to authorize the wearer to interact with the wearable data collection device. In a second example, one or more features of the wearable data collection device may be automatically set (personalized) based upon identifying the present wearer as a known wearer of the wearable data collection device.

Turning to FIG. 11C, whether in biometric signature building mode (1142) or monitoring mode (1150), in some implementations, if the physiological pattern (or change in general state) indicates a temporary anomalous event (1156), the method 1130 determines whether the temporary anomalous event state qualifies as a health threatening state (1158). In some examples, a health threatening state may include stroke, cardiac arrest, epileptic seizure, narcoleptic "sleep attack", Autistic tantrum, migraine, or a pattern indicating the onset thereof. Upon identification of a health threatening state (1158), in some implementations, feedback is identified related to the health threatening state (1168), recipients of such feedback are identified (1170), and the feedback is provided to the identified recipients (1172). For example, the wearer may be alerted via audible and/or visual feedback regarding an impending health threatening state. A variety of feedback is described in relation to feedback 1112 of FIG. 11A. During or prior to a health threatening state, feedback provided to the wearer may include, in additional examples, triggering magnetic, energy, electrical, and/or pharmaceutical doses to curb or suppress symptoms (or the onset thereof). Further, communications may be issued to third party computing devices to alert one or more third parties regarding the health threatening state. The third parties, in some examples, may include a guardian, caretaker, medical practitioner, or emergency response team. The information, in some examples, may be issued via a software application integrated with a physiological data monitoring system implemented upon the wearable data collection device. In other examples, the alert may include a text message, email message, SMS message, or other electronic messaging system capable of relaying, in real time, information regarding the individual's health threatening state. The method 700 of FIGS. 7A through 7C, in a particular example, illustrates example feedback processes for mitigating atypical behaviors. As described by the method 700, for example, pharmaceutical doses and/or other doses may be triggered upon authorization of a medical professional or caregiver. Additionally, the physiological pattern and/or underlying sensor data may be supplied to the third party computing system for further evaluation and diagnosis.

If the physiological pattern (or change in general state) indicates a recurring state (1160), in some implementations, the physiological pattern is combined with the individual biometric signature to determine a dynamic biometric signature (1164). The dynamic biometric signature, as described in relation to FIG. 11A, incorporates both chronic physiological patterns as well as physiological patterns indicative of recurring transitory physiological states. The recurring transitory physiological states, in some examples, can include conditions such as intoxication, fatigue, narcotic ingestion, jet-lag, distress, aggression, attention deficit, anger, or violence, as well as temporary or periodic normal events, such as ovulation, pregnancy, and sexual arousal. In combining the recurring state-related physiological pattern with the individual biometric signature, for example, the dynamic biometric signature of the individual may better identify the ebbs and flows of physiological patterns of the individual. These movements from a "baseline", in some examples, may occur based upon a variety of influence factors including, in some examples, circadian rhythms, seasonal rhythms, activity patterns of the wearer (e.g., sleep patterns, exercise patterns, etc.), pharmaceutical intake, stimulant intake, and/or dietary intake. The dynamic biometric signature, in some implementations, incorporates influence factors related to one or more physiological patterns demonstrating a change from the baseline individual biometric signature.

In some implementations, information related to the state and/or the dynamic biometric signature is stored upon a storage medium connected to or in communication with the wearable data collection device (1162). The information related to the state and/or the dynamic biometric signature, for example, may be stored to a computer-readable medium connected to or in communication with the wearable data collection device. Further, the information related to the state and/or the dynamic biometric signature may be uploaded to a network-accessible storage region. In one example, the data may be stored as archive data 1122 as described in FIG. 11A. In uploading the information related to the state and/or the dynamic biometric signature to the network-accessible storage region, the information related to the state and/or the dynamic biometric signature may contribute to learning engines, such as the learning engines 1116 of FIG. 11A, to analyze physiological patterns, individual biometric signatures, and/or dynamic biometric signatures corresponding to individuals sharing particular factors, such as demographic factors, medical diagnosis factors, and/or clinical background factors (e.g., sensitivity profiles such as audio, visual, and/or haptic sensitivities, aversions, responsiveness to pharmaceuticals, behavioral therapies, digestive problems, etc.).

In some implementations, the change in general state and/or the physiological pattern indicates a chronic anomalous physiological state (1166). A chronic anomalous physiological state, for example, can include balance problems, Autistic behaviors, slow-wave changes indicative of unwellness conditions, and small head motion patterns indicative of unwellness conditions.

Upon identification of a chronic anomalous physiological state (1158), in some implementations, feedback is identified related to the chronic anomalous physiological state (1168), recipients of such feedback are identified (1170), and the feedback is provided to the identified recipients (1172). A variety of feedback is described in relation to feedback 156 of FIG. 1B and feedback 1112 of FIG. 11A. For example, diagnostic information related to the chronic anomalous physiological state may be shared with a caregiver or medical practitioner via a communication to a third party computing device. The communication, for example, may be issued via a software application integrated with the monitoring system implemented upon the wearable data collection device. In other examples, the communication may include a text message, email message, SMS message, or other electronic messaging system capable of relaying, in real time, information regarding the individual's chronic anomalous physiological state. If the chronic anomalous physiological state represents a particular stage or progression of an unwellness condition, in one example, the wearer and/or a third party may be supplied a report regarding progress between stages or progressions of the unwellness condition. Additionally, the physiological pattern and/or underlying sensor data may be supplied to the third party computing system for further evaluation and diagnosis.

If, instead, the physiological pattern fails to match a particular temporary anomalous event state or chronic anomalous physiological state (1166), the information related to the physiological pattern is stored to a computer readable storage medium (1162), as described above. For example, the unidentified patterns may be logged and supplied to learning engines to compare with physiological patterns of other individuals in an effort to link such physiological patterns to particular temporary anomalous event states and/or chronic anomalous physiological states.

Although described as a particular series of operations, in other implementations, one or more steps of the method 1130 may be executed in a different order. For example, information regarding a chronic anomalous physiological state may be stored to a computer readable storage medium (1162) and later combined with other information regarding the chronic anomalous physiological state and/or additional identified physiological states of the individual within a more complete report-based feedback (1168, 1172). In another example, physiological patterns and additional data identifying a recurring state may be used to identify triggers of a health threatening state. In a particular example, a physiological pattern associated with onset of symptoms of migraine may be found to coincide with or follow a physiological pattern associated with fatigue. Feedback (1168), in this circumstance, may suggest to the individual a correlation between fatigue and the onset of migraines.

In further implementations, one or more steps of the method 1130 may be excluded and/or one or more additional steps may be added to the method 1130. For example, some implementations may not include determination of a dynamic biometric signature (1164). In another example, the method 1130 may include, prior to collecting sensor data (1132), calibrating interpretation of initial sensor data of the wearable data collection device to identify small motions. Further modifications of the method 1130 are possible without exceeding the scope and spirit of the method 1130.

Figure 14:
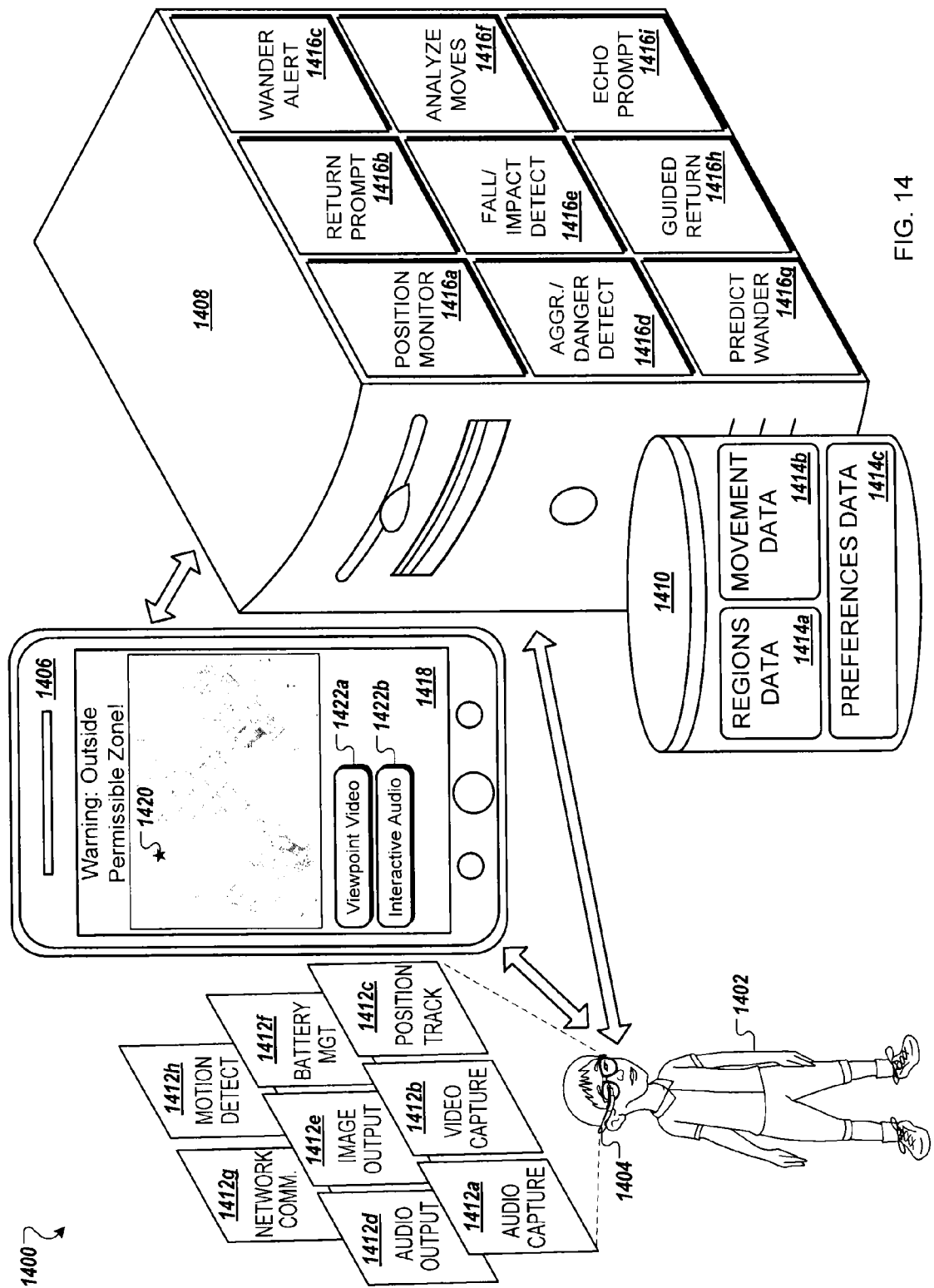
FIG. 14 is a block diagram of an example system for tracking location of an individual via a portable computing device.

FIG. 14 is a block diagram of an example system 1400 for tracking location of an individual 1402 carrying or wearing a portable computing device, such as a wearable data collection device 1404, capable of collecting position tracking data via one or more position tracking elements 1412c. The system 1400 may be used to detect wandering of the individual 1402 (e.g., a child, an adult suffering dementia, or a pet, etc.) outside of an established permissible zone through analysis of position tracking data. The system 1400 further includes a processing system 1408 with one or more algorithms 1416 for monitoring and prompting return of the individual 1402 upon wandering outside of the permissible zone. The processing system 1408, although illustrated as a stand-alone processing server, may be included within the wearable data collection device 1404, a computing device in communication with the wearable data collection device 1404, and/or a network-accessible processing system (e.g., cloud-based server system) in wireless communication with the wearable data collection device 1404. Each of the algorithms 1416, further, may be implemented wholly or in part upon the wearable data collection device 1404 and/or an external (local or remote) computing system. Fewer or more features may be included within the system 1400, for example based upon a type of portable computing device. Although described in relation to the wearable data collection device 1404, in other embodiments, features or portions of features of the system 1400 may be implemented to use data and output features of a different style of computing device carried or worn by the individual 1402 such as, in some examples, a handheld electronic device such as a smart phone, tablet computer, or digital entertainment device, or a wearable device such as a smart watch or a specialized health and fitness computing device.

In some implementations, a positioning monitoring algorithm 1416a monitors the position of the wearable data collection device 1404 through analysis of the position tracking data. The position tracking elements 1412c, in some examples, may include Global Positioning System (GPS), Wi-Fi-based positioning system (WPS), indoor positioning system (IPS), mobile phone tracking, local positioning system (LPS), and/or other positioning systems using wireless signals to determine a relative or specific position of the wearable data collection device 1404. In one example, the system 1400 may be used to determine a specific position of the individual 1402. In another example, the system 1400 may be used to determine the position of the wearable data collection device 1404 relative to a separate portable computing device 1406 carried or worn by a caregiver of the individual 1402.

Position of the wearable data collection device 1404, in some implementations, is analyzed relative to regions data 1414a established by a caregiver and stored within a data store 1410. The caregiver may set, within the regions data 1414a, a radius, perimeter, or other regions and/or zones for permissible movement of the individual 1402. The regions data 1414a may include two or more permissible zones based upon a current location of the individual 1402. For example, the individual 1402 may be limited to a first permissible zone while at home (e.g., the house and a surrounding section of yard) and a second permissible zone while at school (e.g., a perimeter of the school property including the building and the playground area). Furthermore, the individual 1402 may be limited to a radius distance from the portable computing device 1406 while in a further location, such as the grocery store or park.

In some implementations, the regions data 1414a may include an exclusion zone within an otherwise permissible zone, such as a swimming pool within the back yard of a property or a road abutting the park but potentially within the permissible radius of the portable computing device 1406. The caregiver, for example, may identify an exclusion zone through selecting a region, item, or position within a map display. In another example, the caregiver may identify types of exclusion zones such as, in some examples, pools, fountains, ponds, and other bodies of water, highways and other busy roadways, and/or steep drop-offs. The types of exclusion zones, for example, may be stored within preferences data 1414*c*. The processing system 1408 may identify characteristics, within images or video captured by one or more video capture elements 1412*b* of the wearable data collection device 1404, as being indicative of one of the types of exclusion zones and automatically add the recognized region as a local exclusion zone.

In some implementations, one or more exclusion zones may be dynamically identified by the system 1400. For example, construction zones, down power lines, or other temporary hazards may be identified through crowd-sourcing and/or analysis of data captured by the image capture elements 1412*b*. In another example, immediate hazards, such as a hostile dog chained within a front yard, may be identified through analysis of image capture data (e.g., by a danger detection algorithm 1416*d*) and automatically added as an exclusion zone. In addition to safety hazards, in some examples, exclusion zones may include circumstances that are identified as inappropriate to the individual 1402 (e.g., potentially distracting, frightening, or enticing). The circumstances may be temporal, such as a day of the week and/or time of day when garbage collectors visit the neighborhood of the individual 1402. In some embodiments, the inappropriate circumstances are automatically detected by the processing system 1408 through analysis of reactions of the individual 1402 to the various circumstances. For example, as described in relation to predicting susceptibility of the individual to atypical behavioral episodes via the method 700 of FIGS. 7A-7C. The processing system 1408, for example, may coordinate with the system 1100 of FIG. 11A to identify circumstances triggering atypical behavioral episodes and/or wandering.

In some implementations, the position monitoring algorithm 1416*a* collects movement data 1414*b* of the individual 1402 while moving within the permissible zone via the position tracking elements 1412*c*. The movement data 1414*b*, in some examples, may include a collection of positions correlated to periodic time stamps. Through later analysis of the movement data 1414*b*, for example, a movement analysis algorithm 1416*f* of the analysis system 1408 may identify patterns of behavior associated with the individual 1402. In one example, the patterns of behavior may be analyzed to identify where to position items for the individual 1402 to notice (e.g., learning tools, etc.). In another example, the patterns of behavior may be analyzed to identify comfort zones of the individual 1402 (e.g., where the individual 1402 goes when tired, frightened, anxious, etc.), entertainment zones of the individual 1402 (e.g., where the individual 1402 moves actively or plays) and/or avoidance zones of the individual 1402 (e.g., areas within the permissible zone that the individual 1402 rarely if ever visits).

A wander prediction algorithm 1416*g*, in some implementations, uses the patterns of behavior derived from analysis of the movement data 1414*b* to predict, based upon recent and/or present behavior, a likelihood of the individual 1402 to wander outside of the permissible zone. In some examples, brisk pacing, visiting a particular series of locations (e.g., the bathroom followed by the refrigerator followed by the back door), or remaining stationary in a particular location for at least a particular period of time (e.g., looking out of the dining room window) may be identified as being indicative of leading to wandering of the individual 1402 outside of the permissible zone. The movement data, in addition to position tracking data, may include data derived via motion detection elements 1412*h*, such as one or more gyroscopes, accelerometers etc., to identify bodily motions (e.g., shaking, bouncing, stimming, etc.) of the individual 1402. The bodily motion data, in addition to or instead of the position data, may be used by the wander prediction algorithm 1416*g* in predicting a likelihood of the individual 1402 to wander outside of the permissible zone.

In some implementations, the wander prediction algorithm 1416*g* determines, based upon additional data collected by the wearable data collection device 1404, such as one or more of the algorithms 1110 described in relation to FIG. 11A, physiological factors that appear to lead to wandering. For example, the vocalization analysis algorithm 1110*o* may be used to identify vocalizations which commonly precede wandering outside of the permissible zone. In another example, the wander prediction algorithm 1416*g* may analyze EMG data 116*i* and/or EEG data to identify neurological data patterns commonly preceding wandering of the individual 1402 outside of the permissible zone.

Upon the position monitoring algorithm 1416*a* identifying wandering of the individual 1402 outside of the permissible zone, in some implementations, a return prompting algorithm 1416*b* prompts the individual 1402 to cease wandering outside of the permissible zone. For example, the return prompting algorithm 1416*b* may issue pre-recorded verbal prompts through one or more audio output elements 1412*d* included in or in communication with the wearable data collection device 1404 to entice the individual 1402 to cease wandering outside of the permissible zone. The pre-recorded verbal prompts may be provided by a caregiver (e.g., parent, teacher, spouse, child, etc.) of the individual 1402. The pre-recorded verbal prompts, in some examples, may include "I miss you", "where did you go?", "come back", "go home", or "come home for some cookies." If, instead, the individual 1402 is moving towards an exclusion zone, the return prompting algorithm 1416*b* may prompt the individual 1402 to avoid the exclusion zone. In some examples, the return prompting algorithm 1416*b* may present a pre-recorded verbal prompt warning the individual 1402 to "stay away from the pool", "be careful around the street", or "watch out for cars". In another example, the return prompting algorithm 1416*b* may present images to the individual 1402 via one or more image output elements 1412*e* of the wearable data collection device 1404 (e.g., upon a heads-up display region of the wearable data collection device 1404) to entice the individual 1402 to cease wandering outside of the permissible zone. For example, the return prompting algorithm 1416*b* may present the individual 1402 with images of loved ones, favorite items, favorite foods, and/or images of the permissible home (e.g., the wearer's bedroom, the wearer's classroom, etc.).

A guided return algorithm 1416*h*, in some implementations, provides the individual 1402 with instructions on moving to a desired location, such as returning to the permissible zone or moving to a present position of the caregiver. The guided return algorithm 1416*h*, for example, may provide the individual 1402 with step-by-step audio and/or visual indications of directions to take in moving towards the desired location. The instructions, in some examples, may include arrow indicators or an illuminated path overlaid upon a heads-up display of the wearable data collection device 1404. In another example, the guided return algorithm 1416*h* may provide the individual 1402 with a visual image of the present position of the caregiver. For example, the caregiver may be located near a building, flag pole, large tree, fountain, or other easily visible landmark which may aide in orienting the individual 1402.

In some implementations, the guided return algorithm 1416*h* entices the individual 1402 to move to the desired location by illustrating, within a heads-up display of the wearable data collection device 1404, an interesting object along the path of movement. For example, an avatar of one of the wearer's favorite objects, animals, or popular media characters may be illustrated as moving along the path in the direction of the desired location such that the individual 1402 is encouraged to follow the avatar. A caregiver, for example, may select a particular avatar as part of the preferences data 1414c. Audio prompts, for example provided by the return prompt algorithm 1416b, may encourage the individual 1402 to follow the avatar. For example, the avatar may speak "follow me!" or a pre-recorded trusted voice (e.g., the voice of the caregiver, family member, or t popular cartoon character) may instruct the individual 1402 to follow the avatar. If the individual 1402 fails to follow the path of the avatar, the avatar may disappear off of the visual region of the heads up display. In this manner, the individual 1402 may be encouraged to move in the direction where the avatar was last seen, for example in a manner of hide and seek. The avatar may further pop onto the edge of the screen, gesture in a desired direction, and move off of the edge of the visible display within that direction to encourage the individual 1402 to follow. An example of augmented video in a panoramic moving display. Further, if the individual 1402 fails to follow the avatar, the guided return algorithm 1416h may alter the style of avatar draw attention of the individual 1402 to the avatar. Selection of a particularly effective augmentation style is described in greater detail, for example, in relation to the method 800 of FIG. 8.

In some implementations, upon the individual 1402 moving outside of the permissible zone, a wander alert algorithm 1416c issues one or more alerts, via one or more network communication interface elements 1412g of the wearable data collection device 1404, for third party attention regarding the movement of the individual 1402. For example, the wander alert algorithm 1416c may issue one or more audio or text alerts to a caregiver's portable computing device 1406 (e.g., smart phone, wearable data collection device, etc.) via a software application 1418 integrated with the wander alert algorithm 1416c. Further, the wander alert algorithm 1416c may launch the integrated software application 1418 to allow the caregiver to review data collected by the wearable data collection device 1404. For example, the integrated software application 1418 may include a map interface graphically displaying a present position 1420 of the wearable data collection device 1404. In another example, the wander alert algorithm 1416c may issue text messages or short message recordings to one or more telephone numbers.

The wander alert algorithm 1416c, in some implementations, varies alerts based upon current circumstances. For example, the wander alert algorithm 1416c, via the integrated software application, may determine that a first caregiver (e.g., particular parent, teacher, babysitter, etc.) is presently positioned nearest to the individual 1402 and initially issue the alert to the nearest caregiver. In another example, the wander alert algorithm 1416c may issue an alert to each caregiver within a particular range of the wearable data collection device 1404 (e.g., a quarter mile, etc.). The integrated software application, for example, may provide a user interface for the caregiver to customize a distance range for receipt of alerts, styles of alerts (e.g., text message vs. audible ping, etc.), or a priority listing of alert mechanisms (e.g., parents via software application, teacher via text message, babysitter via email message, etc.).

In some implementations, the wander alert algorithm 1416c enables data sharing between the wearable data collection device and a web portal, such as a web page. The software application 1418, for example, may be executed within the web portal. Via the web portal, one or more third parties may review real time data collected by the wearable data collection device 1402. Further, the web portal may enable a third party to interact with the individual via the audio output elements 1412d and/or image output elements 1412e.

In some implementations, the caregiver may select, within the software application 1418, to review viewpoint image data captured by the wearable data collection device 1404. For example, upon selection of a viewpoint video control 1422a, the caregiver may be presented with a series of images or live video of a present direction of gaze of the individual 1402 as captured by the video capture elements 1412b. In this manner, the caregiver may determine a present location of the individual 1402 and move towards locating the individual 1402.

In some implementations, in addition to video obtained in a direction of a gaze of the individual 1402, the caregiver may be presented with image data of a facial region of the individual 1402. For example, a face-directed video capture element of the wearable data collection device 1404 may capture facial expressions of the individual 1402. In this manner, the caregiver may assess emotional cues in the expression of the individual 1402.

In some implementations, the caregiver may choose, within the software application 1418, to engage in an interactive audio session with the individual 1402. For example, upon selection of an interactive audio control 1422b, the software application 1418 may establish a two-way audio communication channel with the wearable data collection device 1404 via the network communication elements 1412g for engaging in a discussion with the individual 1402. In this manner, the caregiver provide instructions to the individual 1402 (e.g., "stay where you are", "look for the yellow tent", or "ask the nearest adult for help") via the audio output elements 1412d of the wearable data collection device 1404, and the caregiver may listen to the individual 1402 via one or more audio capture elements 1412a of the wearable data collection device 1404.

In some implementations, rather than receiving live audio instructions from a caregiver, an echo prompting algorithm 1416i may automatically prompt the individual 1402 to repeat messages for the benefit of a third party. For example, the echo prompting algorithm 1416i may prompt the individual 1402 to announce "I'm lost and I need help". Prior to prompting the individual, the processing system 1408 may identify a third party (e.g., police officer, other adult, etc.) within communication range of the individual 1404. For example, the processing system 1408 may analyze image data captured by the video capture elements 1412b of the wearable data collection device 1404 to identify one or more persons near the individual 1402. Upon identifying an attentive third party, for example, the echo prompting algorithm 1416i may prompt further phrases, such as "I need to go to 1 Bluebird Lane," "my name is Harry," or "can you help me find my mom?". In addition to or instead of audio prompts, in another example, the echo prompting algorithm 1416i may present image prompts to the individual 1402, similar to the teleprompter algorithm 544 described in relation to FIG. 5B.

Upon engaging the aid of a third party, the echo prompting algorithm 1416i, in some implementations, parses audio, captured by the audio capture elements 1412a of the wearable data collection device 1404, to identify statements of the individual and/or the third party. For example, the echo prompting algorithm **1416*i* may parse a question asked of the individual 1402 by the third party. In another example, the echo prompting algorithm 1416*i* may confirm repetition by the individual of the prompted message. In this manner, the echo prompting algorithm 1416*i* may prompt conversation between the individual 1402 and the third party to help the third party to return the individual 1402 to the caregiver or to a desired location. Conversation prompts are described in greater detail, for example, in relation to the social interaction algorithms 910 of FIG. 9**.

In some implementations, an aggressive behavior and other danger detection algorithm **1416*d* assesses potentially dangerous situations to the individual 1402. Whether or not the individual 1402 is wandering outside of the permissible zone, the aggressive behavior and other danger detection algorithm 1416*d* may analyze data obtained by the wearable data collection device 1404 to identify any potential dangers to the individual 1402. For example, by analyzing image data captured by the video capture elements 1412*b* of the wearable data collection device 1404, the aggressive behavior and other danger detection algorithm 1416*d* may detect aggressive behaviors of third parties within the vicinity of the individual 1402, such as postures indicative of bullying, an aggressive stance of a neighborhood dog, or a third party (person, animal, small vehicle, etc.) moving swiftly towards the individual 1402 on a vector of potential impact. The aggressive behavior and other danger detection algorithm 1416*d* may coordinate, in a particular example, with the body language identifier 910*a* of FIG. 9 to analyze body language of third parties within the vicinity of the individual 1402. In another example, the aggressive behavior and other danger detection algorithm 1416*d* may analyze voice patterns of third parties within the vicinity of the individual 1402, as captured by the audio capture elements 1412*a* of the wearable data collection device 1404, to identify bullying or aggressive vocalizations. Analysis of audio data for identification of emotional cues is discussed further in relation to the method 1000 of FIG. 10A**.

In some implementations, in response to identification of aggressive behavior or other dangers by the aggressive behavior and other danger detection algorithm **1416*d*, the processing system 1408 may prompt the individual 1402 to take protective measures, such as moving out of the way of potential impact, avoiding the aggressive animal, or leaving the vicinity of the bullying third party. For example, audio prompts may be presented via the audio capture elements 1412*a* of the wearable data collection device 1404 and/or visual prompts may be presented via the image output elements 1412*e* of the wearable data collection device in a similar manner as described in relation to the return prompting algorithm 1416*b***.

An impact and fall detection algorithm **1416*e*, in some implementations, analyzes data collected by the wearable data collection device 1402 to identify events which may cause physical injury to the individual 1402. In one example, the impact and fall detection algorithm 1416*e* analyzes bodily motion data captured by the motion detecting elements 1412*h* to identify jarring, swift, or other unusual motions of regions of the body carrying a motion detecting element 1412*h*. For example, swift or jerking motion of the head of the individual 1402 may be associated with stumbling, tripping, or falling. In another example, the impact and fall detection algorithm 1416*e* may analyze image data captured by the video capture elements 1412*b*, in addition to or instead of the bodily motion data, to identify impacts and/or falls. For example, based upon video data, the impact and fall detection algorithm 1416*e* may identify that the individual 1402** was punched by a bully, was hit by a bicyclist, or fell off of a picnic table.

Further, in some implementations, the impact and fall detection algorithm **1416*e* may, upon detection of potential injury or pending injury to the individual, issue an alert to one or more third parties. Alerts regarding injury or potential injury, for example, may be issued in a manner similar to that described in relation to the wander alert algorithm 1416*c*. Further, one or more images, video snippets, and/or audio snippets of the event which led to potential injury of the individual 1404 may be captured by the processing system 1408 and stored within the data store 1410. In another example, the images, video snippets, and/or audio snippets may be supplied to the third party (e.g., to the portable computing device 1406**) for review.

In some implementations, upon detecting potential injury to the individual 1402, the processing system 1408 may further analyze physiological effects of the fall or impact on the individual 1402, for example using one or more of the algorithms 1110 described in relation to FIG. 11A. In a particular example, vocalization analysis **1110*o* may identify indications of pain, fear, or trauma, while bodily motion analysis of motion data captured by the motion detection elements 1412*h* may identify whether the individual 1402** appears dizzy, limping, wincing, or otherwise compensating for injury and/or pain.

Although various functionality of the processing system 1408 is described in relation to identifying that the individual 1402 has moved outside of a permissible zone, in some implementations, the individual 1402 and/or a caregiver has the ability to manually activate a "rescue mode" which triggers, for example, the return prompting algorithm **1416*b* and/or the guided return algorithm 1416*h*. For example, the individual 1402, while visiting a museum with a caregiver, may become disoriented and fail to locate the caregiver even though the individual 1402 is within a permissible radius of the portable computing device 1406. The individual 1402 may manually activate the "rescue mode" for help in identifying a current position of the caregiver. Conversely, if the individual 1402 is hiding from the caregiver within the permissible zone, or the caregiver otherwise is unable to locate the individual 1402, the caregiver may activate a "manual return" mode, for example within the software application 1418, to identify a present location of the individual 1402 and/or to prompt the individual 1402** to call to the caregiver and/or return to the caregiver.

In some implementations, the functionality of the individual algorithms 1416 depends in part upon power consumption of the wearable data collection device 1404. For example, based upon indications supplied by one or more battery management elements **1412*f* of the wearable data collection device 1404, the processing system 1408 may determine that not enough power is available to perform all of the functionality of the algorithms 1416. The processing system 1408, in response, may prioritize particular functionality of the system 1400 while suppressing other (e.g., non-essential) functionality to conserve power to the wearable data collection device 1404. Prioritization may be based, in part, upon preferences data 1414*c* supplied by a caregiver. In a particular example, after identifying that the individual 1402 is wandering outside of the permissible zone, if the battery management elements 1412*f* indicate that the wearable data collection device 1404 has a low power level, the processing system 1408 may determine that the viewpoint video feature of the software application 1418** executing upon the caregiver's portable computing device 1406 may be reduced or suppressed to preserve power for the position monitoring algorithm 1416a.

In some implementations, upon identifying that a power level of the wearable data collection device 1404 has fallen below a threshold level, the processing system 1408 may issue a warning to one or more interested parties. For example, the processing system 1408 may issue an alert in the manner supplied by the wander alert algorithm 1416c, to warn third parties that the wearable data collection device 1404 is low on power. In this manner, a caregiver may, for example, recharge the wearable data collection device or swap in a new battery pack.

Figure 15A:
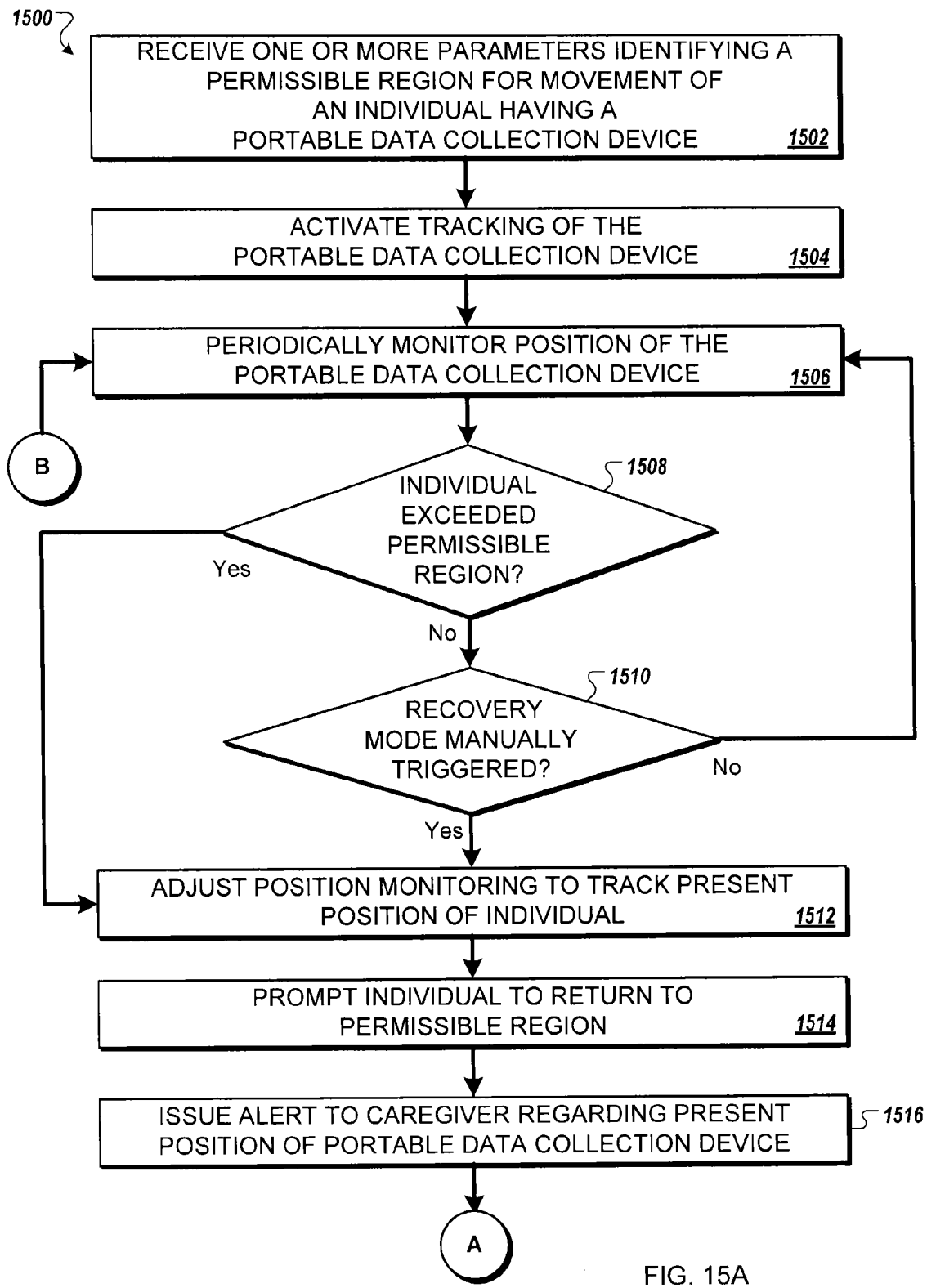
FIGS. 15A and 15B illustrate a flow chart of an example method for tracking location of an individual via a portable computing device.
Figure 15B:
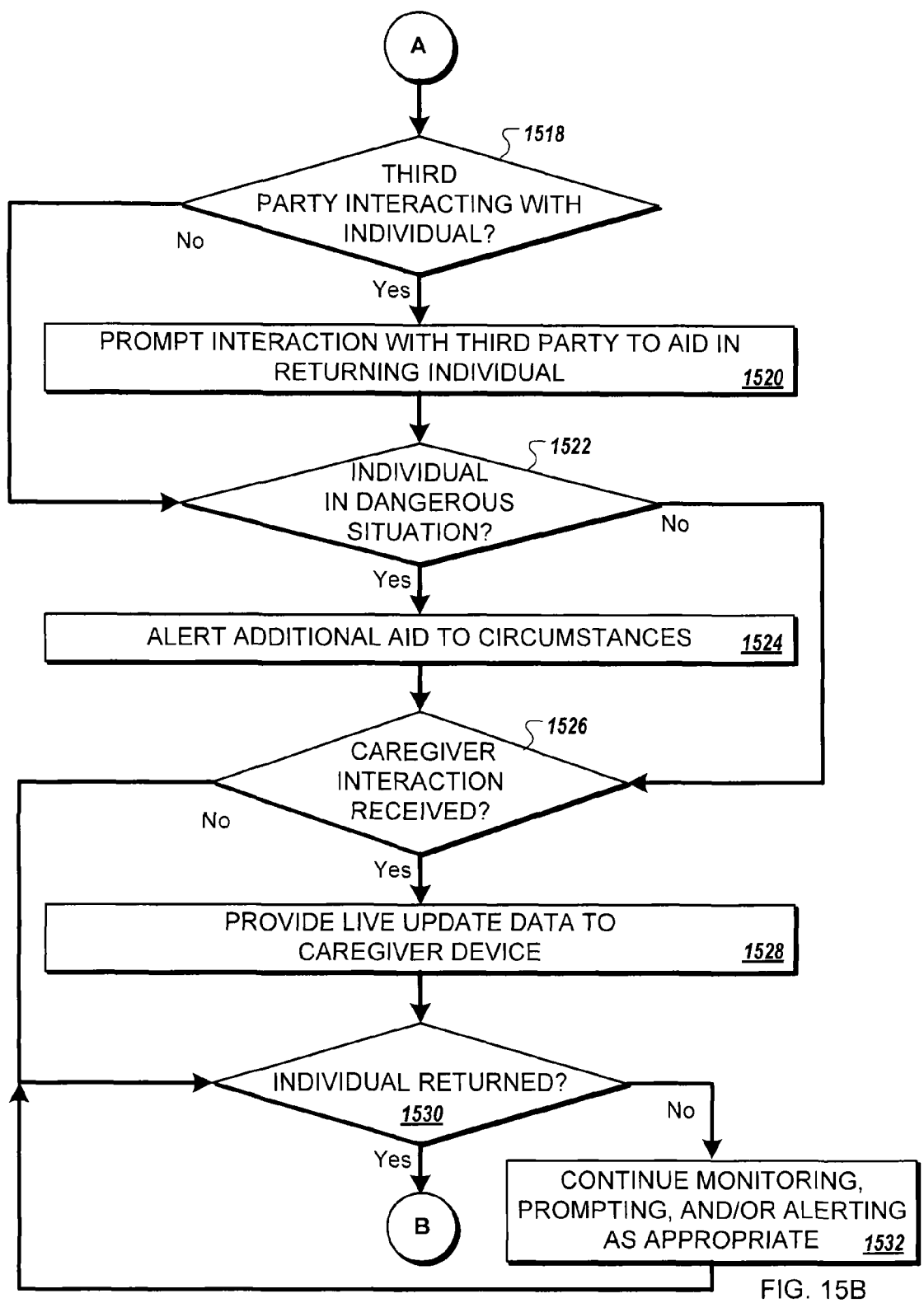

FIGS. 15A and 15B are a flow chart of an example method 1500 for tracking location of an individual via a portable data collection device. The portable data collection device, in some examples, may be a wearable data collection device such as the device 1404 described in relation to FIG. 14, a handheld electronic device such as a smart phone, tablet computer, or digital entertainment device, or a wearable device such as a smart watch or a specialized health and fitness computing device. Further, aspects of the method 1500 may be implemented upon two or more computing devices functioning in relation to each other, such as both a smart watch and a portable digital entertainment device.

Turning to FIG. 15A, in some implementations, the method 1500 begins with receiving one or more parameters identifying a permissible region for movement of an individual having a portable data collection device (1502). As described in relation to FIG. 14, the permissible region may include one or more of a radius, perimeter, or other regions and/or zones for permissible movement of the individual. Additionally, one or more exclusion zones, such as a swimming pool within the back yard of a property or a road abutting the park, may be identified within an otherwise permissible zone. The parameters, for example, may be submitted by a caregiver for monitoring movements of a child or dependent adult. The parameters, in one example, may pertain to a particular permissible region of a number of permissible regions selected based upon preferences established by the caregiver. For example, the permissible region may be selected based upon a present location of the portable data collection device. In another example, the permissible region may be selected based upon a present location of a separate portable computing device, such as a device recognized as the caregiver device. In other examples, preferences may include a time of day, a day of the week, and/or a nearest registered computing device to the portable data collection device (e.g., out of a number of devices registered to a number of individuals identified as caregivers of the individual such as parents, siblings, teachers, babysitters, etc.).

In some implementations, tracking is activated on the portable data collection device (1504). For example, a position monitoring algorithm may be activated to track a present position of the individual via position tracking elements of the portable data collection device, as described in relation to FIG. 14. Tracking, in one example, may be activated upon arrival within or nearby the permissible region. For example, the position monitoring algorithm may be activated upon arrival, based upon position monitoring of a caregiver data collection device, of the individual and the caregiver at a designated permissible region (e.g., home, school, etc.). In another example, the caregiver may activate tracking via a software application integrated with the position tracking algorithm of the portable data collection device. In a further example, tracking may be activated upon activation (e.g., powering up) of the portable data collection device.

In some implementations, the location of the portable data collection device is periodically monitored (1506). Monitoring the location of the portable data collection device, for example, may involve monitoring the position relative to the permissible region. The monitoring period, for example, may be based upon recent speeds of the individual (e.g., relatively stationary vs. running or bicycling), historical speeds of the individual, a present power level of the portable data collection device and/or preferences of the caregiver. In one example, the lag between periodic monitoring is automatically adjusted based upon a relative change in position of the individual during a recent period of time. In another example, the lag between periodic monitoring is automatically adjusted based upon a distance of the individual from a perimeter of the permissible region and/or a perimeter of an exclusion zone within the permissible region. For example, as the individual approaches an exclusion zone or the perimeter of the permissible region, the period between position monitoring may be shortened to identify a point at which the individual moves beyond the bounds of the permissible region.

In some implementations, if the individual has exceeded a permissible region (1508) or a recovery mode operation of the portable data collection device is otherwise manually activated (1510), a position monitoring algorithm is adjusted for tracking a present position of the individual (1512). As described above in relation to step 1506, upon identifying the individual exceeding the bounds of the permissible region or entering into an exclusion zone, the period between position monitoring may be shortened to more closely track the movements of the individual. Further, the period between position monitoring may be adjusted based in part upon a present power level of the portable data collection device, to avoid losing power prior to recovering the individual into the permissible region. As discussed in relation to FIG. 14, a "rescue mode" may be triggered by the individual or the caregiver to locate and/or return the individual.

In some implementations, the individual is prompted to return to the permissible region 1514. Audio and/or image-based prompts may be issued via the portable data collection device and/or a separate device in communication with the portable data collection device. Prompting is described in greater detail in relation to the return prompting algorithm 1416b of FIG. 14.

In some implementations, an alert is issued to a caregiver regarding the present position of the portable data collection device (1516). The alert, for example, may include a wireless transmission from the portable data collection device or a device in communication with the portable data collection device (e.g., network-based processing system receiving data from the portable data collection device) to a computing device of a caregiver. The alert, for example, may be issued via a software application integrated with the monitoring system implemented upon the portable data collection device. In other examples, the alert may include a text message, email message, SMS message, or other electronic messaging system capable of relaying, in real time, information regarding the individual's movements. Aspects of caregiver alert are described in greater detail in relation to the wander alert algorithm 1416c of FIG. 14.

Turning to FIG. 15B, if it is determined that a third party is within a vicinity of the individual and is available to interact (or is already interacting) with the individual (1518), in some implementations, the individual is prompted to interact with the third party to aid in returning the individual to the permissible region and/or to the caregiver (1520). For example, as described in relation to the echo prompting algorithm 1416*i* of FIG. 14, the individual may be prompted, via audible and/or visible cues, to repeat one or more messages for the benefit of the third party. In another example, the individual may be prompted to approach the third party, and the portable data collection device may play a message (e.g., via an external speaker, etc.) for the benefit of the third party. Further, statements made by the individual and/or the third party may be parsed by a voice recognition algorithm. For example, audio captured by the portable data collection device may be parsed to recognize questions posed by the third party and/or to confirm echoing of prompted messages by the individual.

In some implementations, if the individual is in a dangerous situation (1522), additional aid is alerted to the circumstances (1524). Dangerous situations, in some examples, may include playing at the edge of a body of water, being approached by a third party (e.g., another child, adult, or animal), in a bullying, aggressive, or otherwise threatening manner, being impacted at substantial force (e.g., being hit by a bicycle or vehicle, being kicked or punched, etc.), or taking a serious fall (e.g., falling down stairs, off of playground equipment, etc.). As described in relation to FIG. 14, the impact and fall detection algorithm 1416*e* may be used to detect impacts and falls, while the aggressive behavior and other danger detection 1416*d* may be used to detect other threatening circumstances. If the individual requires immediate help due to injury or threat, the portable data collection device may trigger an alert to caregivers, medics, and/or other authorities. As previously discussed, alerts can take place of any electronic transmission resulting in a real-time message to a separate computing device.

In some implementations, if a caregiver interaction is received (1526), live update data is provided to a caregiver device (1528). As discussed in relation to FIG. 14, the caregiver may select, within a software application or web portal, to review viewpoint image data, image data of a facial region of the individual, and/or audio data captured by the portable data collection device. Further, the caregiver may activate an interactive audio session with the individual, establishing a two-way audio communication channel with the portable data collection device or other computing device carried by the individual.

In some implementations, position is continued to be monitored (1532) along with prompting and/or alerting as appropriate, until the individual is returned to the permissible region and/or the caregiver (1530). In one example, the method 1500 may return to periodically monitoring the position of the portable data collection device (1506) upon identifying that the current position of the portable data collection device is once again within the permissible region. In another example, the method 1500 may continue in recovery mode until the caregiver has acknowledged, via a control presented within a software application or web portal, that the individual has been recovered. In a third example, upon recovering the individual, the caregiver may reset the operating mode of the portable data collection device to periodic monitoring, for example via a control which is password-protected or otherwise unavailable for activation by the individual.

Although described as a particular series of operations, in other implementations, one or more steps of the method 1500 may be executed in a different order. For example, the caregiver alert (1516) may be issued prior to prompting the individual to return to the permissible region (1514). In another example, prior to prompting interaction with a third party (1520), the method may determine if the third party poses a dangerous situation to the individual (1522).

In further implementations, one or more steps of the method 1500 may be excluded and/or one or more additional steps may be added to the method 1500. For example, position monitoring may not be adjusted (1512) based upon moving from monitoring mode to recovery mode. Further, if the portable data collection device has no ability to supply audio or video output to the individual, the method does not prompt the individual to return to the permissible region (1514) or prompt interaction between the individual and a third party (1520). Further modifications of the method 1500 are possible without exceeding the scope and spirit of the method 1500.

Figure 12:
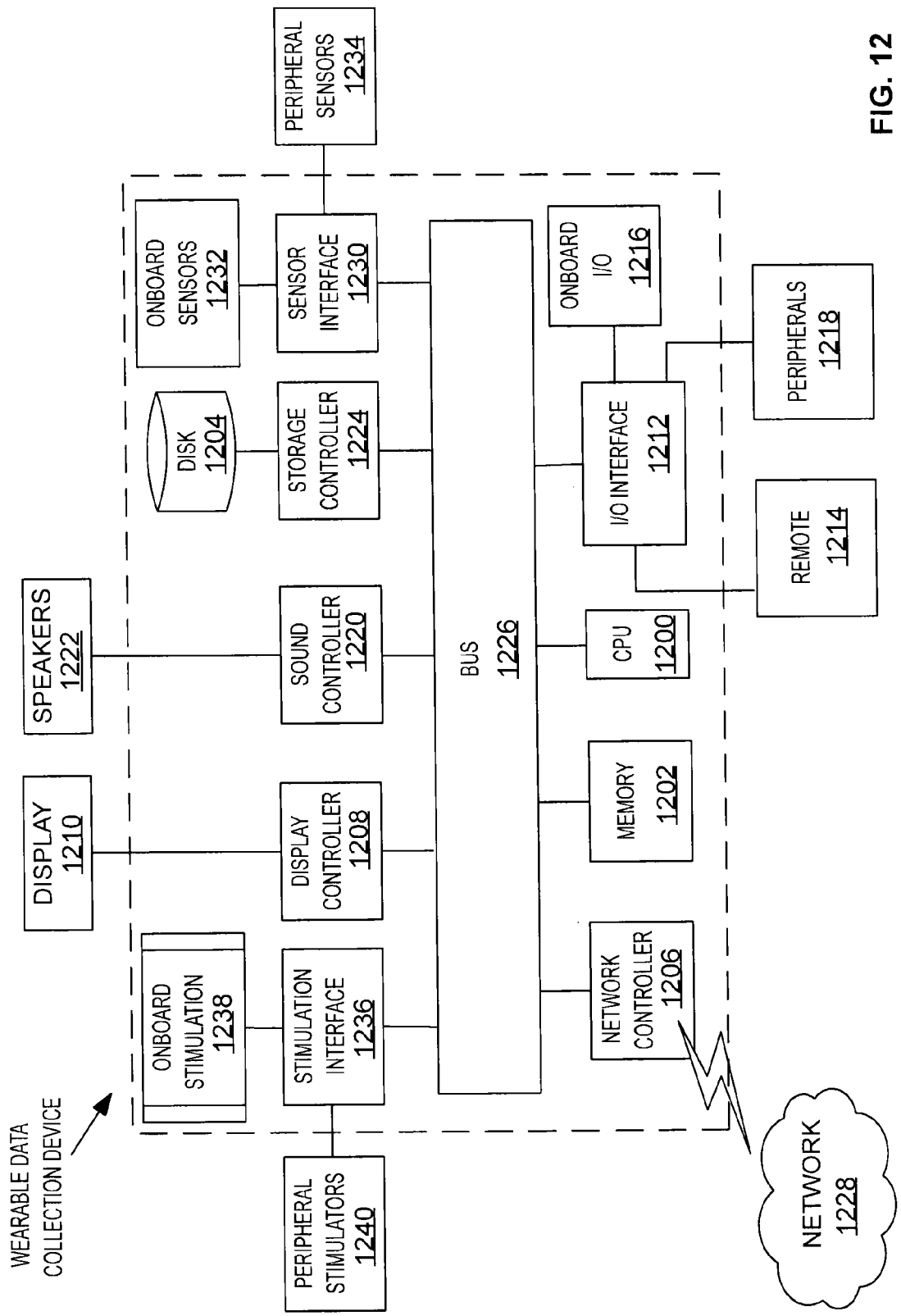
FIG. 12 is a block diagram of an example wearable computing device.

Next, a hardware description of an example wearable data collection device according to exemplary embodiments is described with reference to FIG. 12. In FIG. 12, the wearable data collection device includes a CPU 1200 which performs a portion of the processes described above. The process data and instructions may be stored in memory 1202. These processes and instructions may also be stored on a storage medium disk 1204 such as a portable storage medium or may be stored remotely. Further, the claimed advancements are not limited by the form of the computer-readable media on which the instructions of the inventive process are stored. For example, the instructions may be stored in FLASH memory, RAM, ROM, or any other information processing device with which the wearable computing system communicates, such as a server or computer.

Further, components of the claimed advancements may be provided as a utility application, background daemon, or component of an operating system, or combination thereof, executing in conjunction with CPU 1200 and an operating system such as and other systems known to those skilled in the art.

CPU 1200 may be an ARM processor, system-on-a-chip (SOC), microprocessor, microcontroller, digital signal processor (DSP), or may be other processor types that would be recognized by one of ordinary skill in the art. Further, CPU 1200 may be implemented as multiple processors cooperatively working in parallel to perform the instructions of the inventive processes described above.

The wearable computing system in FIG. 12 also includes a network controller 1206 for interfacing with network 1228. As can be appreciated, the network 1228 can be a public network, such as the Internet, or a private network such as an LAN or WAN network, or any combination thereof and can also include PSTN or ISDN sub-networks. The network 1228 can can be wireless such as a cellular network including EDGE, 3G and 4G wireless cellular systems. The wireless network can also be Wi-Fi, Bluetooth, or any other wireless form of communication that is known.

The wearable data collection device further includes a display controller 1208 interfacing with display 1210, such as a remotely located display or a heads up display. A general purpose I/O interface 1212 interfaces with an input device (e.g., microphone for voice commands, etc.). General purpose I/O interface can also communicate with a variety of on board I/O devices 1216 and/or peripheral I/O devices 1218 including, in some examples, a video recording system, audio recording system, microphone, gyroscopes, accelerometers, gravity sensors, linear accelerometers, global positioning system, magnetometers, EEG, EMG, EKG, bar code scanner, QR code scanner, RFID scanner, temperature monitor, skin dynamics sensors, scent monitor, light monitor, blood dynamics and chemistry monitor, vestibular dynamics monitor, external storage devices, and external speaker systems.

A sound controller 1220 is also provided in the wearable data collection device, to interface with speakers/microphone 1222 thereby both recording and presenting sounds to the wearer.

The general purpose storage controller 1224 connects the storage medium disk 1204 with communication bus 1226, such as a parallel bus or a serial bus such as a Universal Serial Bus (USB), or similar, for interconnecting all of the components of the wearable computing system. A description of the general features and functionality of the display 1210, as well as the display controller 1208, storage controller 1224, network controller 1206, sound controller 1220, and general purpose I/O interface 1212 is omitted herein for brevity as these features are known.

The wearable data collection device in FIG. 12, in some embodiments, includes a sensor interface 1230 configured to communicate with one or more onboard sensors 1232 and/or one or more peripheral sensors 1234. The onboard sensors 1232, for example, can be incorporated directly into the internal electronics and/or a housing of the wearable device. The peripheral sensors 1234 can be in direct physical contact with the sensor interface 1230 e.g. via a wire; or in wireless contact e.g. via a Bluetooth, Wi-Fi or NFC connection. Alternatively, one or more of the peripheral sensors 1234 may communicate with the sensor interface 1230 via conduction through the body tissue or via other mechanisms. Furthermore, one or more peripheral sensors 1234 may be in indirect contact e.g. via intermediary servers or storage devices that are based in the network 1228; or in (wired, wireless or indirect) contact with a signal accumulator somewhere on or off the body, which in turn is in (wired or wireless or indirect) contact with the sensor interface 1230. The peripheral sensors 1234 can be arranged in various types of configurations relative to the body. For instance, they can be mounted on the body, near the body, looking at the body, and/or implanted within the body of a human or animal subject. The onboard sensors 1232 and/or peripheral sensors 1234 can include, in some examples, one or more microphones, bone-conduction microphones, physiological events microphones, cameras, video cameras, high-speed cameras, temperature monitors, accelerometers, gyroscopes, magnetic field sensors, magnetic compasses, tap sensors and/or vibration sensors—internal or external to a gyroscope/accelerometer complex, infrared sensors or cameras, and/or eye-tracking cameras or eye-tracking sensor complex. In further examples, onboard sensors 1232 and/or peripheral sensors 1234 may include one or more skin-mounted electrodes, body-proximal electrodes (contact or non-contact), pulse oximetry devices, laser and laser-light sensors, photodiodes, galvanic skin response sensor modules, RF or other electromagnetic signal detectors, electrical signal pre-amplifiers, electrical signal amplifiers, electrical signal hardware filter devices, chemical sensors, and/or artificial noses.

A group of sensors communicating with the sensor interface 1230 may be used in combination to gather a given signal type from multiple places such as in the case of EEG or skin temperature in order to generate a more complete map of signals. One or more sensors communicating with the sensor interface 1230 can be used as a comparator or verification element, for example to filter, cancel, or reject other signals. For instance, a light sensor can pick up ambient light or color changes and use them to subtract or otherwise correct light-based signals from a camera pointed at the eye or skin to pick up small color or reflectance changes related to physiological events. Likewise, a microphone mounted against the body can pick up internal sounds and the voice of the subject donning the wearable data communication device and subtract the internal sounds from ambient sounds such as the voice of a separate individual or noise from environmental events, in order to more concentrate on the audible features of external events. Conversely, sensor data may be used to subtract environmental noise from body-internal sound signatures that can give evidence of physiology. Similarly, the input of multiple temperature monitors can aid in adjusting for major changes in ambient temperature or for narrowing a temperature signature to more narrowly identify the temperature of a particular element (e.g., device/electronics temperature or body temperature) without contamination from heat provided by other elements.

The wearable data collection device in FIG. 12, in some embodiments, includes a stimulation interface 1236 for supplying stimulation feedback to an individual donning the wearable data collection device. The stimulation interface 1236 is in communication with one or more onboard stimulators 1238 and/or peripheral stimulators 1240 configured to deliver electrical pulses to the individual, thereby altering physiological conditions of the individual. For example, one or more onboard stimulators 1238 and/or peripheral stimulators 1240 may be situated and/or configured to electrically stimulate heart rate or breathing or brain waves at particular frequencies. The onboard stimulators 1238 and/or peripheral stimulators 1240 can be mounted on or near the body, and/or implanted within the body, and can include components that are external and others that are internal to the body which may be configured for intercommunication with each other. In some examples, onboard stimulators 1238 and/or peripheral stimulators 1240 can include one or more of electrical signal generators and stimulation (output) electrodes, vibrator devices, heat-imparting devices, heat-extraction devices, sound generators/speakers, electromagnets, lasers, LEDs and other light sources, drug administering devices, brain stimulation or neural stimulation devices, gene transcription or expression modulation system, and/or pain or sensory stimulation generators.

Figure 13:
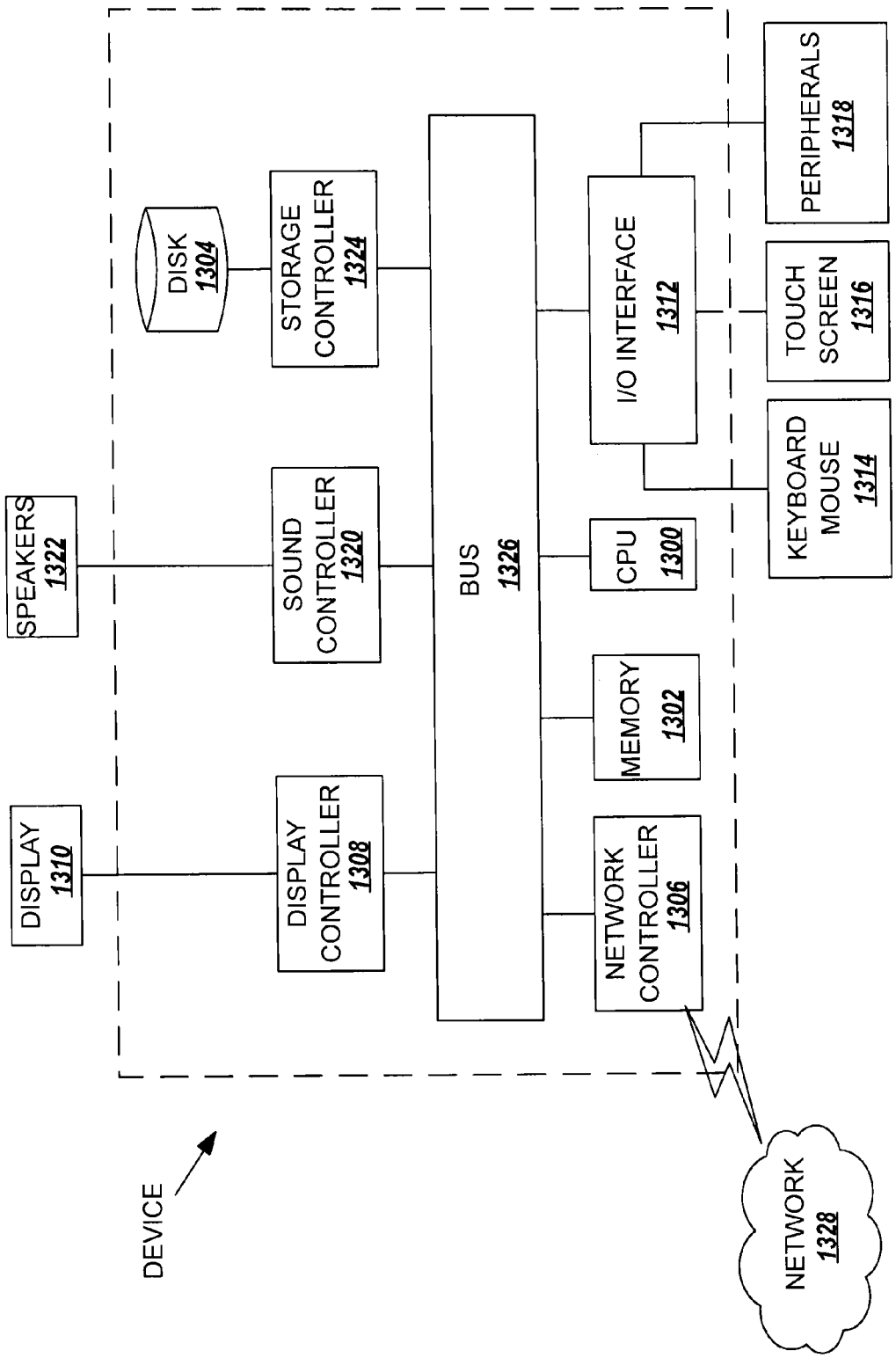
FIG. 13 is a block diagram of an example computing system.

Next, a hardware description of the computing device, mobile computing device, or server according to exemplary embodiments is described with reference to FIG. 13. In FIG. 13, the computing device, mobile computing device, or server includes a CPU 1300 which performs the processes described above. The process data and instructions may be stored in memory 1302. These processes and instructions may also be stored on a storage medium disk 1304 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device, mobile computing device, or server communicates, such as a server or computer.

Further, a portion of the claimed advancements may be provided as a utility application, background daemon, or component of an operating system, or combination thereof, executing in conjunction with CPU 1300 and an operating system such as Microsoft Windows 7, UNIX, Solaris, LINUX, Apple MAC-OS and other systems known to those skilled in the art.

CPU 1300 may be a Xenon or Core processor from Intel of America or an Opteron processor from AMD of America, or may be other processor types that would be recognized by one of ordinary skill in the art. Alternatively, the CPU 1300 may be implemented on an FPGA, ASIC, PLD or using discrete logic circuits, as one of ordinary skill in the art would recognize. Further, CPU 1300 may be implemented as multiple processors cooperatively working in parallel to perform the instructions of the inventive processes described above.

The computing device, mobile computing device, or server in FIG. 13 also includes a network controller 1306, such as an Intel Ethernet PRO network interface card from Intel Corporation of America, for interfacing with network 13X. As can be appreciated, the network 1328 can be a public network, such as the Internet, or a private network such as an LAN or WAN network, or any combination thereof and can also include PSTN or ISDN sub-networks. The network 1328 can also be wired, such as an Ethernet network, or can be wireless such as a cellular network including EDGE, 3G and 4G wireless cellular systems. The wireless network can also be Wi-Fi, Bluetooth, or any other wireless form of communication that is known.

The computing device, mobile computing device, or server further includes a display controller 1308, such as a NVIDIA GeForce GTX or Quadro graphics adaptor from NVIDIA Corporation of America for interfacing with display 1310, such as a Hewlett Packard HPL2445w LCD monitor. A general purpose I/O interface 1312 interfaces with a keyboard and/or mouse 1314 as well as a touch screen panel 1316 on or separate from display 1310. General purpose I/O interface also connects to a variety of peripherals 1318 including printers and scanners, such as an OfficeJet or DeskJet from Hewlett Packard.

A sound controller 1320 is also provided in the computing device, mobile computing device, or server, such as Sound Blaster X-Fi Titanium from Creative, to interface with speakers/microphone 1322 thereby providing sounds and/or music.

The general purpose storage controller 1324 connects the storage medium disk 1304 with communication bus 1326, which may be an ISA, EISA, VESA, PCI, or similar, for interconnecting all of the components of the computing device, mobile computing device, or server. A description of the general features and functionality of the display 1310, keyboard and/or mouse 1314, as well as the display controller 1308, storage controller 1324, network controller 1306, sound controller 1320, and general purpose I/O interface 1312 is omitted herein for brevity as these features are known.

One or more processors can be utilized to implement various functions and/or algorithms described herein, unless explicitly stated otherwise. Additionally, any functions and/or algorithms described herein, unless explicitly stated otherwise, can be performed upon one or more virtual processors, for example on one or more physical computing systems such as a computer farm or a cloud drive.

Reference has been made to flowchart illustrations and block diagrams of methods, systems and computer program products according to implementations of this disclosure. Aspects thereof are implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

A number of implementations have been described. Nevertheless, it will be understood that various modifications may be made without departing from the spirit and scope of this disclosure. For example, preferable results may be achieved if the steps of the disclosed techniques were performed in a different sequence, if components in the disclosed systems were combined in a different manner, or if the components were replaced or supplemented by other components. The functions, processes and algorithms described herein may be performed in hardware or software executed by hardware, including computer processors and/or programmable circuits configured to execute program code and/or computer instructions to execute the functions, processes and algorithms described herein. Additionally, some implementations may be performed on modules or hardware not identical to those described. Accordingly, other implementations are within the scope that may be claimed.

The invention claimed is:

1. A system comprising:
   a portable data collection device designed to be held by a user or worn upon a body of the user, the data collection device comprising
      processing circuitry, and
      a non-transitory computer readable medium having instructions stored thereon; and
   one or more input capture elements connected to and/or in communication with the portable data collection device, wherein the one or more input capture elements are positioned upon or proximate to a head of the user or directed toward the head of the user;
   wherein the instructions, when executed by the processing circuitry, cause the processing circuitry to:
      collect, over a period of time via at least one of the one or more input capture elements, sensor data, wherein the sensor data includes at least one of image data, audio data, electromagnetic data, and motion data,
      analyze the sensor data to identify a time progression of measurements including at least one of a) a plurality of involuntary small motion measurements, and b) a plurality of vibration measurements,
      analyze the time progression of measurements to identify a physiological pattern, wherein
         the physiological pattern comprises at least one of a pronounced head motion pattern and a slow-wave change pattern, and the physiological pattern is based at least in part on at least one of a) the plurality of involuntary small motion measurements and b) the plurality of vibration measurements, analyze the physiological pattern to identify a physiological state indicated by the physiological pattern, and provide, to at least one of a user of the portable data collection device and a third party computing device, feedback corresponding to the physiological pattern, wherein providing feedback to the user comprises providing feedback responsive to the physiological state indicated by the physiological pattern, wherein
the feedback comprises at least one of visual, audible, haptic, and neural stimulation feedback to the user, and
the feedback is provided via at least one output feature of one or more output features of the portable data collection device, and providing feedback to the third party computing device comprises transmitting, via a wired or wireless transmission link, a data transmission to the third party computing device identifying at least one of the physiological pattern and an identification of a physiological state indicated by the physiological pattern.

2. The system of claim 1, wherein the physiological state comprises at least one of a chronic anomalous physiological state and a temporary anomalous event state.

3. The system of claim 2, wherein the chronic anomalous physiological state comprises one or more of Autistic behaviors, a heart defect, a neurodegenerative condition, an inner ear problem, a balance problem, and a type of cardiac disease.

4. The system of claim 1, wherein analyzing the time progression of measurements to identify the physiological pattern comprises analyzing the time progression of measurements in light of additional data captured during or corresponding to the period of time, wherein the additional data is at least one of a) external to the user and b) related to the user.

5. The system of claim 4, wherein additional data external to the user comprises one or more of circadian rhythm data, seasonal data, audio data capturing background noise of a surroundings of the user light intensity data capturing light patterns of a surroundings of the user, and location data capturing one or more positions of the user.

6. The system of claim 4, wherein additional data related to the user comprises one or more of an activity pattern of the user, audio data capturing vocalizations of the user, pharmaceutical intake of the user, stimulant intake of the user, a neural state of the user, and dietary intake of the user.

7. The system of claim 4, wherein the instructions, when executed by the processing circuitry, further cause the processing circuitry to collect over the period of time via at least one of one or more additional input capture elements, at least a portion of the additional data.

8. The system of claim 1, wherein identifying the physiological pattern comprises:
accessing a baseline physiological pattern associated with at least one of the user and a group of individuals sharing one or more features of the user; and
analyzing the time progression of measurements in view of the baseline physiological pattern to identify one or more divergences or anomalies.

9. The system of claim 8, wherein the one or more features of the user comprise at least one of a physiological disability, a sensory sensitivity, and a digestive disorder diagnosis.

10. A non-transitory computer readable medium having instructions stored thereon for monitoring physiological patterns of a user of a portable data collection device, wherein the instructions, when executed by processing circuitry, cause the processing circuitry to:
collect, over a period of time via at least one of one or more input capture elements, sensor data, wherein the sensor data includes at least one of image data, audio data, electromagnetic data, and motion data, wherein
the one or more input capture elements connected to and/or in communication with the portable data collection device, and
the one or more input capture elements are positioned upon or proximate to a head of the user or directed toward the head of the user;
analyze the sensor data to identify a time progression of measurements including at least one of a) a plurality of involuntary small motion measurements, and b) a plurality of vibration measurements;
analyze the time progression of measurements to identify a physiological pattern, wherein
the physiological pattern comprises at least one of a pronounced head motion pattern and a slow-wave change pattern, and
the physiological pattern is based at least in part on at least one of a) the plurality of involuntary small motion measurements and b) the plurality of vibration measurements;
analyze the physiological pattern to identify a physiological state indicated by the physiological pattern; and
provide, to at least one of a user of the portable data collection device and a third party computing device, feedback corresponding to the physiological pattern, wherein
providing feedback to the user comprises providing feedback responsive to the physiological state indicated by the physiological pattern, wherein
the feedback comprises at least one of visual, audible, haptic, and neural stimulation feedback to the user, and
the feedback is provided via at least one output feature of one or more output features of the portable data collection device, and
providing feedback to the third party computing device comprises transmitting, via a wired or wireless transmission link, a data transmission to the third party computing device identifying at least one of the physiological pattern and the identification of the physiological state.

11. The non-transitory computer readable medium of claim 10, wherein analyzing the time progression of measurements to identify the physiological pattern comprises analyzing the time progression of measurements in light of additional data captured during or corresponding to the period of time, wherein the additional data is at least one of a) external to the user and b) related to the user.

12. The non-transitory computer readable medium of claim 11, wherein additional data external to the user comprises one or more of circadian rhythm data, seasonal data, audio data capturing background noise of a surroundings of the user, light intensity data capturing light patterns of a surroundings of the user, and location data capturing one or more positions of the user.

13. The non-transitory computer readable medium of claim 11, wherein additional data related to the user comprises one or more of an activity pattern of the user, audio data capturing vocalizations of the user, pharmaceutical intake of the user, stimulant intake of the user, a neural state of the user, and dietary intake of the user.

14. The non-transitory computer readable medium of claim 11, wherein the instructions, when executed by the processing circuitry, further cause the processing circuitry to collect over the period of time via at least one of one or more additional input capture elements, at least a portion of the additional data.

15. The non-transitory computer readable medium of claim 10, wherein identifying the physiological pattern comprises:
   accessing a baseline physiological pattern associated with at least one of the user and a group of individuals sharing one or more features of the user; and
   analyzing the time progression of measurements in view of the baseline physiological pattern to identify one or more divergences or anomalies.

16. The non-transitory computer readable medium of claim 15, wherein the one or more features of the user comprise at least one of a physiological disability, a sensory sensitivity, and a digestive disorder diagnosis.

17. A method for monitoring physiological patterns of a user of a portable data collection device configured to be worn upon a body of the user or held by the user, the method comprising:
   collecting, over a period of time via at least one of one or more input capture elements, sensor data, wherein the sensor data includes at least one of image data, audio data, electromagnetic data, and motion data, wherein
      the one or more input capture elements are connected to and/or in communication with the portable data collection device, and
      the one or more input capture elements are positioned upon or proximate to a head of the user or directed toward the head of the user;
   analyzing, by processing circuitry, the sensor data to identify a time progression of measurements including a) a plurality of involuntary small motion measurements and b) a plurality of vibration measurements;
   analyzing, by the processing circuitry, the time progression of measurements to identify a physiological pattern, wherein
      the physiological pattern comprises at least one of a pronounced head motion pattern and a slow-wave change pattern, and
      the physiological pattern is based at least in part on at least one of a) the plurality of involuntary small motion measurements and b) the plurality of vibration measurements;
   analyzing, by the processing circuitry, the physiological pattern to identify a physiological state indicated by the physiological pattern; and
   providing, by the processing circuitry to at least one of a user of the portable data collection device and a third party computing device, feedback corresponding to the physiological pattern, wherein
   providing feedback to the user comprises providing feedback responsive to the physiological state indicated by the physiological pattern, wherein
      the feedback comprises at least one of visual, audible, haptic, and neural stimulation feedback to the user, and
      the feedback is provided via at least one output feature of one or more output features of the portable data collection device, and
   providing feedback to the third party computing device comprises transmitting, via a wired or wireless transmission link, a data transmission to the third party computing device identifying at least one of the physiological pattern and the identification of the physiological state.

18. The method of claim 17, wherein the physiological state comprises at least one of a chronic anomalous physiological state and a temporary anomalous event state.

19. The method of claim 18, wherein the chronic anomalous physiological state comprises one or more of Autistic behaviors, a heart defect, a neurodegenerative condition, an inner ear problem, a balance problem, and a type of cardiac disease.

20. The method of claim 17, wherein analyzing the time progression of measurements to identify the physiological pattern comprises analyzing the time progression of measurements in light of additional data captured during or corresponding to the period of time, wherein the additional data is at least one of a) external to the user and b) related to the user.

21. The method of claim 20, wherein additional data external to the user comprises one or more of circadian rhythm data, seasonal data, audio data capturing background noise of a surroundings of the user, light intensity data capturing light patterns of a surroundings of the user, and location data capturing one or more positions of the user.

22. The method of claim 20, wherein additional data related to the user comprises one or more of an activity pattern of the user, audio data capturing vocalizations of the user, pharmaceutical intake of the user, stimulant intake of the wearer, a neural state of the user, and dietary intake of the user.

23. The method of claim 20, further comprising collecting, over the period of time via at least one of one or more additional input capture elements, at least a portion of the additional data.

24. The method of claim 17, wherein identifying the physiological pattern comprises:
   accessing a baseline physiological pattern associated with at least one of the user and a group of individuals sharing one or more features of the user; and
   analyzing the time progression of measurements in view of the baseline physiological pattern to identify one or more divergences or anomalies.

25. The system of claim 1, wherein the plurality of vibration measurements comprises sound of breathing.

26. The system of claim 1, wherein the instructions, when executed by the processing circuitry, cause the processing circuitry to store, upon a non-transitory computer readable storage device, the physiological pattern.

27. The system of claim 1, wherein the data collection device is designed to be worn upon the head of the user.

* * * * *